US009944998B2

(12) United States Patent
Karlin-Neumann et al.

(10) Patent No.: US 9,944,998 B2
(45) Date of Patent: Apr. 17, 2018

(54) GENETIC ASSAYS

(71) Applicant: Bio-Rad Laboratories, Inc., Hercules, CA (US)

(72) Inventors: George Karlin-Neumann, Palo Alto, CA (US); Svilen Tzonev, Pleasanton, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 14/341,677

(22) Filed: Jul. 25, 2014

(65) Prior Publication Data
US 2015/0038356 A1 Feb. 5, 2015

Related U.S. Application Data

(60) Provisional application No. 61/858,311, filed on Jul. 25, 2013, provisional application No. 61/899,027, filed on Nov. 1, 2013.

(51) Int. Cl.
C12N 15/10 (2006.01)
C12Q 1/70 (2006.01)
C12Q 1/68 (2018.01)
G01N 33/569 (2006.01)

(52) U.S. Cl.
CPC ......... *C12Q 1/703* (2013.01); *C12N 15/102* (2013.01); *C12Q 1/6827* (2013.01); *C12Q 1/70* (2013.01); *C12Q 1/701* (2013.01); *G01N 33/56983* (2013.01); *C12Q 2600/156* (2013.01); *G01N 2458/10* (2013.01)

(58) Field of Classification Search
None
See application file for complete search history.

(56) References Cited

U.S. PATENT DOCUMENTS

| | | | |
|---|---|---|---|
| 4,469,863 A | 9/1984 | Ts'o et al. | |
| 4,683,194 A | 7/1987 | Saiki et al. | |
| 4,988,617 A | 1/1991 | Landegren et al. | |
| 5,034,506 A | 7/1991 | Summerton et al. | |
| 5,216,141 A | 6/1993 | Benner | |
| 5,235,033 A | 8/1993 | Summerton et al. | |
| 5,242,794 A | 9/1993 | Whiteley et al. | |
| 5,386,023 A | 1/1995 | Sanghvi et al. | |
| 5,494,810 A | 2/1996 | Barany et al. | |
| 5,602,240 A | 2/1997 | De Mesmaeker et al. | |
| 5,637,684 A | 6/1997 | Cook et al. | |
| 5,644,048 A | 7/1997 | Yau et al. | |
| 5,952,481 A | 9/1999 | Markham et al. | |
| 6,143,496 A | 11/2000 | Brown et al. | |
| 6,180,349 B1 | 1/2001 | Ginzinger et al. | |
| 6,203,989 B1 | 3/2001 | Goldberg et al. | |
| 6,440,706 B1 | 8/2002 | Vogelstein et al. | |
| 6,558,928 B1 | 5/2003 | Landegren | |
| 6,582,938 B1 | 6/2003 | Su et al. | |
| 6,858,412 B2 | 2/2005 | Willis et al. | |
| 6,953,663 B1 | 10/2005 | Lipshutz et al. | |
| 7,041,481 B2 | 5/2006 | Anderson et al. | |
| 7,074,564 B2 | 7/2006 | Landegren | |
| 7,256,020 B2 | 8/2007 | Lyamichev et al. | |
| 7,320,860 B2 | 1/2008 | Landegren et al. | |
| 7,332,275 B2 | 2/2008 | Braun et al. | |
| 7,351,528 B2 | 4/2008 | Landegren | |
| 7,424,368 B2 | 9/2008 | Huang et al. | |
| 7,510,829 B2 | 3/2009 | Faham et al. | |
| 7,622,280 B2 | 11/2009 | Holliger et al. | |
| 7,674,587 B2 | 3/2010 | Lipshutz et al. | |
| 7,700,323 B2 | 4/2010 | Willis et al. | |
| 7,700,325 B2 | 4/2010 | Cantor et al. | |
| 7,790,388 B2 | 9/2010 | Landegren et al. | |
| 7,811,757 B2 | 10/2010 | Shuber | |
| 7,822,555 B2 | 10/2010 | Huang et al. | |
| 7,968,287 B2 | 6/2011 | Griffiths et al. | |
| 8,268,564 B2 | 9/2012 | Roth et al. | |
| 8,606,526 B1 | 12/2013 | Fernandez et al. | |
| 2002/0151040 A1 | 10/2002 | O'Keefe et al. | |
| 2003/0082543 A1 | 5/2003 | Su et al. | |
| 2003/0219769 A1 | 11/2003 | Olson et al. | |
| 2004/0005710 A1 | 1/2004 | Son et al. | |
| 2004/0091905 A1 | 5/2004 | Guo | |
| 2004/0101835 A1 | 5/2004 | Willis et al. | |
| 2004/0157243 A1 | 8/2004 | Huang et al. | |
| 2004/0259778 A1 | 12/2004 | Kotani et al. | |
| 2005/0026180 A1 | 2/2005 | Willis et al. | |
| 2005/0064476 A1 | 3/2005 | Huang et al. | |
| 2005/0130217 A1 | 6/2005 | Huang et al. | |
| 2005/0272070 A1 | 12/2005 | Ehrich et al. | |
| 2006/0094111 A1 | 5/2006 | Saito et al. | |

(Continued)

FOREIGN PATENT DOCUMENTS

| | | |
|---|---|---|
| WO | 01004360 A3 | 1/2001 |
| WO | 2005054506 A2 | 6/2005 |

(Continued)

OTHER PUBLICATIONS

Takehisa et al., Journal of Virology, 1999, vol. 73 pp. 6810-6820.*
Boni et al., PLoS One, 2010, vol. 5, pp. 1-11.*
Nada Malou et al., "Immuno-PCR: a promising ultrasensitive diagnostic method to detect antigens and antibodies", Trends in Microbiology, vol. 19, No. 16, dated Jun. 2011, pp. 295-302.
Blaine R. Copenheaver, Authorized Officer, U.S. Commissioner for Patents, "International Search Report" in connection with related PCT Patent Application No. PCT/US2014/048301, dated Nov. 18, 2014, 3 pages.
Blaine R. Copenheaver, Authorized Officer, U.S. Commissioner for Patents, "Written Opinion of the International Searching Authority" in connection with related PCT Patent Application No. PCT/US2014/048301, dated Nov. 18, 2014, 12 pages.
Bhat, et al. Single molecule detection in nanofluidic digital array enables accurate measurement of DNA copy number. Anal Bioanal Chem. May 2009;394(2):457-67.

(Continued)

*Primary Examiner* — Mindy G Brown
(74) *Attorney, Agent, or Firm* — Kolisch Hartwell, P.C.

(57) ABSTRACT

Provided herein are methods, compositions, systems, and kits for recombination assays, many of which involve amplification reactions such as PCR or droplet digital PCR.

24 Claims, 27 Drawing Sheets

(56) References Cited

U.S. PATENT DOCUMENTS

| | | | |
|---|---|---|---|
| 2006/0134674 A1 | 6/2006 | Huang et al. |
| 2006/0275789 A1 | 12/2006 | Willis et al. |
| 2006/0281098 A1 | 12/2006 | Miao et al. |
| 2006/0286580 A1 | 12/2006 | Lin et al. |
| 2007/0178479 A1 | 8/2007 | Willis et al. |
| 2007/0225487 A1 | 9/2007 | Nilsson et al. |
| 2007/0264642 A1 | 11/2007 | Willis et al. |
| 2008/0003142 A1 | 1/2008 | Link et al. |
| 2008/0014589 A1 | 1/2008 | Link et al. |
| 2008/0108063 A1 | 5/2008 | Lucero et al. |
| 2008/0125324 A1 | 5/2008 | Petersdorf et al. |
| 2009/0026082 A1 | 1/2009 | Rothberg et al. |
| 2009/0035762 A1 | 2/2009 | Sampas |
| 2009/0047669 A1 | 2/2009 | Zhang et al. |
| 2009/0068648 A1 | 3/2009 | Yakhini et al. |
| 2009/0069194 A1 | 3/2009 | Ramakrishnan |
| 2009/0098547 A1 | 4/2009 | Ghosh |
| 2009/0239308 A1 | 9/2009 | Dube et al. |
| 2009/0317798 A1* | 12/2009 | Heid ............. B01L 3/5027 435/6.12 |
| 2010/0092973 A1 | 4/2010 | Davies et al. |
| 2010/0093550 A1 | 4/2010 | Stuelpnagel et al. |
| 2010/0105052 A1 | 4/2010 | Drmanac et al. |
| 2010/0105112 A1 | 4/2010 | Holtze et al. |
| 2010/0129799 A1 | 5/2010 | Guomundsson et al. |
| 2010/0137163 A1 | 6/2010 | Link et al. |
| 2010/0173394 A1 | 7/2010 | Colston, Jr. et al. |
| 2010/0203538 A1 | 8/2010 | Dube et al. |
| 2010/0291568 A1 | 11/2010 | Olson et al. |
| 2010/0330619 A1 | 12/2010 | Willis et al. |
| 2011/0015084 A1 | 1/2011 | Christian et al. |
| 2011/0029251 A1 | 2/2011 | Huang et al. |
| 2011/0033848 A1 | 2/2011 | Simons |
| 2011/0143949 A1 | 6/2011 | Heid et al. |
| 2011/0159499 A1 | 6/2011 | Hindson et al. |
| 2011/0183330 A1 | 7/2011 | Lo et al. |
| 2011/0244455 A1 | 10/2011 | Larson et al. |
| 2012/0220494 A1 | 8/2012 | Samuels et al. |
| 2012/0252015 A1 | 10/2012 | Hindson et al. |
| 2012/0322058 A1 | 12/2012 | Regan et al. |
| 2013/0040824 A1 | 2/2013 | Lo et al. |
| 2013/0295568 A1 | 11/2013 | Link |
| 2014/0087962 A1 | 3/2014 | Keys |
| 2014/0162266 A1 | 6/2014 | Klitgord et al. |
| 2016/0076099 A1 | 3/2016 | Regan et al. |

FOREIGN PATENT DOCUMENTS

| | | |
|---|---|---|
| WO | 2007008605 A1 | 1/2007 |
| WO | 2007037678 A2 | 4/2007 |
| WO | 2007044091 A2 | 4/2007 |
| WO | WO 2007/081387 A1 | 7/2007 |
| WO | 2008134153 A1 | 11/2008 |
| WO | WO 2010/036352 A1 | 4/2010 |
| WO | WO 2011/132078 A2 | 10/2011 |
| WO | 2012129436 A1 | 9/2012 |
| WO | 2013049443 A1 | 4/2013 |
| WO | 2013093530 A1 | 6/2013 |
| WO | 2013109731 A1 | 7/2013 |
| WO | 2015048571 A2 | 4/2015 |

OTHER PUBLICATIONS

Boettger, et al. Structural haplotypes and recent evolution of the human 17q21.31 region. Nat Genet. Jul. 1, 2012;44(8):881-5. doi: 10.1038/ng.2334.

Brenner, et al. Gene expression analysis by massively parallel signature sequencing (MPSS) on microbead arrays. Nat Biotechnol. Jun. 2000;18(6):630-4.

Brouzes, et al. Droplet microfluidic technology for single-cell high-throughput screening. Proc Natl Acad Sci U S A. Aug. 25, 2009;106(34):14195-200.

Chetverin, et al. Nonhomologous RNA recombination in a cell-free system: evidence for a transesterification mechanism guided by secondary structure. Cell. Feb. 21, 1997;88(4):503-13.

Chetverin. The puzzle of RNA recombination. FEBS Lett. Oct. 22, 1999;460(1):1-5.

Conze, et al. Analysis of genes, transcripts, and proteins via DNA ligation. Annu Rev Anal Chem (Palo Alto Calif). 2009;2:215-39.

Diaz, et al. Strand transfer is enhanced by mismatched nucleotides at the 3' primer terminus: a possible link between HIV reverse transcriptase fidelity and recombination. Nucleic Acids Res. Aug. 1, 1996;24(15):3086-92.

Dube, et al. Mathematical Analysis of Copy Number Variation in a DNA Sample Using Digital PCR on a Nanofluidic Device. PLoS One 2008; 3(8): e2876. doi:10.1371/journal.pone.0002876.

Elnifro et al., P.E. Multiplex PCR: optimization and application in diagnostic virology. Clin. Microbiol. Rev. 13, 559-570 (2000).

Frohman, et al. in PCR Protocols (Innis, M.A., Ed.) Academic Press, New York. 1990; pp. 228-236.

Froissart, et al. Recombination every day: abundant recombination in a virus during a single multi-cellular host infection. PLoS Biol. Mar. 2005;3(3):e89. Epub Mar. 1, 2005.

Guatelli, et al. Isothermal, in vitro amplification of nucleic acids by a multienzyme reaction modeled after retroviral replication. Proc Natl Acad Sci U S A. Mar. 1990;87(5):1874-8.

Hardenbol, et al. Highly multiplexed molecular inversion probe genotyping: over 10,000 targeted SNPs genotyped in a single tube assay. Genome Res. Feb. 2005;15(2):269-75.

Harris, et al. Single-molecule DNA sequencing of a viral genome. Science. Apr. 4, 2008;320(5872):106-9.

Hindson, et al. High-throughput droplet digital PCR system for absolute quantitation of DNA copy number. Anal Chem. Nov. 15, 2011;83(22):8604-10. Epub Oct. 28, 2011.

Hyman, et al. Multiplex identification of microbes. Appl Environ Microbiol. Jun. 2010;76(12):3904-10. Epub Apr. 23, 2010.

International search report and written opinion dated Aug. 3, 2012 for PCT/US2012/025760.

International search report and written opinion dated Aug. 3, 2012 for PCT/US2012/024573.

Jarvis, et al. The polymerase in its labyrinth: mechanisms and implications of RNA recombination. Trends Genet. Jun. 1991;7(6):186-91.

Kane, et al. Rapid, high-throughput, culture-based PCR methods to analyze samples for viable spores of Bacillus anthracis and its surrogates. J Microbio Methods. 2009; 76:278-284.

Kirkegaard, et al. The mechanism of RNA recombination in poliovirus. Cell. Nov. 7, 1986;47(3):433-43.

Kwoh, et al. Transcription-based amplification system and detection of amplified human immunodeficiency virus type 1 with a bead-based sandwich hybridization format. Proc Natl Acad Sci U S A. Feb. 1989;86(4):1173-7.

Lefeuvre, et al. Widely conserved recombination patterns among single-stranded DNA viruses. J Virol. Mar. 2009;83(6):2697-707. doi: 10.1128/JVI.02152-08. Epub Dec. 30, 2008.

Letant, et al. Most-Probabl-Number Rapid Viability PCR method to detect viable spores Bacillus anthracis in swab samples. J Microbio Methods. 2010; 81:200-202.

Lupski. Genomic rearrangements and sporadic disease. Nat Genet. Jul. 2007;39(7 Suppl):S43-7.

Marguiles, et al. Genome sequencing in microfabricated high-density picolitre reactors. Nature. Sep. 15, 2005;437(7057):376-80. Epub Jul. 31, 2005.

Mazutis, et al. Droplet-based microfluidic systems for high-throughput amplification and analysis. Analytical Chemistry, American Chemical Society. 2009; 81(12):4813-4821.

Mosha, et al. Prevalence of genotypic resistance to antiretroviral drugs in treatment-naive youths infected with diverse HIV type 1 subtypes and recombinant forms in Dar es Salaam, Tanzania. AIDS Res Hum Retroviruses. Apr. 2011;27(4):377-82. doi: 10.1089/aid.2010.0113. Epub Oct. 18, 2010.

Negroni, et al. Homologous recombination promoted by reverse transcriptase during copying of two distinct RNA templates. Proc Natl Acad Sci U S A. Jul. 18, 1995;92(15):6971-5.

(56) References Cited

OTHER PUBLICATIONS

Ong, et al. Development of a multiplex real-time PCR assay using SYBR Green 1 chemistry for simultaneous detection and subtyping of H9N2 influenza virus type A. J Virol Methods. Sep. 2007;144(1-2):57-64. Epub May 23, 2007.
Pielberg, et al. A sensitive method for detecting variation in copy numbers of duplicated genes. Genome Res. Sep. 2003;13(9):2171-7.
Qin, et al. Studying copy number variations using a nanofluidic platform. Nucleic Acids Res. Oct. 2008;36(18):e116.
Raleigh. Organization and function of the mcrBC genes of *Escherichia coli* K-12.Mol Microbiol. May 1992;6(9):1079-86.
Rickert, et al. Multiplexed real-time PCR using universal reporters. Clin Chem. Sep. 2004;50(9):1680-3.
San Miguel, et al. Nested retrotransposons in the intergenic regions of the maize genome. Science. 1996; 274:765.
Schlingemann, et al. Novel means of viral antigen identification: improved detection of avian influenza viruses by proximity ligation. J Virol Methods. Jan. 2010;163(1):116-22. doi: 10.1016/j.jviromet.2009.09.008. Epub Sep. 12, 2009.
Schouten, et al. Relative quantification of 40 nucleic acid sequences by multiplex ligation-dependent probe amplification. Nucleic Acids. Res. 2002; 30(12):e57.
Shi, et al. Digital quanitification of gene expression emulsion PCR. Electrophoresis. Jan. 2010;31(3):528-34.
Supplementary note for Boettger, et al. Structural haplotypes and recent evolution of the human 17q21.31 region. Nat Genet. Jul. 1, 2012;44(8):881-5. doi: 10.1038/ng.2334.
Vogelstein, et al. Digital PCR. Proc Natl Acad Sci U S A. Aug. 3, 1999;96(16):9236-41.
White, et al. Digital PCR provides sensitive and absolute calibration for high throughput sequencing BMC Genomics. Mar. 19, 2009;10:116, 12 pages.
White, et al. Retrotransposons in the flanking regions of normal plant genes: a role for copia-like elements in the evolution of gene structure and expression. Proc Natl Acad Sci U S A. Dec. 6, 1994;91(25):11792-6.
Wu, et al. The ligation amplification reaction (LAR)—amplification of specific DNA sequences using sequential rounds of template-dependent ligation. Genomics. May 1989;4(4):560-9.
European Patent Office, "Extended European Search Report" in connection with related European Patent Application No. 14829649.4, dated Jun. 9, 2017, 13 pages.
Motomura, Kazushi et al., "Genetic Recombination between Human Immunodeficiency Virus Type 1 (HIV-1) and HIV-2, Two Distinct Lentiviruses", Journal of Virology, vol. 82, No. 4, Feb. 2008, pp. 1923-1933.
Tadmor, Arbel D. et al., "Supporting Online Material for Probing Individual Environmental Bacteria for Viruses by Using Microfluidic Digital PCR", Science, vol. 333, No. 6038, Jun. 30, 2011, 48 pgs.
Wang, Jianbin et al., "Genome-wide Single-Cell Analysis of Recombination Activity and De Novo Mutation Rates in Human Sperm", CELL, vol. 150, No. 2, Jul. 20, 2012, pp. 402-412.
Alitalo, Kari et al., "Homogeneously staining chromosomal regions contain amplified copies of an abundantly expressed cellular oncogene (c-myc) in malignant neuroendocrine cells from a human colon carcinoma", Proceedings of the National Academy of Sciences, vol. 80, pp. 1707-1711, Mar. 1983.
Anwar, Muhammad Zohaib et al., "Gene Locater: Genetic linkage analysis software using three-point testcross", Bioinformation, vol. 8, No. 5, Mar. 17, 2012, 3 pgs.
Barber, Robert D. et al., "GAPDH as a housekeeping gene: analysis of GAPDH mRNA expression in a panel of 72 human tissues", Physiol Genomics, vol. 21, Mar. 15, 2005, pp. 389-395.
Barrett, J. C. et al., "Haploview: analysis and visualization of LD and haplotype maps", Bioinformatics Applications Note, vol. 21, No. 2, 2005, advance access publication Aug. 5, 2004, pp. 263-265.

Beer, N. Reginald et al., "On-Chip, Real-Time, Single-Copy Polymerase Chain Reaction in Picoliter Droplets", Analytical Chemistry, vol. 79, No. 22, Nov. 15, 2007, pp. 8471-8475.
Bignell, Graham R. et al., "High-Resolution Analysis of DNA Copy Number Using Oligonucleotide Microarrays", Genome Research, vol. 14, 2004, pp. 287-295.
Boettger, Linda M. et al., "Structural haplotypes and recent evolution of the human 17q21.31 region", Nature Genetics, vol. 44, No. 8, Aug. 2012, 60 pgs.
Braun, T. et al., "Myf-6, a new member of the human gene family of myogenic determination factors: evidence for a gene cluster on chromosome 12", The EMBO Journal, vol. 9, No. 3, 1990, pp. 821-831.
Carter, Nigel P., "Methods and strategies for analyzing copy number variation using DNA microarrays", Nature Genetics, vol. 39, Jul. 2007, pp. 516-521.
Cepero, Vima et al., "MET and KRAS Gene Amplification Mediates Acquired Resistance to MET Tyrosine Kinase Inhibitors", Cancer Research, vol. 70, No. 19, Oct. 1, 2010, published online first Sep. 14, 2010, pp. 7580-7590.
Dalgleish, Raymond et al., "Copy Number of a Human Type a2 Collagen Gene", The Journal of Biological Chemistry, vol. 257, No. 22, Nov. 25, 1982, pp. 13816-13822.
Davis, Leonard G. et al. (Editors), "Basic Methods in Molecular Biology", Elsevier Scientific Publishing, NY, NY, 1991, pp. 47-65.
Dear, Paul H., "Happy mapping", Genome Mapping: A Practical Approach, vol. 184, Jan. 1, 1997, pp. 95-123.
Dear, Paul H. et al., "Happy mapping: linkage mapping using a physical analogue of meiosis", Nucleic Acids Research, vol. 21, No. 1, 1993, pp. 13-20.
Ding, Chunming et al., "Direct molecular haplotyping of long-range genomic DNA with M1-PCR", PNAS, vol. 100, No. 13, Jun. 24, 2003, pp. 7449-7453.
Dressman, Devin et al., "Transforming single DNA molecules into fluorescent magnetic particles for detection and enumeration of genetic variations", PNAS, vol. 100, No. 15, Jul. 22, 2003, pp. 8817-8822.
Fan, H. Christina et a., "Detection of Aneuploidy with Digital Polymerase Chain Reaction", Analytical Chemistry, vol. 79, No. 19, Oct. 1, 2007, pp. 7576-7579.
Iafrate, A. John et al, "Detection of large-scale variation in the human genome", Nature Genetics, vol. 36, No. 9, Sep. 2004, published online Aug. 1, 20014, pp. 949-951.
Kalinina, Olga et al., "Nanoliter scale PCR with TaqMan detection", Nucleic Acids Research, vol. 25, No. 10, 1997, pp. 1999-2004.
Kallioniemi, Olli-P. et al., "ERBB2 amplification in breast cancer analyzed by fluorescence in situ hybridization", Proceedings of the National Academy of Sciences, vol. 89, Jun. 1992, pp. 5321-5325.
Kant, Jeffrey A. et al., "Evolution and organization of the fibrinogen locus on chromosome 4: Gene duplication accompanied by transposition and inversion", Proceedings of the National Academy of Sciences, vol. 82, Apr. 1985, pp. 2344-2348.
Kato, Mamoru et al., "Population-genetic nature of copy number variations in the human genome", Human Molecular Genetics, vol. 19, No. 5, 2010, pp. 761-773.
Kaufhold, Achim et al., Identical Genes Confer High-Level Resistance to Gentamicin upon *Enterococcus faecalis*, *Enterococcus faecium*, and *Streptococcus agalactiae*, Antimicrobial Agents and Chemotherapy, vol. 36, No. 6, Jun. 1992, pp. 1215-1218.
Kilpatrick, C. William, "Noncryogenic Preservation of Mammalian Tissues for DNA Extraction: An Assessment of Storage Methods", Biochemical Genetics, vol. 40, Nos. 1/2, Feb. 2002, pp. 53-62.
European Patent Office, "Partial Supplementary European Search Report" in connection with related European Patent Application No. 14829649.4-1404, dated Mar. 2, 2017, 10 pgs.
Kwok, Pui-Yan et al., "Single-Molecule Analysis for Molecular Haplotyping", Human Mutation, vol. 23, 2004, pp. 442-446.
Leamon, John H. et al., "A massively parallel PicoTiterPlate (TM) based platform for discrete picoliter-scale polymerase chain reactions", Electrophoresis, vol. 24, 2003, pp. 3769-3777.
Lo, Y. M. Dennis et al., "Digital PCR for the molecular detection of fetal chromosomal aneuploidy" PNAS, vol. 104, No. 32, Aug. 7, 2007, pp. 13116-13121.

(56) References Cited

OTHER PUBLICATIONS

Manuelidis, L. et al., "Genomic representation of the Hind II 1.9 kb repeated DNA", Nucleic Acids Research, vol. 10, No. 10, 1982, pp. 3221-3239.
Menzel, Stephan et al., "Experimental Generation of SNP Haplotype Signatures in Patients with Sickle Cell Anaemia", PLoS One, vol. 5, Issue 9, Sep. 2010, pp. 1-8.
Michalatos-Beloin, Sonia et al., "Molecular haplotyping of genetic markers 10 kb apart by allele-specific long-range PCR", Nucleic Acids Research, vol. 24, No. 23, 1996, pp. 4841-4843.
Mitra, Robi D. et al., "Digital genotyping and haplotyping with polymerase colonies", PNAS, vol. 100, No. 10, May 13, 2003, pp. 5926-5931.
Murthy, Sabita K. et al., "Copy Number Analysis of c-erb-B2 (Her-2/neu) and Topoisomerase IIa Genes in Breat Carcinoma by Quantitative Real-Time Polymerase Chain Reaction Using Hybridization Probes and Fluorescence In Situ Hybridization", Archives of Pathology & Laboratory Medicine, vol. 129, Jan. 2005, pp. 39-46.
Pole, Jessica C. M. et al., "Single-molecule analysis of genome rearrangements in cancer", Nucleic Acids Research, vol. 39, No. 13, Apr. 27, 2011, pp. 1-13.
Ruano, Gualberto et al., "Haplotype of multiple polymorphisms resolved by enzymatic amplification of single DNA molecules", Proceedings of the National Academy of Sciences, vol. 87, Aug. 1990, pp. 6296-6300.
Salem, Rany M. et al., "A comprehensive literature review of haplotyping software and methods for use with unrelated individuals", Human Genomics, vol. 2, No. 1, Mar. 2005, pp. 39-66.
Schaerli, Yolanda et al., "The potential of microfluidic water-in-oil droplets in experimental biology", Molecular BioSystems, vol. 5, 2009, pp. 1392-1404.
Shumaker, John M. et al., "Mutation Detection by Solid Phase Primer Extension", Human Mutation, vol. 7, 1996, pp. 346-354.
Slamon, Dennis J. et al., "Human Breast Cancer: Correlation of Relapse and Survival with Amplification of the HER-2/neu Oncogene", Science, vol. 235, Jan. 9, 1987, pp. 177-182.
Templeton, Alan R. et al., "A Cladistic Analysis of Phenotype Associations with Haplotypes Inferred from Restriction Endonuclease Mapping. II. The Analysis of Natural Populations", Genetics, vol. 120, Dec. 1988, pp. 1145-1154.
Tost, Jorg et al., "Molecular haplotyping at high througnput", Nucleic Acids Research, vol. 30, No. 19, 2002, pp. 1-8.
Wei, Hua et al., "The Fidelity Index provides a systematic quantitation of star activity of DNA restriction endonucleases", Nucleic Acids Research, vol. 36, No. 9, Apr. 15, 2008, pp. 1-10.
Wetmur, James G. et al., "Molecular haplotyping by linking emulsion PCR: analysis of paraoxonase 1 haplotypes and phenotypes", Nucleic Acids Research, vol. 33, No. 8, May 10, 2005, pp. 2615-2619.
Wikipedia-Genetic Linkage (https://en.wikipedia.org/wiki/Genetic_linkage accessed from the internet on Mar. 20, 2017).
Wilke, Klaus et al., Dianosis of Haploidy and Triploidy Based on Measurement of Gene Copy Number By Real-Time PCR), Human Mutation, vol. 16, 2000, pp. 431-436.
Williams, Richard et al., "Amplification of complex gene libraries by emulsion PCR", Nature Methods, vol. 3, No. 7, Jun. 21, 2006, pp. 545-550.
Wu, Qiang et al., "Comparative DNA Sequence Analysis of Mouse and Human Protocadherin Gene Clusters", Genome Research, vol. 11, 2001, pp. 389-404.

* cited by examiner

A   Parental Molecules

B   Parental and Recombinant Molecules

C   Parental and Recombinant Molecules and Fragments

Figure 15A

| A1 | A2 | Full length wild type |
| B1 | B2 | Full length wild type |
| A1 | B2 | Full length recombinant |
| B1 | A2 | Full length recombinant |
| A1 | | Fragment |
| A2 | | Fragment |
| B1 | | Fragment |
| B2 | | Fragment |

Figure 15C

| | | | | | |
|---|---|---|---|---|---|
| A1<br>A2<br>A1A2 | A1<br>A2<br>A1A2 | A1 A1B2<br>B1<br>B1A2 | A1 A1B2<br>A2<br>A1A2 B2 | A1 B1<br>A2 B2<br>A1A2 | A1B2<br>B1A2<br>B1B2 |
| A2 | A2 | B1<br>B1A2 | A2<br>B2 | A2 B1A2<br>B1 B2 | B1B2 |
| A1 | A1<br>↑<br>B1 | A1<br>A1B2 B2 | A1<br>B1 B2 | A1B2<br>B1B2 | |
| (---) | B1 | B2 | B1 B2 | B1B2 | |

N_11 cluster

Figure 15D

| {A1, A2} | {A1, A2, B1} +more | {A1, A2, B2} +more | {A1, A2, B1, B2} | {A1, A2, B1B2} |
|---|---|---|---|---|
| {A1A2} | {A1, B1A2} | {A1B2, A2} | {A1A2, B1, B2} | {A1A2, B1B2} |
| {A1A2, A1} | {A1A2, B1} | {A1A2, B2} | {A1B2, A2, B1} | |
| {A1A2, A2} | | | {A1B2, B1A2} | +more |
| {A1A2, A1, A2} | | | | |
| | {B1A2}    {B1A2, B1} | | {B1A2, B2} | +more |
| {A2} | {B1, A2}    {B1A2, A2} | {A2, B2} | {A2, B1, B2} | {A2, B1B2} |
| | | {A1B2}    {A1B2, A1} | {B1, A1B2} | +more |
| {A1} | {A1, B1} | {A1, B2}    {A1B2, B2} | {A1, B1, B2} | {A1, B1B2} |
| | | | {B1, B1B2}    {B2, B1B2} | {B1, B2, B1B2} |
| {---} | {B1} | {B2} | {B1, B2} | {B1B2} |

N_21 cluster

GENETIC ASSAYS

CROSS-REFERENCE

This application claims the benefit of U.S. Provisional Application No. 61/858,311, filed Jul. 25, 2013, and U.S. Provisional Application No. 61/899,027, filed Nov. 1, 2013, each of which is incorporated by reference herein in their entirety.

BACKGROUND OF THE INVENTION

Recombination, particularly viral recombination, can dramatically impact both evolution and epidemiology. In viruses, the recombination rate depends on the frequency at which co-infections occur and the frequency of genetic exchange between different viral genomes within an infected host cell. The ability to measure the recombination rate is important for understanding viral growth, virulence, and for creating attenuated strains for development of new vaccines.

Current methods for measuring the recombination rate, for example approaches involving gel electrophoresis and sequencing are either imprecise and/or time-consuming and often result in overestimation of the level of recombination. The methods, compositions, systems, and kits for recombination assays disclosed herein overcome many of these challenges. The methods, compositions, systems, and kits provided herein can also be used for other types of recombination analyses, such as bacterial recombination, recombination of V(D)J or VJ domains in immune cells, as well as other types of analyses such as haplotype analysis.

SUMMARY OF THE INVENTION

This disclosure provides methods, compositions, kits, and systems for analyzing recombination, particularly viral recombination. The methods, compositions, kits and systems are particularly useful for minimizing artifactual biases arising from recombination between viral or other genomes (e.g., any microbial genome) during the assay process.

In some aspects, provided herein are methods of performing a recombination assay comprising: a. obtaining a sample comprising genomic nucleic acids, wherein the genomic nucleic acids comprise a plurality of recombined nucleic acids, wherein each of the plurality of recombined nucleic acids comprises, on a same strand: a first sequence derived from a first genome and a second sequence derived from a second genome that is different from the first genome; b. partitioning the sample into a plurality of compartments; c. performing a reaction within the plurality of compartments; and d. enumerating the plurality of compartments that comprise both the first and second sequences in order to obtain a numerical value that can be used to calculate a proportion of the genomic nucleic acids in the sample that are recombined nucleic acids.

In some cases, the sample comprises viruses. In some cases, the sample comprises bacteria or bacterial particles. In some cases, the first and second genomes are bacterial genomes. In some cases, the sample comprises RNA. The sample may comprise DNA.

In some cases, the first and second genomes are viral genomes. In some cases, the first and second viral genomes are from different families. In some cases, the different families are selected from the group consisting of: Adenoviridae, Herpesviridae, Papillomaviridae, Polyomaviridae, Poxyiridae, Hepadnaviridae, Parvoviridae, Astroviridae, Caliciviridae, Picornaviridae, Coronaviridae, Flaviviridae, Togaviridae, Hepeviridae, Retroviridae, Orthomyxoviridae, Arenaviridae, Bunyaviridae, Filoviridae, Paramyxoviridae, Rhabdoviridae, and Reoviridae.

In some cases, the first or second viral genome is selected from the group consisting of: Adenovirus, Coxsackievirus, Epstein-Barr virus, Hepatitis A virus, Hepatitis B virus, Hepatitis C virus, Herpes simplex virus, type 2, Cytomegalovirus, Human herpesvirus, type 8, HIV, Influenza virus, Measles virus, Mumps virus, Human papillomavirus, Parainfluenza virus, Poliovirus, Rabies virus, Respiratory syncytial virus, Varicella-zoster virus, and a variant strain thereof.

In some cases, the first and second viral genomes are from a different viral strain. In some cases, the first and second viral genomes are from a different viral species. In some cases, the first and second viral genomes are from an influenza strain. In some cases, the first and second viral genomes are HIV viral genomes. In some cases, the influenza strain is H1N1, H5N1, H3N2, H7N9, or H1N2, or a recombinant strain thereof. In some cases, the first and second viral genomes are from viruses that are capable of infecting different host cell types, wherein the different host cell types are selected from the group consisting of: an avian, a dog, a swine, a human, and a horse host cell. In some cases, the first and second viral genomes are from viruses that are capable of infecting different host cell types, wherein the different host cell types are selected from the group consisting of: cows, goats, rodents, rabbits, mice, dogs, guinea pigs, and rats.

In some cases, at least one of the first and second viral sequences comprises a genetic variation. In some cases, the genetic variation is selected from the group consisting of: single nucleotide polymorphisms (SNPs), insertions, inversions, rearrangements, transversions, deletions, indels, microsatellite repeats, minisatellite repeats, short tandem repeats, transposable elements, large scale structural variants, and combinations thereof. In some cases, the genetic variation is a polymorphism between two or more parental strains.

In some cases, the first and the second viral sequences are combined with a label prior to the reaction of step (c). In some cases, the first and second viral sequences are each labeled with a different color. In some cases, the sample further comprises a third viral sequence that is an allele of the first viral sequence. In some cases, the first and second viral sequences are labeled with a different color and the third viral sequence is labeled with a label that is the same color as the label of the first viral sequence but that has a different intensity than the label of the first viral sequence.

In some cases, the method has an accuracy of greater than 75%. In some cases, the method has an accuracy of at least 80%, 90%, 95%, 97%, or 99%. In some cases, the method has a sensitivity of greater than 75%. %. In some cases, the method has a sensitivity of at least 80%, 90%, 95%, 97%, or 99%. In some cases, the method is capable of detecting the recombined nucleic acids in the sample wherein less than 5% of the total genomic nucleic acids in the sample are the recombined nucleic acids. In some cases, the method is capable of detecting the recombined nucleic acids in the sample wherein less than 4%, 3%, 2%, 1%, or 0.1% of the total genomic nucleic acids in the sample are the recombined nucleic acids. In some cases, the method is capable of detecting the recombined nucleic acids in the sample wherein less than 5% of the genomic nucleic acids comprising the first sequence derived from the first genome are the recombined nucleic acids. In some cases, the method is capable of detecting the recombined nucleic acids in the sample wherein less than 4%, 3%, 2%, 1%, or 0.1% of the genomic nucleic acids comprising the first sequence derived from the first genome are the recombined nucleic acids. In some cases, less than 5% of the nucleic acids undergo recombination during the reaction of step (c). In some cases, less than 4%, 3%, 2%, 1%, or 0.1% of the nucleic acids undergo recombination during the reaction of step (c).

In some cases, the method further comprises detecting a signal emitted by one or more probes to the viral sequences within the plurality of compartments. In some cases, the method further comprises using a processor instructed by a computer-readable medium to enumerate the plurality of compartments. In some cases, the plurality of compartments are aqueous droplets within a water-in-oil emulsion. In some cases, the sample is partitioned such that each compartment contains on average a concentration of less than 0.1 genome copies per aqueous droplet. In some cases, the sample comprising viruses is partitioned such that each compartment comprises, on average, no more than one virus. In some cases, the sample comprising bacterial particles is partitioned such that each compartment comprises, on average, no more than one bacterial particle.

In some cases, a probability that the first viral sequence and the second viral sequence are colocalizing by chance within a same compartment is less than about 0.001%. In some cases, a fragmentation frequency is less than about 10%. In some cases, a distance between two viral sequences is less than about 20 kilobases. In some cases, the sample is partitioned into more than about 10,000,000 compartments. In some cases, the reaction is an amplification reaction. In some cases, the amplification reaction is a polymerase chain reaction. In some cases, the reaction comprises binding the first sequence to a probe and binding the second sequence to a different probe.

In some cases, the method further comprises determining a recombination rate or frequency for the first and second sequences based on the numerical value obtained in step (d). In some cases, the recombination rate or frequency is a viral recombination rate or frequency. In some cases, the method further comprises determining a viral load of the recombined nucleic acids based on the numerical value obtained in step (d).

In some cases, the method further comprises performing a multiplexing assay, wherein the sample further comprises a third sequence derived from a third genome and the method further comprises calculating a proportion of genomic nucleic acids that comprise the first sequence, the second sequence, and the third sequence. In some cases, the numerical value is also based on (i) the number of compartments that comprise the first sequence but not the second sequence, (ii) the number of compartments that comprise the second sequence but not the first sequence, or (iii) both (i) and (ii). In some cases, the multiplexing assay enables the identification of at least 2, 3, 4, 5, 6, 7, 8, 9, or 10 different recombinant genomes.

In some cases, the method further comprises enumerating (i) the compartments that comprise the first sequence derived from the first genome and a third sequence derived from the first genome, wherein the third sequence is an allele of the second sequence; (ii) the compartments that comprise the second sequence derived from the second genome and a fourth sequence derived from the second genome, wherein the fourth sequence is an allele of the first sequence; or (iii) both (i) and (ii).

In some cases, the method further comprises: (e) calculating a fragmentation frequency for the sample based on the number of compartments that comprise (i) the first sequence but not the second sequence; (ii) the second sequence but not the first sequence; or both (i) and (ii). In some cases, the method further comprises: (f) using the fragmentation frequency of step (e) to determine a numerical value for a portion of the sample comprising the first sequence and the second sequence co-localized in the same compartment by chance and present on separate strands; and (g) adjusting the numerical value for the plurality of recombined nucleic acids obtained in step (d) using the numerical value in step (f) in order to determine a final numerical value for the plurality of recombined nucleic acids.

In some cases, the first genome is a human genome and the second genome is a viral genome. In some cases, the sample is made up of at least 80% parental nucleic acids, wherein a parental nucleic acid is a nucleic acid comprising on the same strand: the first sequence derived from the first genome and a third sequence derived from the first genome, wherein the third sequence derived from the first genome is an allele of the second sequence derived from the second genome.

In some aspects, provided herein are methods of detecting recombined nucleic acids comprising: a. obtaining a sample comprising: (i) first parental nucleic acids comprising a first locus and a second locus located on a same first strand; (ii) second parental nucleic acids comprising a genetic variant of the first locus and a genetic variant of the second locus, wherein the genetic variants are located on a same second strand; (iii) recombined nucleic acids comprising the second locus and a genetic variant of the first locus; (iii) a first set of probes capable of specifically detecting the first locus and the genetic variant of the first locus by emitting a signal with a first color with a first intensity when detecting the first locus and of emitting a signal with the first color with an intensity different from the first intensity when detecting the genetic variant of the first locus; and (iv) a second set of probes capable of specifically detecting the second locus and a genetic variant of the second locus by emitting a signal with a second color that is different from the first color and that has a different intensity depending on whether it is detecting second locus or the genetic variant of the second locus; b. partitioning the sample into a plurality of compartments, wherein the total number of compartments is greater than ten; c. conducting a reaction within the compartments in order to enable the emission of the signals in step (a); d. enumerating a number of the compartments comprising the recombined nucleic acids by enumerating the number of compartments that comprise signals from both the second locus and the genetic variation of the first locus; and e. determining based on the enumerating of step (d) a proportion of the nucleic acids in the sample that are recombined nucleic acids in order to obtain a recombination rate.

In some aspects, provided herein are methods of detecting recombined nucleic acids comprising: a. obtaining a sample comprising: (i) first parental nucleic acids comprising a first locus and a second locus located on a same first strand; (ii) second parental nucleic acids comprising a genetic variant of the first locus and a genetic variant of the second locus, wherein the genetic variants are located on a same second strand; (iii) recombined nucleic acids comprising the second locus and a genetic variant of the first locus; (iii) a first set of probes capable of specifically detecting the first locus and the second locus by emitting a signal with a first color with a first intensity when detecting the first locus and of emitting a signal with the first color with an intensity different from the first intensity when detecting the second locus; and (iv) a second set of probes capable of specifically detecting a genetic variant of the first locus and a genetic variant of the second locus by emitting a signal with a second color that is different from the first color and that has a different intensity depending on whether it is detecting the genetic variant of the first locus or the genetic variant of the second locus; b. partitioning the sample into a plurality of compartments, wherein the total number of compartments is greater than ten; c. conducting a reaction within the compartments in order to enable the emission of the signals in step (a); d. enumerating a number of the compartments comprising the recombined nucleic acids by enumerating the number of compartments that comprise signals from both the second locus and the genetic variation of the first locus; and e. determining based on the enumerating of step (d) a proportion of the nucleic acids in the sample that are recombined nucleic acids in order to obtain a recombination rate. In some cases, the proportion reflects at least one of the following ratios: recombined nucleic acids:parental nucleic acids; recombined nucleic acids:first parental nucleic acids; recombined nucleic acids:second nucleic acids; or recombined nucleic acids:a sum of parental nucleic acids and recombined nucleic acids. In some cases, the sample further comprises: recombined nucleic acids comprising the first locus and a genetic variant of the second locus.

In some cases, the method further comprises enumerating the number of compartments that comprise recombined nucleic acids comprising the first locus and a genetic variant of the second locus. In some cases, the enumerating comprises detecting the color and intensity of the signals emitted by the first and second probe sets.

In some cases, a fragmentation frequency is less than about 10%. In some cases, the method further comprises: (f) calculating a fragmentation frequency for the sample based on the number of compartments that comprise (i) the signal from the second locus but not the signal from the genetic variation of the first locus; (ii) the signal from the genetic variation of the first locus but not the signal from the second locus; or both (i) and (ii). In some cases, the method further comprises: (g) using the fragmentation frequency of step (f) to determine a numerical value for a portion of the sample comprising the genetic variation of the first locus and the second locus co-localized in the same compartment by chance and present on separate strands; and (h) adjusting the numerical value for the plurality of recombined nucleic acids obtained in step (d) using the numerical value in step (g) in order to determine a final numerical value for the plurality of recombined nucleic acids.

In some cases, the first set of probes comprises a polynucleotide attached to a fluorophore. In some cases, the polynucleotide is capable of hybridizing to the first locus with a first affinity and to the genetic variant of the first locus with a second affinity that is different from the first affinity. In some cases, the first locus comprises a wild type sequence and the genetic variant of the first locus comprises a single nucleotide polymorphism of the wild type sequence.

In some cases, the nucleic acids are derived from a viral genome. In some cases, the sample is a cellular sample. In some cases, the cellular sample comprises cells infected with a virus. In some cases, the sample is a sample of viruses. In some cases, the compartments are droplets within an emulsion. In some cases, the sample comprises genomic nucleic acids and the genomic nucleic acids are partitioned such that at most 0.01 genome copies are present in each compartment. In some cases, the recombined nucleic acids comprise at least one of: (i) a V, D, or J domain; (ii) a domain from a B cell receptor; (iii) a domain from a T cell receptor; or (iii) a domain from a HLA region.

In some aspects, provided herein are methods of performing a viral particle assay comprising: a. contacting a sample comprising a viral particle with a first antibody that binds to a first epitope on the viral particle, wherein the first antibody is connected to a first polynucleotide; b. contacting the sample comprising the viral particle with a second antibody that binds to a second epitope on the viral particle, wherein the second epitope is derived from a different viral particle and wherein the second antibody is connected to a second polynucleotide capable of directly or indirectly binding to the first polynucleotide; c. partitioning the sample into discrete compartments; d. performing an amplification reaction within the discrete compartments; and e. identifying a recombinant polypeptide if an amplification reaction product is present in one or more of the discrete compartments.

In some cases, the first polynucleotide is directly linked to the first antibody. In some cases, the first polynucleotide is linked to the first antibody through a linker. In some cases, the linker is an antibody or polyethylene glycol (PEG) group.

In some cases, the first epitope is present on a viral capsid or an envelope protein. In some cases, the first epitope is present on a viral hemagglutinin (HA) or a neuraminidase (NA) protein. In some cases, the first epitope is derived from an HIV virus. In some cases, the first polynucleotide is capable of specifically hybridizing to the second polynucleotide. In some cases, the first polynucleotide is capable of specifically hybridizing to a third polynucleotide, wherein the third polynucleotide is capable of specifically hybridizing to the second polynucleotide.

In some aspects, provided herein are methods of analyzing nucleic acids and polypeptides of a viral particle comprising: a. obtaining a sample of viral particles, wherein the viral particles comprise a first viral sequence derived from a first viral genome and a second viral sequence derived from a second viral genome that is different from the first viral genome, wherein the first and second viral sequence are present on the same strand; b. partitioning the viral particles into compartments so that, on average, not more than one viral particle is present in each compartment; c. detecting the first and second viral sequences by performing a first amplification reaction within the compartment; d. detecting the polypeptides by contacting the polypeptides with an antibody linked to an oligonucleotide primer and performing an amplification reaction within the compartment; and e. detecting a recombination event if the first and second viral sequences are present in the same compartment.

In some aspects, provided herein are methods of selectively propagating a virus of interest comprising: a. contacting a test host cell with the virus of interest to allow infection of the host cell by the virus; b. propagating the virus of interest in the infected host cell; c. isolating a viral genome from the infected host cell into a discrete compartment; d. amplifying the viral genome in the discrete compartment; e. detecting the presence or absence of a genetic variation in the viral genome; and f. if the genetic variation is present, propagating additional viruses of interest from the test host cell. In some cases, the additional viruses of interest comprise a viral therapy vector. In some cases, the viral therapy vector is used for gene or cellular therapy in an organism. In some cases, the additional viruses of interest are used in a vaccine. In some cases, the vaccine is used to treat an organism.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 15A, 15B, 15C, and 15D illustrate methods to calculate viral recombination. 15A illustrates the molecular species detected in the assay. 15B illustrates a numbering scheme to identify each individual cluster. 15C illustrates all possible molecular species which may participate in any droplet. 15D illustrates possible species within a given droplet for all possible clusters, for assays that use two colors with tiered intensities.

DETAILED DESCRIPTION OF THE INVENTION

I. General Overview

Figure 1:
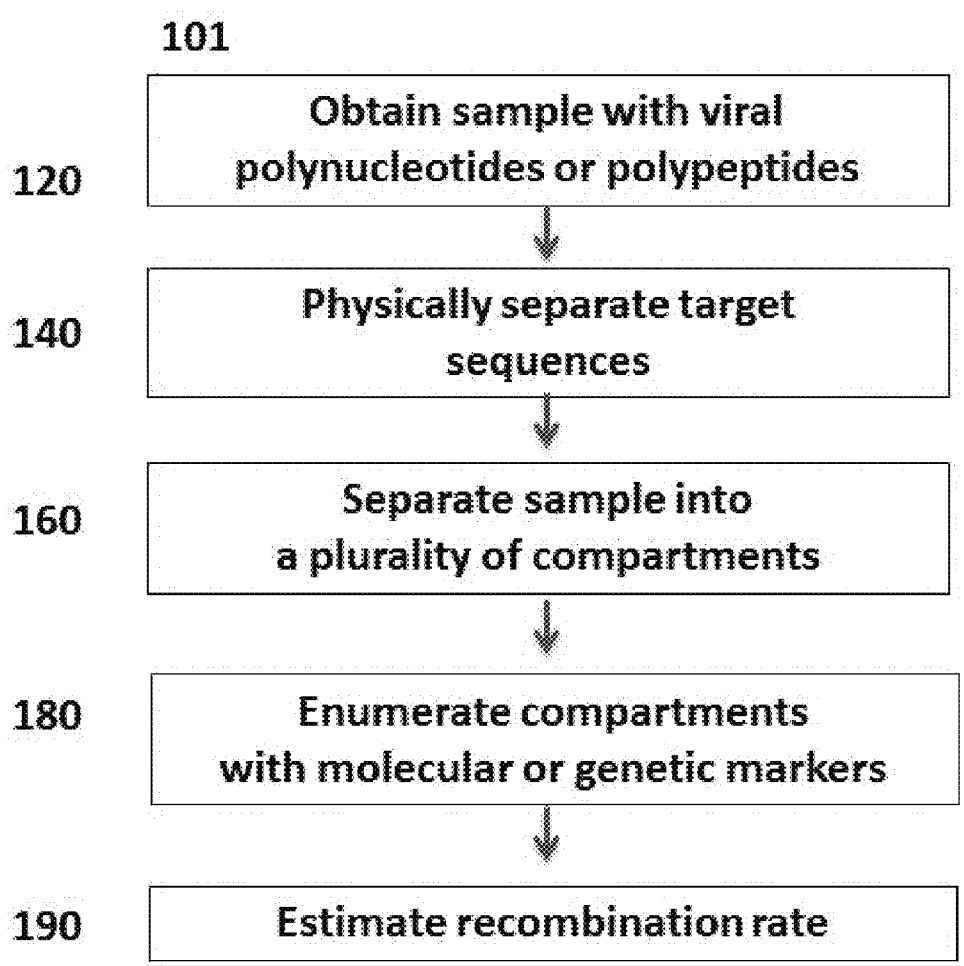
FIG. 1 provides an overview of a method for quantifying recombination rate.

This disclosure provides methods, compositions, systems, and kits for performing a recombination assay, particularly a recombination assay that distinguishes microbial particles (e.g., viruses, bacteria) from one another by nucleic acid or polypeptide analysis. In another aspect, the recombination assay is performed by analyzing both nucleic acids and polypeptides and/or macromolecules. In some cases, a plurality of recombination assays are performed in parallel. In some cases, the plurality of recombination assays are performed to detect two or more markers that appear on the same strand of nucleic acid as a result of one or more viral recombination events; in some cases, the plurality of recombination assays are performed to detect the identical markers in multiple samples, or different markers in multiple samples.

In general, a recombination assay can comprise at least the following steps. One step may comprise obtaining a biological sample that is to be assayed using the recombination assays provided herein. For example, the sample can be a viral particle, or portion thereof, e.g., viral nucleic acid. In some cases, the sample is a clinical sample, e.g., a sample obtained from a subject infected with a virus or other pathogen. The sample may be a cellular sample, or a bodily fluid. The sample may comprise nucleic acids, wherein the nucleic acids comprise a first viral sequence and a second viral sequence present on the same strand, wherein the second viral sequence is derived from a different genome from the first viral sequence. The recombination assay can further comprise the steps of partitioning the sample into a plurality of discrete compartments which allows for co-localization and isolation of discrete signals from a given sample. The recombination assay can further comprise a detecting step, wherein the first and second viral sequences are detected by performing an amplification reaction within the discrete compartments and identifying a recombination event if the first and second sequences co-localize to the same compartment. In some cases, the viral assay comprises assaying multiple viral sequences contacted with a plurality of detectable labels by analyzing the amplitude of the signal of the detectable labels and/or amplicon size. In some cases, amplicon size may be altered to control the amplitude of the signal of the detectable labels (e.g., fluorescent markers). In one example, where a sample comprises recombined nucleic acids from two parental genomes (A and B), where the A genome comprises A1 and A2 loci and the B genome comprises B1 and B2 loci that are alleles of A1 and A2, respectively, the recombined nucleic acids can be detected in one of several ways. In one example, loci may be labeled with probes of different colors and alleles may be labeled with probes of different amplitudes. For example, A1 and A2 may be labeled with probes of different color, B1 may be labeled with a probe of the same color as the A1 but that emits a signal at a different amplitude and B2 may be labeled with a probe of the same color as A2 but that emits a signal with a different amplitude. In another example, loci (e.g., A1 and A2) may be labeled with probes of the same color but that emit signals with different amplitudes and alleles (e.g., A1 and B1) may be labeled with probes with different colors. In some cases, the viral assay is conducted by adjusting primer concentration, probe concentration, primer and probe concentration, or by mixing various ratios of probes (e.g., varying ratios of fluorophores). In some cases, the assay further comprises determining a fragmentation rate for the sample. In some cases, the assay further comprises adjusting the recombination frequency value in view of the fragmentation rate of the sample.

In addition, a recombination assay can comprise obtaining a viral sample (or other sample containing a macromolecular complex) and using both antibody detection and amplification within a discrete compartment to identify nucleic acids or polypeptides in the sample. In some cases, the detection of a first and a second sequence (e.g., first and second viral sequence) is performed by the addition of antibodies ligated to oligonucleotides. The antibodies may recognize first and second sequences (e.g., viral sequences, polypeptide sequences) within the discrete compartments, and the first and second sequences may be detected by ligating the oligonucleotides together or extending one oligonucleotide after it binds to the other and performing an amplification reaction or hybridization reaction in order to detect the ligated oligonucleotides.

The various systems provided by the disclosure are generally comprised of a computer processor and software interface for instructing various devices of the system, a droplet generation device that is comprised of a microfluidics component that allows for the partitioning the sample into discrete compartments, a thermocycler device that allows for the amplification reaction to be conducted on one or more macromolecules of interest in a discrete compartment, and digital analysis device capable of detecting one or more amplifications in a discrete compartment. In a related aspect, the system can be a part of a larger system that can include machines of automation such as, pipetting, plate or liquid handling robotics, or tethered to tools that allow for further or similar sample analysis for example, sequencing, imaging, staining, or hybridization devices.

In addition, in various aspects the recombination assays provide herein can yield various types of information such as, absolute quantification of viral recombination rates or recombinant molecule frequency, viral load, marker-assisted genotyping of viral particles, molecular signature of a viral particle, virulence, and growth rate. In other aspects the recombination assays can be used for generating and propagating new in vitro or in vivo viral strains of medical interest, such as gene or cellular therapy or for scientific investigation tools such as gene-expression systems. Similarly, the recombination assays can be used for non-viral pathogens (e.g., bacteria, parasites etc.) or to detect recombination in other settings such as to detect an immune repertoire.

II. Methods for Recombination Assays

FIG. 1 illustrates an overview of an embodiment of a method of determining and quantifying a recombination event (101); this figure and the remaining figures provided in this disclosure are for illustrative purposes only and are not intended to limit the invention. The steps in FIG. 1 can be performed in any suitable order and combination and can be united with any other steps of the present disclosure. A sample of polynucleotides is obtained (120); the sample can be, e.g., nucleic acids from a biological sample, such as nucleic acids or polypeptides from a virus, bacterium, or other microbe, or from an infected subject such as a human subject. In some cases the sample is intact virus. In some cases, single viral particles (e.g., viruses, intact viruses, viral fragments, etc.) may be partitioned into individual partitions (e.g., droplets) for amplification identification (e.g., PCR) of markers. In some cases, individual partitions may also comprise one or more fragments of nucleic acid sequences. In some cases, the target nucleic acid sequences in the sample are optionally physically separated or fragmented (e.g., by restriction enzyme) (140). The sample can be partitioned into a plurality of compartments, e.g., multiple aqueous droplets within a water-in-oil emulsion (160). The number of compartments with the target sequence (e.g. molecular markers) can be enumerated and quantified (180). The recombination event of the target sequence can then further assessed to determine the recombination rate or frequency; the event may also be described by various means known in the art depending on the application (190).

A. Samples

The sample used with various applications of the methods disclosed herein can comprise a homogenous or heterogeneous population of cells, particles, microorganisms, or macromolecules.

The cells can be microbial cells, prokaryotic cells, eukaryotic cells, or cells infected with viral particles. The cells can be derived from mammalian cells. Non-limiting examples of mammalian cells that can be used include: human, non-human primate, primate, rodent, cow, sheep, lamb, monkey, gorilla, rabbit, dog, pig, mouse, rat, guinea pig, or cat. In a preferred application, the cells are human cells. In some applications, the cells are non-human mammalian cells, or even non-mammalian cells. Non-limiting examples of non-mammalian cells that can be used include: insects, birds, fish, amphibians, reptiles, microbes, protozoa, invertebrates, bacteria, plants, fungi, parasites, and viral particles.

Figure 2:
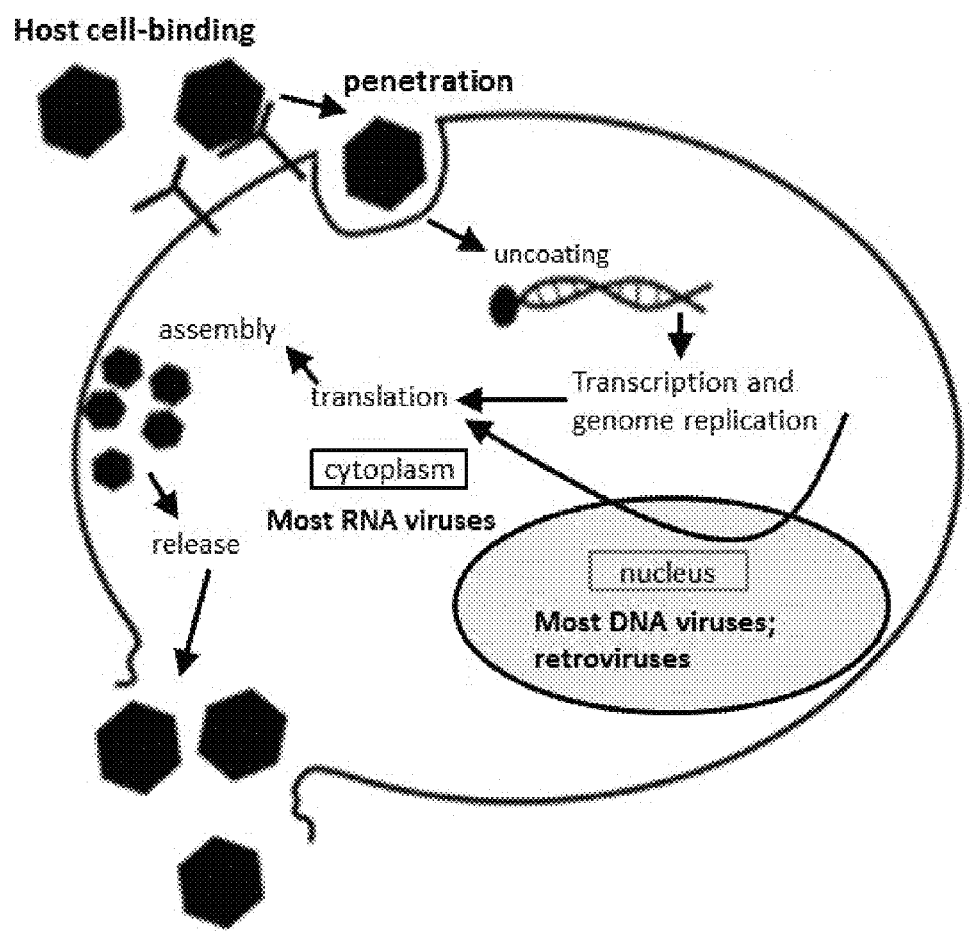
FIG. 2 illustrates a generalized model outlining steps involved in viral infection and growth (e.g. replication) in a host cell.

FIG. 2 illustrates a generalized model outlining steps involved in viral infection and growth (e.g. replication) in a host cell. In some applications the sample is from a host cell infected by a virus.

In other applications the sample can be a free or an isolated virion. The sample containing viral particles (from host cell, free or isolated) can comprise nucleic acid molecules. The nucleic acid molecules can be, e.g., DNA, RNA, mitochondrial DNA, mitochondrial RNA, genomic DNA, ribosomal DNA, chloroplast DNA or RNA, mRNA, siRNA, miRNA, cRNA, single-stranded DNA, double-stranded DNA, single-stranded RNA, double-stranded RNA, tRNA, rRNA, or cDNA.

In cases wherein the sample is an RNA sample, the RNA sample may be converted to a DNA sample by reverse transcription, often by using a reverse transcription enzyme such as reverse transcriptase. In some cases, RNA may be converted into cDNA before partitioning. In some cases, RNA may be converted into cDNA within a compartment (e.g., a droplet). In some cases, RNA may be converted into cDNA after partitioning. In some cases, the length of the resulting cDNA molecule may be made to encompass the two markers being scored on each genome. In a preferred embodiment, RNA may be converted into cDNA after partitioning RNA into one or more droplets to prevent de-linking markers that were originally physically linked. In some cases wherein RNA may be converted to cDNA after partitioning may result in an increase in fragmented molecules from artificial de-linking.

Viruses that can be used or analyzed with the present disclosure include, but are not limited to: dsDNA viruses (e.g., Adenoviruses, Herpesviruses, Poxviruses), ssDNA viruses (+ strand or "sense"), DNA (e.g., Parvoviruses), dsRNA viruses (e.g Reoviruses), (+) ssRNA viruses (+ strand or sense), RNA (e.g., Picornaviruses, Togaviruses), (−) ssRNA viruses, (− strand or antisense) RNA (e.g., Orthomyxoviruses (including influenza), Rhabdoviruses), ssRNA-RT viruses (+ strand or sense) RNA with DNA intermediate in life-cycle (e.g., Retroviruses), or dsDNA-RT viruses (e.g., Hepadnaviruses). In some preferred embodiments, HIV viruses are analyzed with the described methods. In some preferred embodiments, influenza viruses are analyzed with the described methods.

In some cases, the sample is a recombinant viral particle, particularly a recombinant viral particle isolated from a host. In some cases, the recombinant viral particle is isolated from a host that is infected by two or more viral particles with different genomes. In such case, the two or more viral particles may undergo a recombination event within the host. For example, two or more viral particles may infect the same cell and undergo reassortment or recombination of genetic information during, for example, a reaction catalyzed by reverse transcriptase. In some cases, a host is infected with a viral particle that has already undergone recombination or reassortment. The recombinant viral particle thus may be a recombinant viral particle that that is isolated after it infects a host. In some cases, the recombinant viral particle (e.g., influenza) that infects multiple hosts, including hosts of different species. In some cases, the recombinant viral particle is a recombinant viral particle that infects a host and then undergoes further recombination or reassortment within the host.

The recombinant viral particle may be isolated from infected host tissue or cells FIG. 2; in other cases, recombinant viral particles may be present in the host as a cell-free virus and may be isolated has a circulating particle from a bodily fluid such as blood, plasma, urine, mucus, etc.

Figure 8:
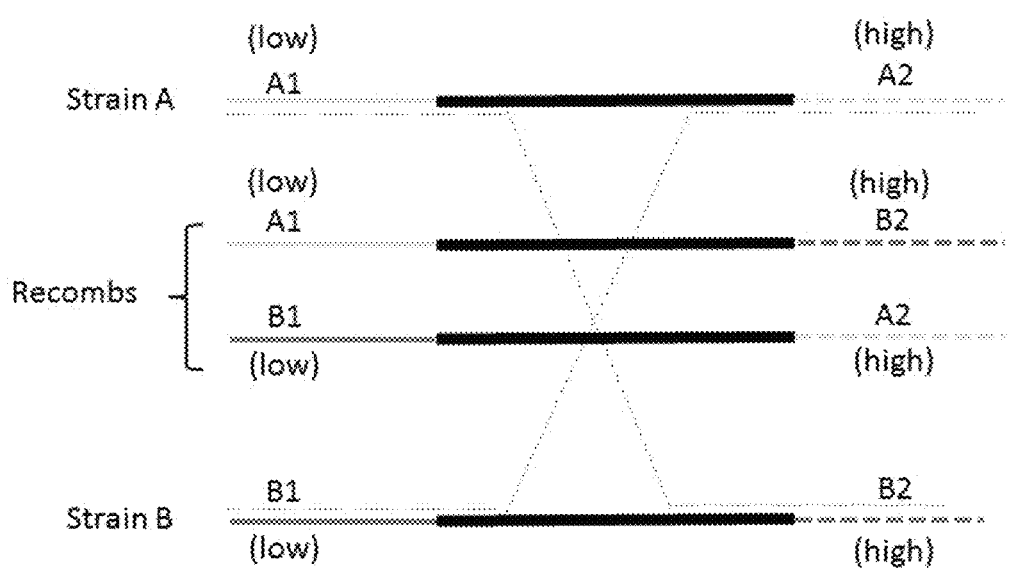
FIG. 8 is a diagram depicting recombination between two parental genomes using high and low amplitude probes of the same fluorescence marker to distinguish alternative loci of the same strain, showing Strain A, wherein A1 is labeled with low amplitude fluorescence FAM and A2 is labeled with high amplitude fluorescence FAM; and in Strain B, wherein B1 is labeled with low amplitude fluorescence HEX (or VIC) and B2 is labeled with high amplitude fluorescence HEX (or VIC).
Figure 11:
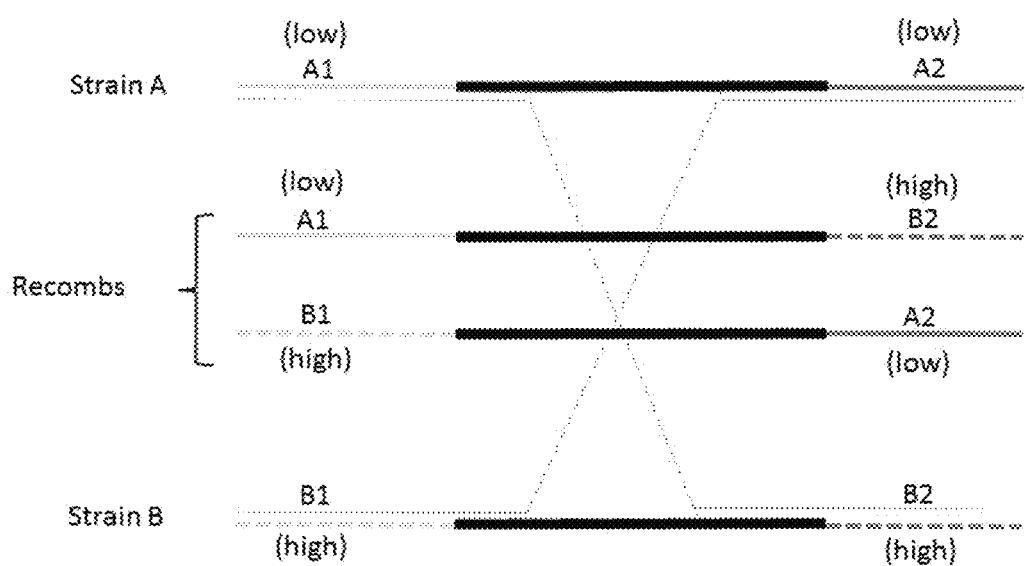
FIG. 11 is a diagram depicting recombination between two parental genomes using high and low intensity marker probes of the same color to distinguish alternative alleles of the same locus, showing Strain A, wherein A1 is labeled with FAM and A2 is labeled with HEX (or VIC); and in Strain B, wherein B1 is labeled with FAM and B2 is labeled with HEX (or VIC).

FIGS. 8 and 11 are diagrams depicting recombination between two parental genomes. Viral recombination can occur when co-infecting parent virus particles exchange genetic information (e.g., genome segments), creating a novel recombinant viral "progeny". This mechanism can cause a variety of changes in the virus including, phenotypic variations of the viral strain. Such genome alternations can produce viruses with new antigenic determinants. The appearance of an antigenically novel virus through genome alternations is called antigenic drift. Antigenically-altered viruses may be able to cause disease in previously resistant or immune hosts. These mechanisms can also cause changes in viral pathogenicity, altered host range, or altered target cell specificity but with intact antigenicity. The methods, kits and systems provide herein, provide for assaying genome alternations in a virus for antigenic drift, changes in viral pathogenicity, altered host range, altered target cell specificity, and combinations thereof. Although the FIGS. 8 and 11 mention "strains", the methods are equally applicable to any nucleic acids that undergo recombination (e.g., V(D)J recombination in immune cells).

Viral recombination can be carried out by various means such as independent assortment. Independent assortment can occur among viruses with segmented genomes. Genes that reside on different pieces of nucleic acid are randomly assorted. This can result in the generation of viruses with new antigenic determinants and new host ranges. Alternatively, recombination can occur between incompletely linked genes. Genes that reside on the same piece of nucleic acid may also undergo recombination. The methods, kits and systems provide herein, provide for assaying genome alterations by independent assortment.

Non-limiting examples of various type of recombination that can be used with the disclosure are provided herein. Recombination can occur between two different viral strains and two of the same host cell types. For example, a human influenza H1N1 strain can undergo recombination with a human influenza H2N2 strain. Recombination can occur between the same viral strains and two different host cell types. For example, a human H1N1 strain can undergo recombination with a pig H1N1 strain. Recombination can occur between two different viral strains and two different host cell types. For example, a human H1N1 strain can undergo recombination with a pig H2N2 strain. In some case, a viral particle can contain genetic information derived from at least 2, 3, 4, 5, 6, 7, 8, 9, 10, or 20 different host cell types. In some case, a viral particle can contain genetic information derived from at least 2, 3, 4, 5, 6, 7, 8, 9, 10, 15, 20, 25, 30, 40, or 50 different viral strains. In another example, retroviruses (e.g., HIV, SIV, etc.) can be recombined in various settings. For example, SIV virus may recombine with human HIV.

Examples of viruses that can be used with the methods, compositions, systems, and kits provided herein can include the following, as well as any combination thereof: *Adenovirus* (examples of species in this genus include but are not limited to, HAdV-1 to HAdV-57 in seven species *adenovirus A* to *G*), *Alfamovirus* (examples of species in this genus include but are not limited to, *Alfalfa virus 1, Alfalfa virus 2, Lucerne mosaic virus, Marmor medicaginis virus,* and *Potato calico virus*), *Allexivirus* (examples of species in this genus include but are not limited to, *Shallot virus X* and *Garlic virus*), *Allolevivirus* (examples of species in this genus include but are not limited to, *Enterobacteria phage Qbeta* and *Enterobacteria phage F1*), *Alphacryptovirus* (an example of a species in this genus includes, but is not limited to, *White clover cryptic virus 1*), *Alphalipothrixvirus* (an example of a species in this genus includes, but is not limited to, *Thermoproteus tenax virus* 1), *Alphanodoavirus, Alphapapillomavirus* (examples of species in this genus include, but are not limited to, *Human papillomavirus* 32 (HPV-32), HPV-6, HPV-7, HPV-10, HPV-16, HPV-18, HPV-26, HPV-32, HPV-61, and HPV-71), *Alpharetrovirus* (examples of species in this genus include but are not limited to, *Avian leukosis virus, Rous sarcoma virus, Avian myeloblastosis virus*, and *Fujinami sarcoma virus*), *Alphavirus* (examples of species in this genus include but are not limited to, *Sindbis virus, Semliki forest virus, Ross River virus, Chikungunya virus,* and *O'nyong-nyong virus*), *Amdovirus* (an example of a species in this genus includes, but is not limited to, *Aleutian mink disease*), *Ampelovirus* (examples of species in this genus include, but are not limited to, *Grapevine leafroll-associated virus* 3, *Grapevine leafroll-associated virus* 1, *Grapevine leafroll-associated virus* 5, *Pinapple mealybug wilt-associated virus* 1, *Pinapple mealybug wilt-associated virus* 2, and *Little cherry virus* 2), *Aphthovirus* (examples of species in this genus include, but are not limited to, *Foot-and-mouth disease virus O, Equine rhinitis A virus,* and *Bovine rhinitis B virus*), *Aquabirnavirus* (an example of a species in this genus includes, but is not limited to, *infectious pancreatic necrosis virus*), *Aquareovirus* (examples of species in this genus include, but are not limited to, *Aquareovirus A: Chum salmon reovirus CS, Aquareovirus B: Chinook salmon reovirus B, Aquareovirus C: Golden shiner reovirus, Grass carp reovirus, Aquareovirus D: Channel catfish reovirus, Aquareovirus E: Turbot reovirus, Aquareovirus F: Coho salmon reovirus SSR,* and *Aquareovirus G: American grass carp reovirus*), *Arenavirus* (examples of species in this genus include, but are not limited to, *Lymphocytic choriomeningitis virus, Lassa virus, Tacaribe virus,* and *Pichinde virus*), *Arterivirus* (examples of species in this genus include, but are not limited to, *Equine arteritis virus, Porcine reproductive* and *respiratory syndrome virus, Lactate dehydrogenase-elevating virus,* and *Simian hemorrhagic fever virus*), *Ascovirus* (examples of species in this genus include, but are not limited to, *Spodoptera frugiperda ascovirus* 1a, *Trichoplusiani ascovirus* 2a, *Heliothisvirescens ascovirus* 3c, *Diadromuspulchellus ascovirus* 4), *Asfivirus* (an example of a species in this genus includes, but is not limited to, *African swine fever virus*), *Atadenovirus* (*Ovine adenovirus D, Duck adenovirus A, Bovine adenovirus D,* and *Possum adenovirus* 1), *Aureusvirus* (an example of a species in this genus includes, but is not limited to, *Pothos latent virus*), *Avastrovirus* (an example of a species in this genus includes, but is not limited to, *Turkey astrovirus*), *Avenavirus* (an example of a species in this genus includes, but is not limited to, *Oat chlorotic stunt virus*), *Aviadenovirus* (examples of a species in this genus include, but are not limited to, *Fowl adenovirus* (*A* to *E*), and *Goose adenovirus*), *Avibirnavirus* (an example of a species in this genus includes, but is not limited to, *Infectious bursal disease virus*), *Avihepadnavirus* (an example of a species in this genus includes, but is not limited to, *Duck hepatitis B virus*), *Avipoxvirus* (examples of species in this genus include, but are not limited to, *Fowlpox virus, Canarypox virus, Pigeonpox virus, Quailpox virus,* and *Turkeypox virus*), *Avulavirus* (examples of species in this genus include, but are not limited to, *Newcastle disease virus, Avian paramyxovirus* 2, *Avian paramyxovirus* 3, and *Avian paramyxovirus* 4, *Babuvirus* (examples of species in this genus include, but are not limited to, *Banana bunchy top virus,* and *Abaca bunchy top virus*), *Badnavirus* (an example of a species in this genus includes, but is not limited to, *Commelina yellow mottle virus*), *Barnavirus* (an example of a species in this genus includes, but is not limited to, *Mushroom bacilliform virus*), *Bdellomicrovirus* (an example of a species in this genus includes, but is not limited to, *Bdellovibrio phage MAC* 1), *Begomovirus* (examples of species in this genus include, but are not limited to, *Bean golden yellow mosaic virus, Bean dwarf mosaic virus, Abutilon mosaic virus, African cassava mosaic virus, Chilli leaf curl virus, Squash leaf curl virus, Potato yellow mosaic virus,* and *Tomato yellow leaf curl virus*), *Betacryptovirus* (an example of a species in this genus includes, but is not limited to, *White clover cryptic virus* 2), *Betalipothrixvirus* (example of species in this genus include, but are not limited to, *Sulfolobus islandicus filamentous virus,* and *Acidianus filamentous virus* 3), *Betapapillomavirus* (examples of species in this genus include, but are not limited to, *Human papillomavirus* 5 (HPV-5), HPV-9, and HPV-49), *Betanodovirus, Betaretrovirus* (examples of species in this genus include, but are not limited to, *Mouse mammary tumor virus, Jaagsiekte sheep retrovirus,* and *Squirrel monkey retrovirus*), *Betatetravirus* (examples of species in this genus include, but are not limited to, *Nudaurelia capensis beta virus, Antheraea eucalypti virus, Darna trima virus, Dasychirapudibunda virus, Pseudoplusia includes virus,* and *Trichoplusiani virus*), *Bocavirus* (examples of species in this genus include, but are not limited to, *Bovine parvovirus, Human bocavirus,* and *Canine minute virus*), *Bornavirus* (examples of species in this genus include, but are not limited to, *Borna disease virus* and *Avian Bornavirus*), *Bracovirus* (an example of a species in this genus includes, but is not limited to, *Cotesia melanoscela bracovirus*), *Brevidensovirus* (examples of species in this genus include, but are not limited to, *Aedes aegypti densovirus,* and *Aedes albopictus densovirus* (AalDNV), *Bromovirus* (an example of a species in this genus includes, but is not limited to, *Brome mosaic virus*), *Bymovirus* (examples of species in this genus include, but are not limited to, *Barley yellow mosaic virus, Barley mild mosaic virus, Oat mosaic virus,* and *Rice necrosis mosaic virus*). *Capillovirus* (examples of species in this genus include, but are not limited to, *Apple stem grooving virus, Chemy virus A,* and *Lilac chlorotic leafspot virus*), *Capripoxvirus* (examples of species in this genus include, but are not limited to, *Sheeppox virus, Goatpox virus,* and *Lumpy skin disease virus*), *Cardiovirus* (examples of species in this genus include, but are not limited to, *Encephalomyocarditis virus,* and *Theilovirus*), *Carlavirus* (examples of species in this genus include, but are not limited to, *Carnation latent virus, Garlic common latent virus, Lily symptomless virusm, Potato virus M,* and *Shallot latent virus*), *Carmovirus* (an example of a species in this genus includes, but is not limited to, *Carnation mottle virus*), *Caulimovirus* (an example of a species in this genus includes, but is not limited to, *Cauliflower mosaic virus*), *Cavemovirus* (an example of a species in this genus includes, but is not limited to, *Cassava mosaic virus*), *Chlamydiamicrovirus* (an example of a species in this genus includes, but is not limited to, *Chlamydia phage* 1), *Chlorovirus* (examples of species in this genus include, but are not limited to, *Paramecium bursaria,* and *Chlorella virus*), *Chloriridovirus* (an example of a species in this genus includes, but is not limited to, *Invertebrate iridescent virus* 3), *Chrysovirus* (an example of a species in this genus includes, but is not limited to, *Penicillium chrysogenum virus*), *Circovirus* (examples of species in this genus include, but are not limited to, *Porcine circovirus* 1, *Porcine circovirus* 2, *Pigeon circovirus,* and *Swan circovirus*), *Closterovirus* (examples of species in this genus include, but are not limited to, *Beet yellows virus, Citrus tristeza virus,* and

*Grapevine leafroll-associated virus* 2), *Coccolithovirus* (an example of a species in this genus includes, but is not limited to, *Emiliania huxleyi virus* 86), *Coltivirus* (examples of species in this genus include, but are not limited to, *Colorado tick fever virus*, and *European eyach virus*), *Comovirus* (examples of species in this genus include, but are not limited to, *Cowpea mosaic virus, Bean pod mottle virus, Cowpea severe mosaic virus, Red clover mottle virus,* and *Squash mosaic virus*), *Coronavirus, Corticovirus* (an example of a species in this genus includes, but is not limited to, *Pseudoalteromonas phage PM2*), *Cripavirus* (an example of a species in this genus includes, but is not limited to, *Cricket paralysis virus*), *Cucumovirus* (examples of species in this genus include, but are not limited to, *Cucumber moasic virus, Peanut stunt virus,* and *Tomato aspermy virus*), *Curtovirus* (examples of species in this genus include, but are not limited to, *Beet curly top virus, Beet mild curly top virus, Beet severe curly top virus,* and *Horseradish curly top virus*), *Cypovirus* (an example of a species in this genus includes, but is not limited to, *Cypovirus* 1), *Cystovirus* (examples of species in this genus include, but are not limited to, *Pseudomonas phage Phi6,* and *Pseudomonas phage Phi7* to *Phi14*), *Cytomegalovirus,* (examples of species in this genus include, but are not limited to, *Human cytomegalovirus, Cercopithecine herpesvirus* 5, *Cercopithecine herpesvirus* 8, and *Pongine herpesvirus* 4), *Cytorhabdovirus* (examples of species in this genus include, but are not limited to, *Lettuce necrotic yellows virus,* and *Northern cereal mosaic virus*), *Dainthovirus, Deltapapillomavirus* (examples of species in this genus include, but are not limited to, *European elk papillomavirus, Bovine papillomavirus type* 1, *Bovine papillomavirus type* 2, and *Deer papillomavirus*), *Deltaretrovirus* (examples of species in this genus include, but are not limited to, *Bovine leukemia virus, Human T-lymphotropic virus, Human T-lymphotropic virus* 2, *Human T-lymphotropic virus* 3, and *Simian T-lymphotropic virus* 1), *Deltavirus* (an example of a species in this genus includes, but is not limited to, *Hepatitis D virus*), *Densovirus, Dependovirus* (examples of species in this genus include, but are not limited to, *Adeno-associated virus-2, Adeno-associated virus-1,* and *Duck parvovirus*), *Ebolavirus* (examples of species in this genus include, but are not limited to, *Zaire ebolavirus, Reston ebolavirus,* and *Sudan ebolavirus*), *Enamovirus* (an example of species in this genus includes, but is not limited to, *Peaenation mosaic virus-1*), *Enterovirus* (examples of species in this genus include, but are not limited to, *Poliovirus (Human enterovirus C serotypes PV-1, PV-2, PV-3), Human coxsackievirus, Human enterovirus* 70, and *Human rhinovirus A*), *Entomobirnavirus* (an example of species in this genus includes, but is not limited to, *Drosophila X virus*), *Entomopoxvirus A, Entomopoxvirus B, Entomopoxvirus C, Ephemerovirus* (examples of species in this genus include, but are not limited to, *Bovine ephemeral fever virus* and *Berrimah virus*), *Epsilonpapillomavirus* (an example of a species in this genus includes, but is not limited to, *Bovine papillomavirus* 5), *Epsilonretrovirus* (an example of a species in this genus includes, but is not limited to, *Walleye dermal sarcoma virus*), *Erbovirus* (examples of species in this genus include, but are not limited to, *Equine rhinitis B virus* 1, and *Equine rhinitis B virus* 2), *Errantivirus, Erythrovirus* (examples of species in this genus include, but are not limited to, *Human parvovirus B19,* and *Simian parvovirus*), *Etapapillomavirus, Fabavirus* (examples of species in this genus include, but are not limited to, *Broad bean wilt virus* 1, *Broad bean wilt virus* 2, and *Lamium mild mosaic virus*), *Fijivirus* (examples of species in this genus include, but are not limited to, *Fiji disease virus, Maize rough dwarf virus, Mal de Rio Cuarto virus, Rice black streaked dwarf virus, Oat sterile dwarf virus, Nilaparvata lugens reovirus,* and *Pangola stunt virus*), *Flavivirus* (examples of species in this genus include, but are not limited to, *Yellow fever virus, Japanese encephalitis virus, Tick-borne encephalitis virus, West Nile virus, St. louis encephalitis virus,* and *Murray valley encephalitis virus*), *Foveavirus* (examples of species in this genus include, but are not limited to, *Apple stem pitting virus, Apricot latent virus,* and *Rupestris steem pitting-associated virus*), *Fusellovirus, Gammalipothrixvirus* (an example of species in this genus includes, but is not limited to, *Acidianus filamentous virus* 1), *Gammapapillomavirus* (examples of species in this genus include, but are not limited to, *Human papillomavirus* 4 (HPV-4), HPV-48-HPV-50, HPV-60, and HPV-88), *Gammaretrovirus* (examples of species in this genus include, but are not limited to, *Murine leukemia virus, Feline leukemia virus, Gibbon ape leukemia virus,* and *Xenotropic murine leukemia virus-related virus*), *Giardiavirus* (an example of a species in this genus includes, but is not limited to, *Giardia lamblia virus*), *Granulovirus, Guttavirus* (an example of a species in this genus includes, but is not limited to, *Sulfolobus newzealandicus droplet-shaped virus*), *Gyrovirus* (an example of a species in this genus includes, but is not limited to, *Chicken anemia virus*), *Hantavirus* (examples of species in this genus include, but are not limited to, *Hantaan virus, New York virus, Puumala virus, Sin nombre virus,* and *Tula virus*), *Hemivirus, Henipavirus* (examples of species in this genus include, but are not limited to, *Hendra virus,* and *Nipah virus*), *Hepacivirus* (an example of a species in this genus includes, but is not limited to, *Hepatitis C virus*), *Hepadnavirus, Hepatovirus* (examples of species in this genus include, but are not limited to, *Hepatitis A virus, Human hepatitis A virus,* and *Simian hepatitis A virus*), *Hypovirus* (examples of species in this genus include, but are not limited to, *Cryphonectria hypovirus* 1, *Cryphonectria hypovirus* 2, *Cryphonectria hypovirus* 3, and *Cryphonectria hypovirus* 4), *Ichnovirus* (an example of a species in this genus includes, but is not limited to, *Campoletis sonorensis ichnovirus*), *Ictalurivirus* (an example of a species in this genus includes, but is not limited to, *Ictalurid herpesvirus* 1), *Idnoreovirus* (examples of species in this genus include, but are not limited to, *Idnoreovirus* 1: *Diadromus pulchellus idnoreovirus* 1, *Idnoreovirus* 2: *Hyposoter exiguae idnoreovirus* 2, *Idnoreovirus* 3: *Musca domestica idnoreovirus* 3, *Idnoreovirus* 4: *Dacus oleae idnoreovirus* 4, *Idnoreovirus* 5: *Ceratitis capitata idnoreovirus* 5, and *Drosophila melanogaster idnoreovirus-5*), *Ilarvirus* (an example of a species in this genus includes, but is not limited to, *Tobacco streak virus*), *Iltovirus* (examples of species in this genus include, but are not limited to, *Gallid herpesvirus* 1 and *Psittacid herpesvirus* 1, *Influenza A virus* (an example of a species in this genus includes, but is not limited to, H1N1, H2N2, H3N2, H5N1, H7N7, H1N2, H9N2, H7N2, H7N3, H10N7, and H7N9. *Influenza A/Puerto Rico/8/34* H1N1 (FLUAV), *Influenza B virus* (an example of a species in this genus includes, but is not limited to, *Influenza B/Lee/1940* (FLUBV), *Influenza C virus* (an example of a species in this genus includes, but is not limited to, *Influenza C/California/78* (FLUCV), *Inovirus* (examples of species in this genus include, but are not limited to, *Enterobacteria phage M13,* and *Pseudomonas phage Pf1*), *Iotapapillomavirus* (an example of a species in this genus includes, but is not limited to, *Mastomys natalensis papillomavirus*), *Ipomovirus* (examples of species in this genus include, but are not limited to, *Sweet potato mild mottle* virus, and *Cucumber vein yellowing virus*), *Iridovirus*, *Isavirus* (an example of a species in this genus includes, but is not limited to, *Infectious salmon anemia virus*), *Iteravirus* (examples of species in this genus include, but are not limited to, *Bombyx mori densovirus* 5, *Bombyx mori densovirus* 1, and *Casphalia extranea densovirus*), *Kappapapillomavirus* (examples of species in this genus include, but are not limited to, *Cottontail rabbit papillomavirus*, and *Rabbit oral papillomavirus*), *Kobuvirus* (examples of species in this genus include, but are not limited to, *Aichi virus*, and *Bovine kobuvirus*), *Lagovirus* (an example of a species in this genus includes, but is not limited to, *Rabbit hemorrhagic disease virus*), *Lambdapapillomavirus* (an example of a species in this genus includes, but is not limited to, *Canine oral papillomavirus*), *Leishmaniavirus* (examples of species in this genus include, but are not limited to, *Leishmania RNA virus* 1-1 (LRV-1-1) to (LRV-1-12), and *Leishmania RNA virus b2-1*), *Lentivirus* (examples of species in this genus include, but are not limited to, *Human immunodeficiency virus* 1 (HIV-1), HIV-2, *Simian immunodeficiency virus*, *Bovine immunodeficiency virus*, and *Feline immunodeficiency virus*), *Leporipoxvirus* (examples of species in this genus include, but are not limited to, *Myxoma virus*, *Hare fibroma virus*, *Rabbit fibroma virus*, and *Squirrel fibroma virus*), *Levivirus* (examples of species in this genus include, but are not limited to, *Enterobacteria phage MS2*, *Enterobacteria phage BZ13*, *Enterobacteria phage*, and *Enterobacteria phage MS2*), *Luteovirus* (examples of species in this genus include, but are not limited to, *Barley yellow dwarf virus-PAV*, *Barley yellow dwarf virus-MAV*, *Barley yellow dwarf virus-PAS*, *Bean leafroll virus*, and *Soybean dwarf virus*), *Lymphocryptovirus* (examples of species in this genus include, but are not limited to, *Human herpesvirus* 4 (*Epstein-Barr virus*), *Cercopithecine herpesvirus* 12, *Cercopithecine herpesvirus* 14, *Cercopithecine herpesvirus* 15, *Pongine herpesvirus* 1, *Pongine herpesvirus* 2, and *Pongine herpesvirus* 3), *Lymphocystivirus* (an example of a species in this genus includes, but is not limited to, *Lymphocystis disease virus* 1), *Lyssavirus* (examples of species in this genus include, but are not limited to, *Rabies virus*, *Mokola virus*, and *Duvenhage virus*), *Machlomovirus* (an example of a species in this genus includes, but is not limited to, *Maize chlorotic mottle virus*), *Macluravirus* (an example of a species in this genus includes, but is not limited to, *Maclura mosaic virus*), *Maculavirus* (an example of a species in this genus includes, but is not limited to, *Grapevine fleck virus*), *Mamastrovirus* (examples of species in this genus include, but are not limited to, *Human astrovirus*, *Bovine astrovirus*, *Feline astrovirus*, *Mink astrovirus*, *Ovine astrovirus*, and *Porcine astrovirus*), *Mandarivirus* (an example of a species in this genus includes, but is not limited to, *Indian citrus ringspot virus*), *Marafivirus* (examples of species in this genus include, but are not limited to, *Maize rayado fino virus*, *Oat blue dwarf virus*, and *Bermuda grass etched-line virus*), *Marburgvirus* (an example of a species in this genus includes, but is not limited to, *Lake Victoria marburgvirus*), *Mardivirus* (examples of species in this genus include, but are not limited to, *Gallid herpesvirus* 2, *Gallid herpesvirus* 3, and *Meleagrid herpesvirus* 1), *Marnavirus* (examples of species in this genus include, but are not limited to, *Heterosigma akashiwo RNA virus*, *Schizochytrium single-stranded RNA virus*, *Marine RNA virus JP-A*, and *Marine RNA virus JP-B*), *Mastadenovirus* (examples of species in this genus include, but are not limited to, *Human adenovirus C*, *Human adenovirus A*, *Human adenovirus B*, *Human adenovirus D*, *Human adenovirus E*, and *Human adenovirus F*), *Mastrevirus* (examples of species in this genus include, but are not limited to, *Maize streak virus*, *Bean yellow dwarf virus*, *Chloris striate mosaic virus*, *Digitaria streak virus*, *Miscanthus streak virus*, *Tobacco yellow dwarf virus*, and *Wheat dwarf virus*), *Megalocytivirus* (an example of a species in this genus includes, but is not limited to, *infectious spleen* and *kidney Necrosis virus*), *Metapneumovirus* (examples of species in this genus include, but are not limited to, *Avian metapneumovirus*, and *Human metapneumovirus*), *Metavirus*, *Microvirus* (an example of a species in this genus includes, but is not limited to, *Enterobacteria phage PhiX174*), *Mitovirus* (examples of species in this genus include, but are not limited to, *Cryphonectria mitovirus* 1, and *Ophiostoma mitovirus 3A*), *Molluscipoxvirus* (an example of a species in this genus includes, but is not limited to, *Molluscum contagiosum virus*), *Morbillivirus* (examples of species in this genus include, but are not limited to, *Measles virus*, *Rinderpest Virus*, *Canine distemper virus*, *Peste des petits ruminants virus*), *Mupapillomavirus* (an example of a species in this genus includes, but is not limited to, *Human papillomavirus* 1), *Muromegalovirus* (examples of species in this genus include, but are not limited to, *Murine herpesvirus* 1 and *Murine herpesvirus* 2), *Mycoreovirus* (examples of species in this genus include, but are not limited to, *mycoreovirus* 1: *Cryphonectria parasitica mycoreovirus*-1, and *mycoreovirus* 3: *Rosellinia necatrix mycoreovirus*-3), *sNairovirus* (examples of species in this genus include, but are not limited to, *Dugbe virus*, and *Crimean-Congo hemorrhagic fever virus*), *Nanovirus* (examples of species in this genus include, but are not limited to, *Subterranean clover stunt virus*, *Faba bean necrotic yellows virus*, and *Milk vetch dwarf virus*), *Narnavirus* (examples of species in this genus include, but are not limited to, *Saccharomyces cerevisiae narnavirus 20S*, and *Saccharomyces 23S RNA narnavirus*), *Necrovirus* (an example of a species in this genus includes, but is not limited to, *Tobacco necrosis virus*), *Nepovirus* (examples of species in this genus include, but are not limited to, *Tobacco ringspot virus*, *Grapevine fanleaf virus*, *Beet ringspot virus*, and *Blackcurrant reversion virus*), *Norovirus* (examples of species in this genus include, but are not limited to, *Norwalk virus*, *Lordsdale virus*, and *Southampton virus*), *Novirhabdovirus* (examples of species in this genus include, but are not limited to, *Infectious hematopoietic necrosis virus*, and *Snakehead virus*), *Nucleopolyhedrovirus*, *Nucleorhabdovirus* (examples of species in this genus include, but are not limited to, *Potato yellow dwarf virus*, and *Maize mosaic virus*), *Nupapillomavirus* (an example of a species in this genus includes, but is not limited to, *Human papillomavirus* 41), *Okavirus* (examples of species in this genus include, but are not limited to, *Gill-associated virus*, and *Yellow head virus*), *Oleavirus* (an example of a species in this genus includes, but is not limited to, *Olive latent virus* 2), *Omegatetravirus* (examples of species in this genus include, but are not limited to, *Nudaurelia capensis omega virus*, *Helicoverpa armigera stunt virus*, and *Dendrolimus punctatus virus*), *Omikronpapillomavirus* (an example of a species in this genus includes, but is not limited to, *Phocoena spinipinnis papillomavirus*), *Orbivirus* (an example of a species in this genus includes, but is not limited to, *Bluetongue virus*, and *African horse sickness virus*, and *Epizootic hemorrhagic disease virus*), *Orthobunyavirus* (examples of species in this genus include, but are not limited to, *Bunyamwera virus*, *La Crosse virus*, and *Schmallenberg virus*), *Orthohepadnavirus* (an example of a species in this genus includes, but is not limited to, *Hepatitis B virus*), *Orthopoxvirus* (examples of species in this genus include, but are not limited to, *Vaccinia virus*, *Cowpox virus*, *Horsepox virus*, *Monkeypox virus*, and

*Variola virus*), *Orthoreovirus* (examples of species in this genus include, but are not limited to, *Mammalian orthoreovirus, Avian orthoreovirus, Nelson Bay orthoreovirus, Baboon orthoreovirus,* and *Reptilian orthoreovirus*), *Oryzavirus* (examples of species in this genus include, but are not limited to, *Rice ragged stunt virus,* and *Echinochloa ragged stunt virus*), *Panicovirus* (an examples of a species in this genus includes, but is not limited to, *Panicum mosaic virus*), *Parapoxvirus* (examples of species in this genus include, but are not limited to, *Orf virus, Bovine papular stomatitis virus, Pseudocowpox virus,* and *Squirrel parapoxvirus*), *Parechovirus* (examples of species in this genus include, but are not limited to, *Human parechovirus* 1 (formerly *echovirus* 22), *Human parechovirus* 2 (HPeV-2) (formerly *echovirus* 23), *Human parechovirus* 3 (HPeV-3), and *Ljungan virus*), *Partitivirus* (an examples of species in this genus includes, but is not limited to, *Atkinsonella Hypoxylon virus*), *Parvovirus* (examples of species in this genus include, but are not limited to, *Minute virus of mice, Canine parvovirus, Chicken parvovirus, Mouse parvovirus* 1, and *LuIII virus*), *Pefudensovirus* (examples of species in this genus include, but are not limited to, *Periplaneta fuliginosa densovirus,* and *Acheta domesticus densovirus*), *Pestivirus* (examples of species in this genus include, but are not limited to, *Bovine diarrhea virus* 1, *Bovine diarrhea virus* 2, *Border disease virus,* and *Classical swine fever virus*), *Petuvirus* (an example of a species in this genus includes, but is not limited to, *Petunia vein clearing virus*), *Phaeovirus* (an example of a species in this genus includes, but is not limited to, *Ectocarpus siliculosus virus* 1), *Phlebovirus* (examples of species in this genus include, but are not limited to, *Rift valley fever virus, Uukuniemi virus,* and *Punta toro phlebovirus*), *Phytoreovirus* (examples of species in this genus include, but are not limited to, *Wound tumor virus, Rice dwarf virus, Rice gall dwarf virus,* and *Tobacco leaf enation phytoreovirus*), *Pipapillomavirus* (examples of species in this genus include, but are not limited to, *Hamster oral papillomavirus,* and *Rattus norvegicus papillomavirus* 1), *Plasmavirus* (an example of a species in this genus includes, but is not limited to, *Acholeplasma phage L2*), *Plectrovi* (an example of a species in this genus includes, but is not limited to, *Acholeplasma phage L51*), *Pneumovirus* (examples of species in this genus include, but are not limited to, *Human respiratory syncytial virus,* and *Bovine respiratory syncytial virus*), *Polerovirus* (examples of species in this genus include, but are not limited to, *Potato leafroll virus, Beet western yellows virus,* and *Cereal yellow dwarf virus*), *Polyomavirus* (examples of species in this genus include, but are not limited to, *Simian virus* 40, *BK polyomavirus, Merkel cell polyomavirus, Budgerigar fledgling disease polyomavirus, Bovine polyomavirus, JC polyomavirus,* and *Murine polyomavirus*), *Potexvirus* (examples of species in this genus include, but are not limited to, *Potato virus X, Clover yellow mosaic virus,* and *Cymbidium mosaic virus*), *Potyvirus* (examples of species in this genus include, but are not limited to, *Potato virus Y, Beet mosaic virus, Clover yellow vein virus, Plum pox virus, Potato virus A,* and *Tobaccovein mottling virus*), *Prasinovirus* (an example of a species in this genus includes, but is not limited to, *Micromonas pusilla virus SP1*), *Prymnesiovirus* (an example of a species in this genus includes, but is not limited to, *Chrysochromulina brevifilum virus PW1*), *Pseudovirus, Ranavirus* (an example of a species in this genus includes, but is not limited to, *Frog virus* 3), *Raphidovirus* (an example of a species in this genus includes, but is not limited to, *Heterosigma akashiwo virus 01*), *Respirovirus* (examples of species in this genus include, but are not limited to, *Sendai virus,* and *Simian virus* 10), *Rhadinovirus* (examples of species in this genus include, but are not limited to, *Saimiriine herpesvirus* 2, *Kaposi's sarcoma-associated herpesvirus, Bovine herpesvirus* 4, *Equid herpesvirus* 2, and *Murid herpesvirus* 4), *Rhinovirus, Roseolovirus* (examples of species in this genus include, but are not limited to, *Human herpesvirus 6A, Human herpesvirus* 7, and *Human herpesvirus 6B*), *Rotavirus* (examples of species in this genus include, but are not limited to, *Rotavirus A* to *Rotavirus G*), *Rubivirus* (an example of a species in this genus includes, but is not limited to, *Rubella virus*), *Rubulavirus* (examples of species in this genus include, but are not limited to, *Mumps virus,* and *Mapuera virus*), *Rudivirus* (examples of species in this genus include, but are not limited to, *Sulfolobus islandicus rod-shaped virus* 1, and *Sulfolobus islandicus rod-shaped virus* 2), *Rymovirus* (an example of a species in this genus includes, but is not limited to, *Ryegrass mosaic virus*), *Sapovirus* (an example of a species in this genus includes, but is not limited to, *Sapporo virus*), *Seadornavirus* (examples of species in this genus include, but are not limited to, *Banna virus, Kadipiro virus,* and *Liao ning virus*), *Sequivirus* (examples of species in this genus include, but are not limited to, *Parsnip yellow fleck virus, Dandelion yellow mosaic sequivirus,* and *Lettuce mottle virus*), *Siadenovirus* (examples of species in this genus include, but are not limited to, *Frog adenovirus,* and *Turkey adenovirus A*), *Simplexvirus* (examples of species in this genus include, but are not limited to, *Human herpesvirus* 1, *Human herpesvirus* 2, and *Bovine herpesvirus* 2), *Soymovirus* (examples of species in this genus include, but are not limited to, *Soybean chlorotic mottle virus, Blueberry red ringspot virus,* and *Peanut chlorotic streak virus*), *Spiromicrovirus* (an example of a species in this genus includes, but is not limited to, *Spiroplasma phage* 4), *Spumavirus* (examples of species in this genus include, but are not limited to, *Simian foamy virus, Bovine foamy virus,* and *Feline foamy virus*), *Suipoxvirus* (an example of a species in this genus includes, but is not limited to, *Swinepox virus*), *Tectivirus* (examples of species in this genus include, but are not limited to, *Enterobacteria phage PRD1, Bacillus phage AP50, Bacillus phage Bam35,* and *Thermus phage P17-14*), *Teschovirus* (examples of species in this genus include, but are not limited to, *Porcine teschovirus* 1 (PTV-1) to PTV-11), *Thetapapillomavirus* (an example of a species in this genus includes, but is not limited to, *Psittacus erithacus timneh papillomavirus*), *Thogotovirus* (examples of species in this genus include, but are not limited to, *Thogoto virus,* and *Dhori virus*), *Tombusvirus* (examples of species in this genus include, but are not limited to, *Tomato bushy stunt virus,* and *Carnation Italian ringspot virus*), *Topocuvirus* (an example of a species in this genus includes, but is not limited to, *Tomato pseudo-curly top virus*), *Torovirus* (examples of species in this genus include, but are not limited to, *Equine Torovirus, Human torovirus,* and *Breda virus*), *Tospovirus* (an example of a species in this genus includes, but is not limited to, *Tomato spotted wilt virus*), *Totivirus* (examples of species in this genus include, but are not limited to, *Saccharomyces cerevisiae virus L-A, Saccharomyces cerevisiae virus L-BC,* and *Ustilago maydis virus H1*), *Trichovirus* (examples of species in this genus include, but are not limited to, *Apple chlorotic leaf spot virus, Chemy mottle leaf virus, Grapevine berry inner necrosis virus,* and *Peach mosaic virus*), *Tritimovirus* (an example of a species in this genus includes, but is not limited to, *Wheat streak mosaic virus*), *Tungrovirus* (an example of a species in this genus includes, but is not limited to, *Rice tungro bacilliform virus*), *Tymovirus* (examples of species in this genus include, but are not limited to, *Turnip yellow mosaic virus*, *Andean potato latent virus*, *Belladonna mottle virus*, and *Cacao yellow mosaic virus*), *Varicellovirus* (examples of species in this genus include, but are not limited to, *Human herpesvirus 3* (*Varicella-zoster virus*), *Bovine herpesvirus 1*, *Bovine herpesvirus 5*, and *Suid herpesvirus 1*), *Vesiculovirus* (examples of species in this genus include, but are not limited to, *Vesicular stomatitis*, *Indiana virus*, *Cocal virus*, *Maraba virus*, and *Piry virus*), *Vesivirus* (an example of a species in this genus includes, but is not limited to, *Vesicular exanthema of swine virus*), *Vitivirus*, (examples of species in this genus include, but are not limited to, *Grapevine virus A*, *Grapevine virus B*, *Grapevine virus D*, and *Heracleum latent virus*), *Waikavirus* (examples of species in this genus include, but are not limited to, *Rice tungro spherical virus*, and *Maize chlorotic dwarf virus*), *Whispovirus* (examples of species in this genus include, but are not limited to, *White spot syndrome virus 1*), *Xipapillomavirus* (examples of species in this genus include, but are not limited to, *Bovine papillomavirus 3*, *Bovine papillomavirus 4*, and *Bovine papillomavirus 6*) *Yatapoxvirus* (examples of species in this genus include, but are not limited to, *Yaba monkey tumor virus*, and *Tanapox virus*) or *Zetapapillomavirus* (an example of a species in this genus includes, but is not limited to, *Equine papillomavirus 1*).

Non-limiting examples of recombination of two different viruses that can be used with methods provided herein include, but are not limited to recombination within a strain, between at least two different stains, within a species, between at least two different species, within a subspecies, between at least two different subspecies, within a family, between at least two different families, within a genera, or between at least two different genera. Non-limiting examples of recombination between at least two genera can include, for example recombination between: *Influenza* and *Alfamovirus*, *Influenza* and *Allexivirus*, *Influenza* and *Allolevivirus*, *Influenza* and *Alphacryptovirus*, *Influenza* and *Alphalipothrixvirus*, *Influenza* and *Alphanodoavirus*, *Influenza* and *Alphapapillomavirus*, *Influenza* and *Alpharetrovirus*, *Influenza* and *Alphavirus*, *Influenza* and *Amdovirus*, *Influenza* and *Ampelovirus*, *Influenza* and *Aphthovirus*, *Influenza* and *Aquabirnavirus*, *Influenza* and *Aquareovirus*, *Influenza* and *Arenavirus*, *Influenza* and *Arterivirus*, *Influenza* and *Ascovirus*, *Influenza* and *Asfivirus*, *Influenza* and *Atadenovirus*, *Influenza* and *Aureusvirus*, *Influenza* and *Avastrovirus*, *Influenza* and *Avenavirus*, *Influenza* and *Aviadenovirus*, *Influenza* and *Avibirnavirus*, *Influenza* and *Avihepadnavirus*, *Influenza* and *Avipoxvirus*, *Influenza* and *Avulavirus*, *Influenza* and *Babuvirus*, *Influenza* and *Badnavirus*, *Influenza* and *Barnavirus*, *Influenza* and *Bdellomicrovirus*, *Influenza* and *Begomovirus*, *Influenza* and *Betacryptovirus*, *Influenza* and *Betalipothrixvirus*, *Influenza* and *Betanodovirus*, *Influenza* and *Betapapillomavirus*, *Influenza* and *Betaretrovirus*, *Influenza* and *Betatetravirus*, *Influenza* and *Bocavirus*, *Influenza* and *Bornavirus*, *Influenza* and *Bracovirus*, *Influenza* and *Brevidensovirus*, *Influenza* and *Bromovirus*, *Influenza* and *Bymovirus*, *Influenza* and *Capillovirus*, *Influenza* and *Capripoxvirus*, *Influenza* and *Cardiovirus*, *Influenza* and *Carlavirus*, *Influenza* and *Carmovirus*, *Influenza* and *Caulimovirus*, *Influenza* and *Cavemovirus*, *Influenza* and *Chlamydiamicrovirus*, *Influenza* and *Chlorovirus*, *Influenza* and *Chloriridovirus*, *Influenza* and *Chrysovirus*, *Influenza* and *Circovirus*, *Influenza* and *Closterovirus*, *Influenza* and *Coccolithovirus*, *Influenza* and *Coltivirus*, *Influenza* and *Comovirus*, *Influenza* and *Coronavirus*, *Influenza* and *Corticovirus*, *Influenza* and *Cripavirus*, *Influenza* and *Cucumovirus*, *Influenza* and *Curtovirus*, *Influenza* and *Cypovirus*, *Influenza* and *Cystovirus*, *Influenza* and *Cytomegalovirus*, *Influenza* and *Cytorhabdovirus*, *Influenza* and *Dainthovirus*, *Influenza* and *Deltapapillomavirus*, *Influenza* and *Deltaretrovirus*, *Influenza* and *Deltavirus*, *Influenza* and *Densovirus*, *Influenza* and *Dependovirus*, *Influenza* and *Ebolavirus*, *Influenza* and *Enamovirus*, *Influenza* and *Enterovirus*, *Influenza* and *Entomobimavirus*, *Influenza* and *Entomopoxvirus A*, *Influenza* and *Entomopoxvirus B*, *Influenza* and *Entomopoxvirus C*, *Influenza* and *Ephemerovirus*, *Influenza* and *Epsilonpapillomavirus*, *Influenza* and *Epsilonretrovirus*, *Influenza* and *Erbovirus*, *Influenza* and *Errantivirus*, *Influenza* and *Erythrovirus*, *Influenza* and *Etapapillomavirus*, *Influenza* and *Fabavirus*, *Influenza* and *Fijivirus*, *Influenza* and *Flavivirus*, *Influenza* and *Foveavirus*, *Influenza* and *Fusellovirus*, *Influenza* and *Gammalipothrixvirus*, *Influenza* and *Gammapapillomavirus*, *Influenza* and *Gammaretrovirus*, *Influenza* and *Giardiavirus*, *Influenza* and *Granulovirus*, *Influenza* and *Guttavirus*, *Influenza* and *Gyrovirus*, *Influenza* and *Hantavirus*, *Influenza* and *Hemivirus*, *Influenza* and *Henipavirus*, *Influenza* and *Hepacivirus*, *Influenza* and *hepadnavirus*, *Influenza* and *Hepatovirus*, *Influenza* and *Hypovirus*, *Influenza* and *Ichnovirus*, *Influenza* and *Ictalurivirus*, *Influenza* and *Idnoreovirus*, *Influenza* and *Ilarvirus*, *Influenza* and *Iltovirus*, *Influenza* and *Influenza A virus*, *Influenza* and *Influenza B virus*, *Influenza* and *Influenza C virus*, *Influenza* and *Inovirus*, *Influenza* and *Iotapapillomavirus*, *Influenza* and *Ipomovirus*, *Influenza* and *Iridovirus*, *Influenza* and *Isavirus*, *Influenza* and *Iteravirus*, *Influenza* and *Kappapapillomavirus*, *Influenza* and *Kobuvirus*, *Influenza* and *Lagovirus*, *Influenza* and *Lambdapapillomavirus*, *Influenza* and *Leishmaniavirus*, *Influenza* and *Lentivirus*, *Influenza* and *Leporipoxvirus*, *Influenza* and *Levivirus*, *Influenza* and *Luteovirus*, *Influenza* and *Lymphocryptovirus*, *Influenza* and *Lymphocystivirus*, *Influenza* and *Lyssavirus*, *Influenza* and *Machlomovirus*, *Influenza* and *Macluravirus*, *Influenza* and *Maculavirus*, *Influenza* and *Mamastrovirus*, *Influenza* and *Mandarivirus*, *Influenza* and *Marafivirus*, *Influenza* and *Marburgvirus*, *Influenza* and *Mardivirus*, *Influenza* and *Marnavirus*, *Influenza* and *Mastadenovirus*, *Influenza* and *Mastrevirus*, *Influenza* and *Megalocytivirus*, *Influenza* and *Metapneumovirus*, *Influenza* and *Metavirus*, *Influenza* and *Microvirus*, *Influenza* and *Mitovirus*, *Influenza* and *Molluscipoxvirus*, *Influenza* and *Morbillivirus*, *Influenza* and *Mupapillomavirus*, *Influenza* and *Muromegalovirus*, *Influenza* and *Mycoreovirus*, *Influenza* and *Nairovirus*, *Influenza* and *Nanovirus*, *Influenza* and *Narnavirus*, *Influenza* and *Necrovirus*, *Influenza* and *Nepovirus*, *Influenza* and *Norovirus*, *Influenza* and *Novirhabdovirus*, *Influenza* and *Nucleopolyhedrovirus*, *Influenza* and *Nucleorhabdovirus*, *Influenza* and *Nupapillomavirus*, *Influenza* and *Okavirus*, *Influenza* and *Oleavirus*, *Influenza* and *Omegatetravirus*, *Influenza* and *Omikronpapillomavirus*, *Influenza* and *Orbivirus*, *Influenza* and *Orthobunyavirus*, *Influenza* and *Orthohepadnavirus*, *Influenza* and *Orthopoxvirus*, *Influenza* and *Orthoreovirus*, *Influenza* and *Oryzavirus*, *Influenza* and *Panicovirus*, *Influenza* and *Parapoxvirus*, *Influenza* and *Parechovirus*, *Influenza* and *Partitivirus*, *Influenza* and *Parvovirus*, *Influenza* and *Pefudensovirus*, *Influenza* and *Pestivirus*, *Influenza* and *Petuvirus*, *Influenza* and *Phaeovirus*, *Influenza* and *Phlebovirus*, *Influenza* and *Phytoreovirus*, *Influenza* and *Pipapillomavirus*, *Influenza* and *Plasmavirus*, *Influenza* and *Plectrovi*, *Influenza* and *Pneumovirus*, *Influenza* and *Polerovirus*, *Influenza* and *Polyomavirus*, *Influenza* and *Potexvirus*, *Influenza* and *Potyvirus*, *Influenza* and *Prasinovirus*, *Influenza* and *Prymnesiovirus*, *Influenza* and *Pseudovirus*, *Influenza* and *Ranavirus*, *Influenza* and *Raphidovirus*, *Influenza* and *Respirovirus*,

*Influenza* and *Rhadinovirus*, *Influenza* and *Rhinovirus*, *Influenza* and *Roseolovirus*, *Influenza* and *Rotavirus*, *Influenza* and *Rubivirus*, *Influenza* and *Rubulavirus*, *Influenza* and *Rudivirus*, *Influenza* and *Rymovirus*, *Influenza* and *Sapovirus*, *Influenza* and *Seadornavirus*, *Influenza* and *Sequivirus*, *Influenza* and *Siadenovirus*, *Influenza* and *Simplexvirus*, *Influenza* and *Soymovirus*, *Influenza* and *Spiromicrovirus*, *Influenza* and *Spumavirus*, *Influenza* and *Suipoxvirus*, *Influenza* and *Tectivirus*, *Influenza* and *Teschovirus*, *Influenza* and *Thetapapillomavirus*, *Influenza* and *Thogotovirus*, *Influenza* and *Tombusvirus*, *Influenza* and *Topocuvirus*, *Influenza* and *Torovirus*, *Influenza* and *Tospovirus*, *Influenza* and *Totivirus*, *Influenza* and *Trichovirus*, *Influenza* and *Tritimovirus*, *Influenza* and *Tungrovirus*, *Influenza* and *Tymovirus*, *Influenza* and *Varicellovirus*, *Influenza* and *Vesiculovirus*, *Influenza* and *Vesivirus*, *Influenza* and *Vitivirus*, *Influenza* and *Waikavirus*, *Influenza* and *Whispovirus*, *Influenza* and *Xipapillomavirus*, *Influenza* and *Yatapoxvirus*, or *Influenza* and *Zetapapillomavirus*.

The infected cells can be from prokaryotic cells. Examples of prokaryotic cells which can be used with the disclosure include but are not limited to: *Bacillus anthracis, Staphylococcus aureus*, Methicillin resistant *Staphylococcus aureus* (MRSA), Methicillin-Sensitive *Staphylococcus Aureus* (MSSA), *Mycobacterium tuberculosis* (MTB). Other bacterial cells include, but are not limited to: *Escherichia coli, Salmonella, Shigella, Klebsiella, Pseudomonas, Pseudomonas aeruginosa, Listeria monocytogenes, Mycobacterium aviumintracellulare, Yersinia, Francisella, Pasteurella, Brucella, Clostridia, Bordetella pertussis, Bacteroides, Staphylococcus aureus, Streptococcus pneumonia, B-Hemolytic strep., Corynebacteria, Legionella, Mycoplasma, Ureaplasma, Chlamydia, Neisseria gonorrhea, Neisseria meningitides, Hemophilus influenza, Enterococcus faecalis, Proteus vulgaris, Proteus mirabilis, Helicobacter pylori, Treponema palladium, Borrelia burgdorferi, Borrelia recurrentis, Rickettsial pathogens, Nocardia*, and *Acitnomycetes*.

Parasites which can be used with the present disclosure include, but are not limited to: malarial parasites, *Plasmodium falciparum, Plasmodium malaria, Plasmodium vivax, Plasmodium ovale, P. knowlesi, Onchoverva volvulus, Leishmania, Trypanosoma* spp., *Schistosoma* spp., *Entamoeba histolytica, Cryptosporidum, Giardia* spp., *Trichimonas* spp., *Balatidium coli, Wuchereria bancrofti, Toxoplasma* spp., *Enterobius vermicularis, Ascaris lumbricoides, Trichuris trichiura, Dracunculus medinesis*, trematodes, *Diphyllobothrium latum, Taenia* spp., *Pneumocystis carinii*, and *Necator americanis*.

In some applications the sample comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, or 100,000 different species of viruses. In some embodiments, the sample comprises about 1 to about 10, about 10 to about 100, about 10 to about 1000, about 100 to about 1000, about 100 to about 10,000, about 1000 to 10,000, about 10,000 to about 50,000, or about 10,000 to about 100,000 different species of viruses.

In some applications the sample comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, or 100,000 different subspecies of viruses. In some embodiments, the sample comprises about 10 to about 100, about 10 to about 1000, about 100 to about 1000, about 100 to about 10,000, about 1000 to 10,000, about 10,000 to about 50,000, or about 10,000 to about 100,000 different subspecies of viruses.

In some applications the sample comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, or 100,000 different strains of viruses. In some embodiments, the sample comprises about 10 to about 100, about 10 to about 1000, about 100 to about 1000, about 100 to about 10,000, about 1000 to 10,000, about 10,000 to about 50,000, or about 10,000 to about 100,000 different strains of viruses.

In some embodiments, target viral in a genome to be analyzed methods, systems and kits disclosed herein can comprise about, more than about, less than about, or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1000, 2000, 3000, 4000, 5000, 6000, 7000, 8000, 9000, 10,000, 20,000, 30,000, 40,000, 50,000, 60,000, 70,000, 80,000, 90,000, or 100,000 molecular markers or genetic variations in a droplet compartment. In some embodiments, number of targets to be analyzed is about 2 to about 5, about 2 to about 10, about 2 to about 20, about 2 to about 30, about 2 to about 40, about 2 to about 50, about 2 to about 100, about 5 to about 10, about 5 to about 25, about 5 to about 50, about 5 to about 100, about 10 to about 20, about 10 to about 50, about 10 to about 100, about 25 to about 50, about 25 to about 75, about 25 to about 100, about 100 to about 200, about 100 to about 500, about 100 to about 1000, about 500 to about 1000, about 1000 to about 5000, about 1000 to about 10,000, about 10,000 to about 20,000, about 10,000 to about 50,000, about 10,000 to about 100, 000, or about 50,000 to about 100,000 molecular markers or genetic variations in a droplet compartment.

B. Sample Preparation

Before analyzing the sample it may often be desirable to perform one or more sample preparation operations upon the sample. Generally, these sample preparation operations may include such manipulations as extraction of intracellular material from a cell, tissue or organisms, such as the extraction of nucleic acids, protein, or other macromolecules from the samples.

Often, the methods and compositions provided herein are used in order to detect, diagnose, monitor, or prognose the course of disease or infection (e.g., viral infection, parasitic infection, bacterial infection) in a clinical subject, particularly a human subject. The human can be a new-born, a baby, a child, an adolescent, a teenager, an adult, or a senior citizen. The human can be female or male. The human can be between about 1 month and 12 months old; for example, about 1, 2, 3, 4, 5, 6, 7, 8, 9, 10, 11, or 12 months old. The human can be between about 1 years old and about 110 years old; for example, about 1-110, 1-65, 1-35, 1-18, 1-11, 1-6, 1-2, 2-110, 2-65, 2-35, 2-18, 2-11, 2-6, 6-110, 6-65, 6-35, 6-18, 6-11, 11-110, 11-65, 11-35, 11-18, 18-110, 18-65, 18-35, 35-110, 35-65, 65-110, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50, 55, 60, 65, 70, 75, 80, 90, 100, 110 years of age. The methods may also be used for non-human animal subjects.

The methods of the present disclosure provide for obtaining a biological sample from a subject. As used herein, the term subject refers to any animal, particularly humans, but also including non-human subjects such as non-human mammals, apes, gorillas, chimpanzees, cows, horses, dogs, cats, giraffes, zebras, rodents (e.g., rats, mice, guinea pigs), sheep, goats, moose, deer, pigs, chickens, roosters, fowl, pigeons, birds, reptiles, crocodiles, alligators, lizards. The methods and compositions may be particularly useful for animal husbandry, to monitor, detect, diagnose and/or predict disease or infection in captive or domesticated animals. The methods and compositions can also be used to track microbial evolution in the wild, either within a particular species, or across species or in epidemiological studies that examine infections across a population, including during epidemics or pandemics.

A biological sample can be obtained by methods known in the art including swabbing, scraping, phlebotomy, biopsy (e.g., excisional, fine needle aspiration, incisional, core needle, etc.), or any other suitable method. In preferred embodiments, particularly for subjects having or suspected of having a flu infection, a Nasopharyngeal aspirate (NPA), nasal swab (NS), throat swab (TS) or buccal swab may be used to obtain the sample.

Biological samples can be obtained from any of the tissues provided herein; including, but not limited to lung, respiratory tract, nasal cavity, gastrointestinal tract, mouth, skin, heart, lung, kidney, breast, pancreas, liver, blood, muscle, smooth muscle, bladder, gall bladder, colon, intestine, brain, prostate, esophagus, or thyroid. Alternatively, the sample can be obtained from any other source; including, but not limited to, blood, sweat, hair follicle, buccal tissue, tears, menses, feces, sputum, nasal cavities, or saliva. The biological sample can be obtained by a medical professional (e.g, infectious disease specialist, tropical medicine specialist). The medical professional can refer the subject to a testing center or laboratory for submission of the biological sample. In some cases, the subject can directly provide the biological sample.

The diagnosis of a particular infection or other condition can include an examination of a subject by a physician, nurse or other medical professional. The examination can be part of a routine examination, or the examination can be due to a specific complaint including, but not limited to, one of the following: pain, illness, anticipation of illness, presence of a suspicious lump or mass, a disease, or a condition. The subject may or may not be aware of the disease or condition. The medical professional can obtain a biological sample for testing. In some cases the medical professional can refer the subject to a testing center or laboratory for submission of the biological sample.

1. Macromolecule Extraction

When the methods are applied to applications where whole cells, viruses or other tissue samples are to be analyzed, it may typically be necessary to extract the nucleic acids from these samples. Accordingly, following obtaining a sample, the nucleic acids may be liberated from the collected sample, for example, cells, viral coat (capsid or envelope), etc., into a crude extract.

Accessing the nucleic acids and macromolecules from the intercellular space of the sample cells or viruses, and denaturation of DNA binding proteins may generally be performed by either physical, chemical methods, or a combination of both. In some applications of the methods, following the isolation of the crude extract, it will often be desirable to separate the nucleic acids from other elements of the crude extract, e.g., proteins, cell membrane particles, and the like. In some applications of the methods it will be desirable to keep the nucleic acids with its proteins, and cell membrane particles.

In some applications of the methods provided herein, DNA or RNA can be extracted from a biological sample prior to analysis using methods of the disclosure. Extraction can be by means including, but not limited to, the use of detergent lysates, sonication, or vortexing with glass beads. In particular embodiments, DNA can be extracted according to standard methods from blood, e.g., with the use of the Qiagen UltraSens DNA extraction kit. In some embodiments, isolated nucleic acid molecules can be fragmented or left intact depending on the application. Reaction conditions and enzymes that can be employed for such isolation and fragmentation are known to a person of ordinary skill in the relevant art (e.g., from the protocols supplied by the manufacturers), and could be optimized thereby for such uses. In another embodiment, nucleic acid molecules can be isolated using any technique suitable in the art including, but not limited to, techniques using gradient centrifugation (e.g., cesium chloride gradients, sucrose gradients, glucose gradients, etc.), centrifugation protocols, boiling, purification kits (e.g., Qiagen purification systems; Promega purification systems; Amersham purification systems; Invitrogen Life Technologies Purification; Mo-Bio Laboratories purification systems, etc.). Methods of extracting nucleic acids can also include the use of liquid extraction with agent extraction methods such as methods using Trizol or DNAzol.

In some applications of the methods provided herein are directed to methods for isolating nucleic acids outside of cells, for example viral or bacterial nucleic acids. Such a method is generally comprised of the following steps: (a) obtaining a sample containing nucleic acids; (b) adding a cell lysis inhibitor, cell membrane stabilizer or cross-linker to the sample; and (c) isolating the nucleic acids.

Some applications of the methods provided herein may be directed to methods for isolating intracellular nucleic acids, for example viral or bacterial nucleic acids. Such a method generally comprises the following steps: (a) obtaining a sample of one or more infected cells; (b) adding a cell lysis reagent to the cell population; (c) lysing the infected cells, and (d) isolating the nucleic acids. In some cases, the cell lysing may occur prior to partitioning. In some cases, the cell lysing may occur within the partition.

2. Dilutions

In some applications of the methods it is desirable to prepare the sample in a limited dilution so that there is a limited number and known amount of nucleic acids, polypeptides and/or macromolecules in a particular volume such as a particular droplet volume. In some applications of the methods provided herein, the target nucleic acids, polypeptides, and/or macromolecules are present at an average concentration of less than about five copies per droplet (e.g., compartment), less than about four copies per droplet, less than about three copies per droplet, less than about two copies per droplet, or less than about one copy per droplet, or less than about 0.5 copies per droplet, or less than about 0.4 copies per droplet, or less than about 0.3 copies per droplet, or less than about 0.2 copies per droplet, or less than about 0.1 copies per droplet. In some cases, the nucleic acids, polypeptides and/or macromolecules may be present at an average concentration of about 5, 4, 3, 2, 1, 0.5, 0.4, 0.3, 0.2, 0.1, 0.095, 0.09, 0.085, 0.08, 0.075, 0.07, 0.065, 0.06, 0.055, 0.05, 0.045, 0.04, 0.035, 0.03, 0.025, 0.02, 0.015, 0.01, 0.0095, 0.009, 0.0085, 0.008, 0.0075, 0.007, 0.0065, 0.006, 0.0055, 0.005, 0.0045, 0.004, 0.0035, 0.003, 0.0025, 0.002, 0.0015, or about 0.001 copies per droplet. In some cases, the nucleic acids polypeptides and/or macromolecules may be present at an average concentration of more than about 5, 4, 3, 2, 1, 0.5, 0.4, 0.3, 0.2, 0.1, 0.095, 0.09, 0.085, 0.08, 0.075, 0.07, 0.065, 0.06, 0.055, 0.05, 0.045, 0.04, 0.035, 0.03, 0.025, 0.02, 0.015, 0.01, 0.0095, 0.009, 0.0085, 0.008, 0.0075, 0.007, 0.0065, 0.006, 0.0055, 0.005, 0.0045, 0.004, 0.0035, 0.003, 0.0025, 0.002, 0.0015, or 0.001 copies per droplet or more. In some cases, the nucleic acids, polypeptides and/or macromolecules may be present at an average concentration of less than about 5, 4, 3, 2, 1, 0.5, 0.4, 0.3, 0.2, 0.1, 0.095, 0.09, 0.085, 0.08, 0.075, 0.07, 0.065, 0.06, 0.055, 0.05, 0.045, 0.04, 0.035, 0.03, 0.025, 0.02, 0.015, 0.01, 0.0095, 0.009, 0.0085, 0.008, 0.0075, 0.007, 0.0065, 0.006, 0.0055, 0.005, 0.0045, 0.004, 0.0035, 0.003, 0.0025, 0.002, 0.0015, or about 0.001 copies per droplet or less.

In some applications of the methods, a sample comprising genomic nucleic acids may be partitioned into compartments (e.g., droplets). In some cases, the sample comprises microbial genomes (e.g., viral genomes, bacterial genomes, parasitic genomes). In some cases, the microbial genomes (e.g., viral genomes, bacterial genomes, parasitic genomes) are partitioned into compartments (e.g., droplets) at an average concentration of less than about 5, 4, 3, 2, 1, 0.5, 0.4, 0.3, 0.2, 0.1, 0.095, 0.09, 0.085, 0.08, 0.075, 0.07, 0.065, 0.06, 0.055, 0.05, 0.045, 0.04, 0.035, 0.03, 0.025, 0.02, 0.015, 0.01, 0.0095, 0.009, 0.0085, 0.008, 0.0075, 0.007, 0.0065, 0.006, 0.0055, 0.005, 0.0045, 0.004, 0.0035, 0.003, 0.0025, 0.002, 0.0015, or about 0.001 microbial genome copies per compartment (e.g., droplet) or less. In some cases, the sample is derived from an infected human or other mammalian or non-mammalian subject. In some cases, the microbial nucleic acids (e.g., HIV reverse-transcribed DNA) may be integrated into the human genome or the sample may comprise a mixture of free human nucleic acids and free microbial nucleic acids. In such cases, the microbial genomes (e.g., viral genomes, bacterial genomes, parasitic genomes) are partitioned into compartments (e.g., droplets) present at an average concentration of less than about 5, 4, 3, 2, 1, 0.5, 0.4, 0.3, 0.2, 0.1, 0.095, 0.09, 0.085, 0.08, 0.075, 0.07, 0.065, 0.06, 0.055, 0.05, 0.045, 0.04, 0.035, 0.03, 0.025, 0.02, 0.015, 0.01, 0.0095, 0.009, 0.0085, 0.008, 0.0075, 0.007, 0.0065, 0.006, 0.0055, 0.005, 0.0045, 0.004, 0.0035, 0.003, 0.0025, 0.002, 0.0015, or about 0.001 microbial genome copies per compartment (e.g., droplet) or less. In some cases, however, where the sample comprises a mixture of microbial nucleic acids (e.g., viral, bacterial, parasitic) and mammalian nucleic acids (e.g., human, rodent, etc.), the sample is partitioned such that the mammalian nucleic acids (e.g., human, rodent, etc.) are present at an average concentration of less than about 5, 4, 3, 2, 1, 0.5, 0.4, 0.3, 0.2, 0.1, 0.095, 0.09, 0.085, 0.08, 0.075, 0.07, 0.065, 0.06, 0.055, 0.05, 0.045, 0.04, 0.035, 0.03, 0.025, 0.02, 0.015, 0.01, 0.0095, 0.009, 0.0085, 0.008, 0.0075, 0.007, 0.0065, 0.006, 0.0055, 0.005, 0.0045, 0.004, 0.0035, 0.003, 0.0025, 0.002, 0.0015, or about 0.001 mammalian genome copies per compartment (e.g., droplet) or less. In some applications of the methods, it is desirable to prepare the sample in a limited dilution so that there is a limited number and known amount of intact cells, intact viral particles, or particles from another organism (e.g., bacteria). In some applications of the method provided herein, the cells or particles are present at an average concentration of about 5, 4, 3, 2, or 1 particles or cells per droplet. In some cases, the cells or particles are present at an average concentration of more than about 5, 4, 3, 2, or 1 particles or cells per droplet or more. In some cases, the cells or particles are present at an average concentration of less than about 5, 4, 3, 2, or 1 particles or cells per droplet or less. In some cases, false positive measurements may occur when two fragments co-localize within a partition by chance. In some cases, partitioning intact viral particles may prevent false positive measurements of recombination due to fragmentation.

In some applications of the methods it may be desirable to prepare the sample with large numbers of compartments or partitions. In some cases, compartments may be droplets. In some cases, the number of droplets may be about 10,000,000, 15,000,000, 20,000,000, 25,000,000, 30,000,000, 35,000,000, 40,000,000, 45,000,000, 50,000,000, 55,000,000, 60,000,000, 65,000,000, 70,000,000, 75,000,000, 80,000,000, 85,000,000, 90,000,000, 95,000,000, 100,000,000, 125,000,000, 150,000,000, 175,000,000, 200,000,000, 225,000,000, 250,000,000, 275,000,000, 300,000,000, 325,000,000, 350,000,000, 375,000,000, 400,000,000, 425,000,000, 450,000,000, 475,000,000, or about 500,000,000 droplets. In some cases, the number of droplets may be more than about 10,000,000, 15,000,000, 20,000,000, 25,000,000, 30,000,000, 35,000,000, 40,000,000, 45,000,000, 50,000,000, 55,000,000, 60,000,000, 65,000,000, 70,000,000, 75,000,000, 80,000,000, 85,000,000, 90,000,000, 95,000,000, 100,000,000, 125,000,000, 150,000,000, 175,000,000, 200,000,000, 225,000,000, 250,000,000, 275,000,000, 300,000,000, 325,000,000, 350,000,000, 375,000,000, 400,000,000, 425,000,000, 450,000,000, 475,000,000, or about 500,000,000 droplets. In some cases, the number of droplets may be less than about 10,000,000, 15,000,000, 20,000,000, 25,000,000, 30,000,000, 35,000,000, 40,000,000, 45,000,000, 50,000,000, 55,000,000, 60,000,000, 65,000,000, 70,000,000, 75,000,000, 80,000,000, 85,000,000, 90,000,000, 95,000,000, 100,000,000, 125,000,000, 150,000,000, 175,000,000, 200,000,000, 225,000,000, 250,000,000, 275,000,000, 300,000,000, 325,000,000, 350,000,000, 375,000,000, 400,000,000, 425,000,000, 450,000,000, 475,000,000, or about 500,000,000 droplets or less.

False positive measurements of recombinant molecules may occur when parental molecules and fragments co-localize within a partition by chance. In some cases, false positive measurements of recombinant molecules may be extremely low. In some cases, false positive events may be less than about $10^{-6}$. In some cases, false positive measurements of recombinant molecules may be expressed as the square of the copies per partition, for example, 0.001×0.001. In some cases, the amount of fragmentation of a sample may be small. In some cases, fragmentation of a sample may be less than about 10%. In these cases, the number of false positive measurements may be low.

In some applications of the methods, recombinant molecules may have more than one marker present per partition. In some cases, recombinant molecules may have two markers present per partition. In some cases, recombinant molecules may have more than two markers present per partition. In some cases, co-localized molecules of opposite parent forms may have one more marker than recombinant molecules. In some cases, co-localized molecules of opposite parent forms may have two more markers than recombinant molecules. In some cases, the number of markers may be different between recombinant molecules and co-localized molecules. In these cases, a difference in marker number may be used to identify false positive measurements from recombined molecules. For example, a recombinant molecule may have two markers present per droplet compared with co-localized parental molecules of opposite parent forms which may have 3 or 4 markers present per droplet.

3. Fragmentation

In some applications of the methods, it is desirable to keep molecules (e.g., viral genomic nucleic acids) intact or substantially non-fragmented such as when determining viral recombination rate, or linkage of one or markers in a genome.

In some cases, fragmentation of a portion of the sample may occur. In some cases, the weight percent of the sample that is fragmented may be about 95%, 90%, 85%, 80%, 75%, 70%, 65%, 60%, 55%, 50%, 45%, 40%, 35%, 30%, 25%, 20%, 15%, 10%, 5%, 4%, 3%, 2%, 1%, 0.9%, 0.8%, 0.7%, 0.6%, 0.5%, 0.4%, 0.3% 0.2%, 0.1%, 0.09%, 0.08%, 0.07%, 0.06%, 0.05%, 0.04%, 0.03%, 0.02%, or about 0.01%. In some cases, the weight percent of the sample that is fragmented may be less than about 95%, 90%, 85%, 80%, 75%, 70%, 65%, 60%, 55%, 50%, 45%, 40%, 35%, 30%, 25%, 20%, 15%, 10%, 5%, 4%, 3%, 2%, 1%, 0.9%, 0.8%, 0.7%, 0.6%, 0.5%, 0.4%, 0.3% 0.2%, 0.1%, 0.09%, 0.08%, 0.07%, 0.06%, 0.05%, 0.04%, 0.03%, 0.02%, or about 0.01% or less. In some cases, the weight percent of the sample that is fragments may be more than about 95%, 90%, 85%, 80%, 75%, 70%, 65%, 60%, 55%, 50%, 45%, 40%, 35%, 30%, 25%, 20%, 15%, 10%, 5%, 4%, 3%, 2%, 1%, 0.9%, 0.8%, 0.7%, 0.6%, 0.5%, 0.4%, 0.3% 0.2%, 0.1%, 0.09%, 0.08%, 0.07%, 0.06%, 0.05%, 0.04%, 0.03%, 0.02%, or about 0.01% or more. In some applications, it may be desirable to calculate the extent of fragmentation. Extent of fragmentation may be determined based on the fraction of single positives compared with parental double positives within a sample. In some cases, such as higher sample input concentrations, extent of fragmentation may be utilized to correct for random co-localization of two fragments within a given partition such that the partition gives the same Ch1 fluorescence intensity and the same Ch2 fluorescence intensity as a partition containing a single recombinant molecule, thereby falsely indicating a recombination event. In some cases, extent of fragmentation may be utilized to score the total number of genomes present in a sample.

In some cases, when the distance between two markers of interest is greater than about 10 kilobases (kb), 11 kb, 12 kb, 13 kb, 14 kb, 15 kb, 16 kb, 17 kb, 18 kb, 19 kb, 20 kb or more, genomic molecules may be fragmented in a sample (e.g., DNA or RNA) such that the two markers of interest are physically separated. In some cases, when the two markers of interest are separately by a relatively short distance, e.g., about less than 10 kb, 9 kb, 8 kb, 7 kb, 6 kb, 5 kb, 4 kb, 3 kb, 2 kb), genomic molecules of interest may not be fragmented in a sample, such that the two markers of interest remain physically linked. In some cases, the percent of sample fragmentation may be reduced by directly partitioning the intact virus or bacterium into partitions before release of the genomic molecule being scored.

Figure 16:
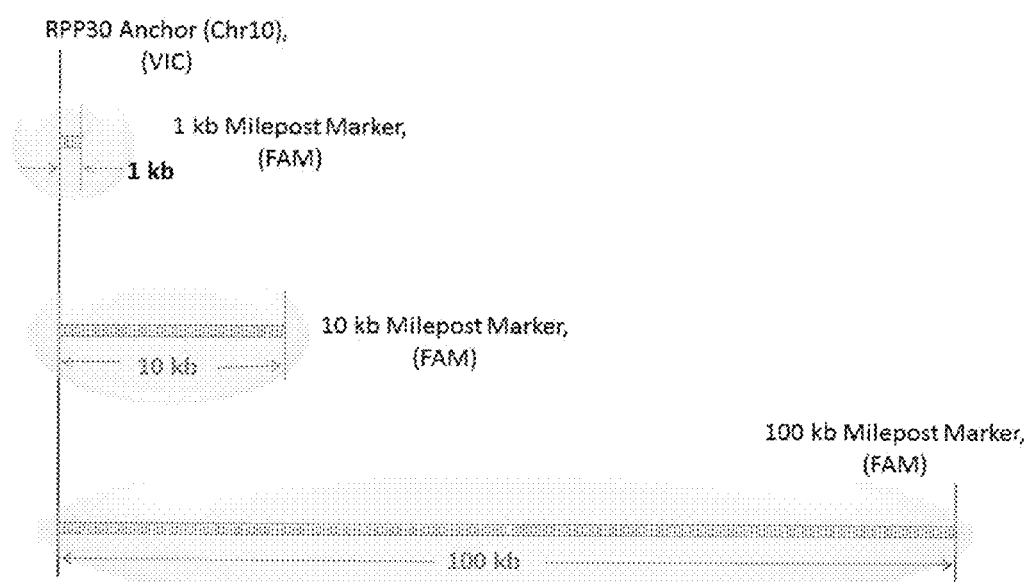
FIG. 16 illustrates FAM-labeled milepost markers of various lengths, (1 kb, 10 kb, 100 kb) that may be linked to a VIC-labeled anchor (RPP30 Anchor) to provide a ruler for DNA size measurements.
Figure 17A:
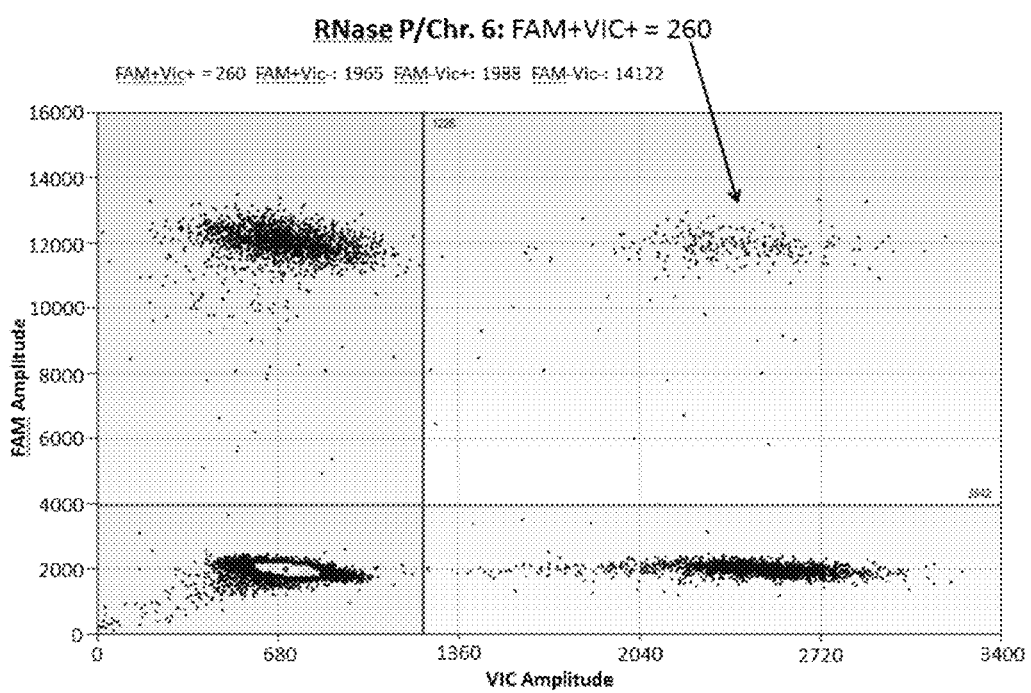
FIGS. 17A, 17B, 17C, and 17D illustrate 2D fluorescence intensity plots showing the number of double positive FAM+/VIC+ droplets for each duplexed RNaseP: Chromosome 10 milepost marker (1 kb in FIG. 17B, 10 kb in FIG. 17C, 100 kb in FIG. 17D) assay compared to the duplex assay for the unlinked loci RNase P and Chromosome 6 marker, FIG. 17A. Total double positive counts are indicated by the arrow in the upper right quadrant of each 2D plot for comparable DNA inputs for each duplex assay.
Figure 17B:
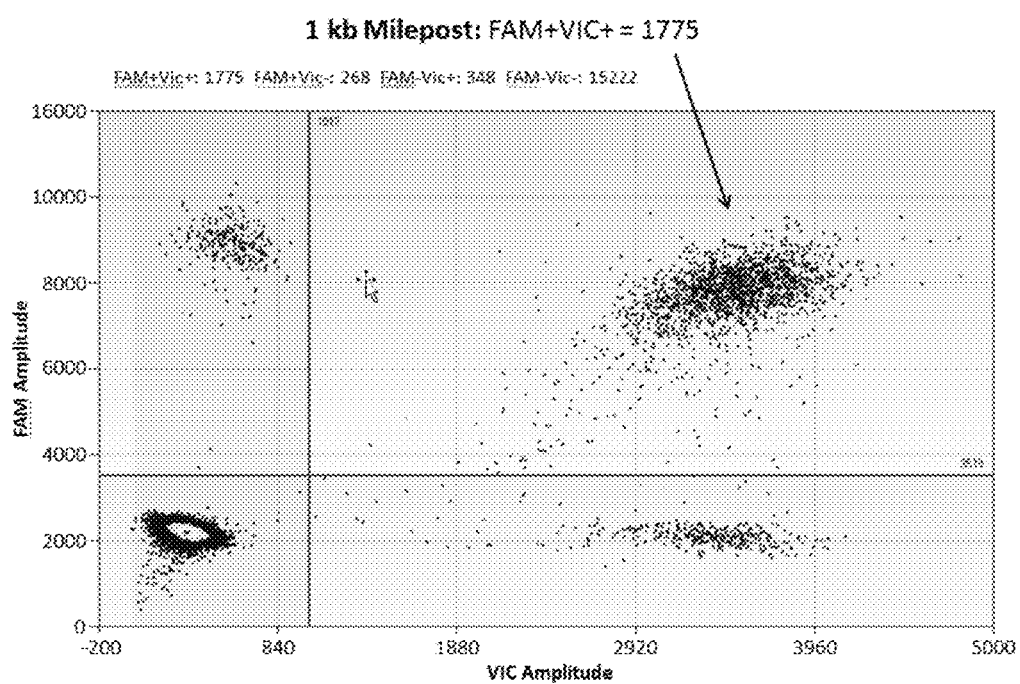
Figure 17C:
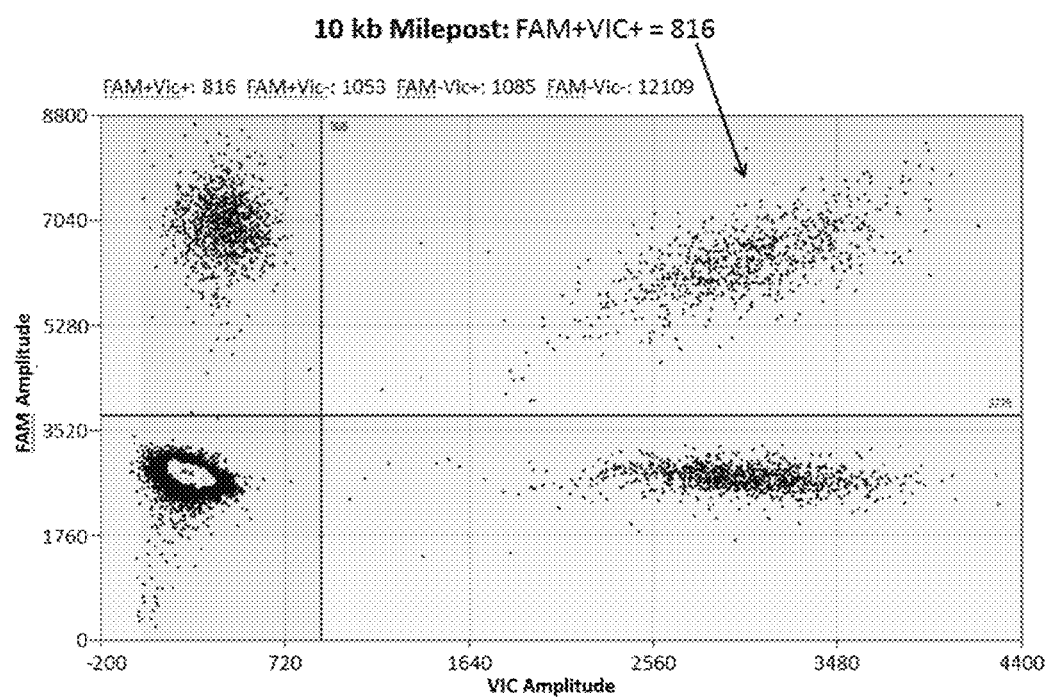
Figure 17D:
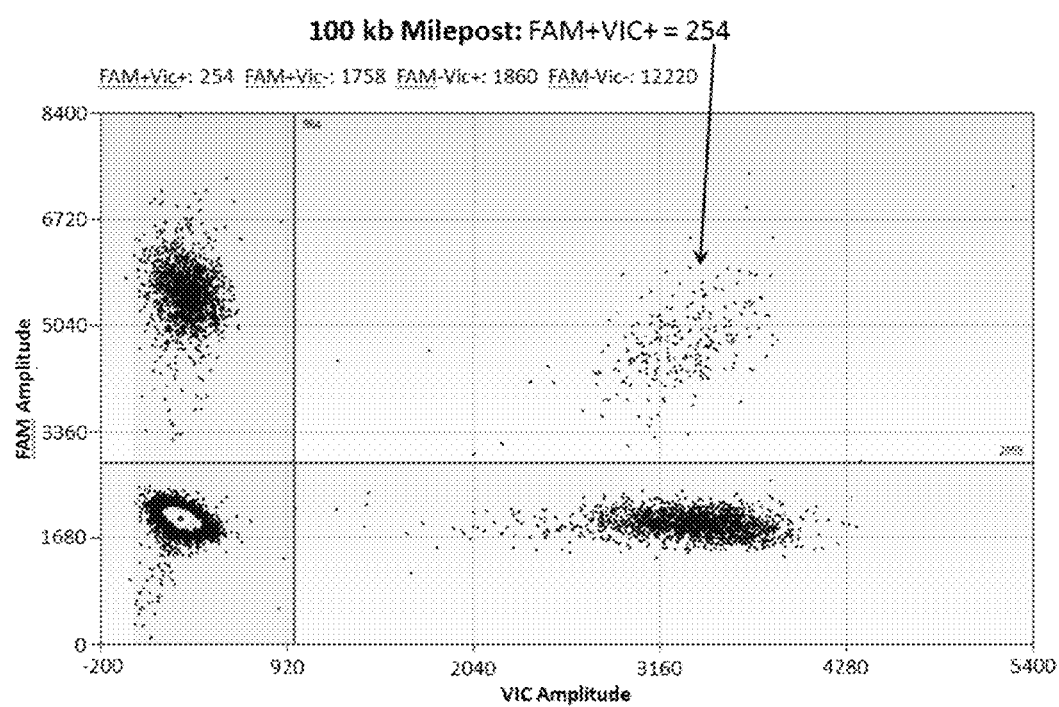
Figure 18A:
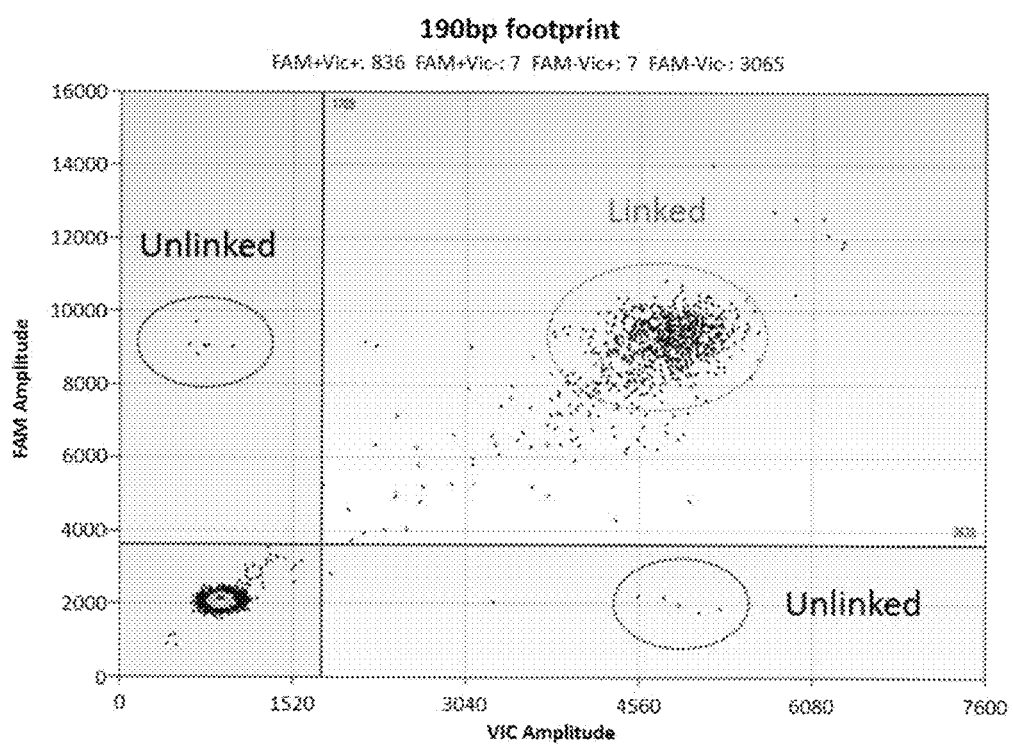
FIGS. 18A and 18B illustrate 2D fluorescence intensity plots showing the number of FAM/VIC+/+ double positive ("linked") molecules in another undigested DNA sample, reflecting a tight physical linkage between the anchor and milepost marker for a 190 bp footprint, FIG. 18A and for a 1 kp footprint, FIG. 18B.
Figure 18B:
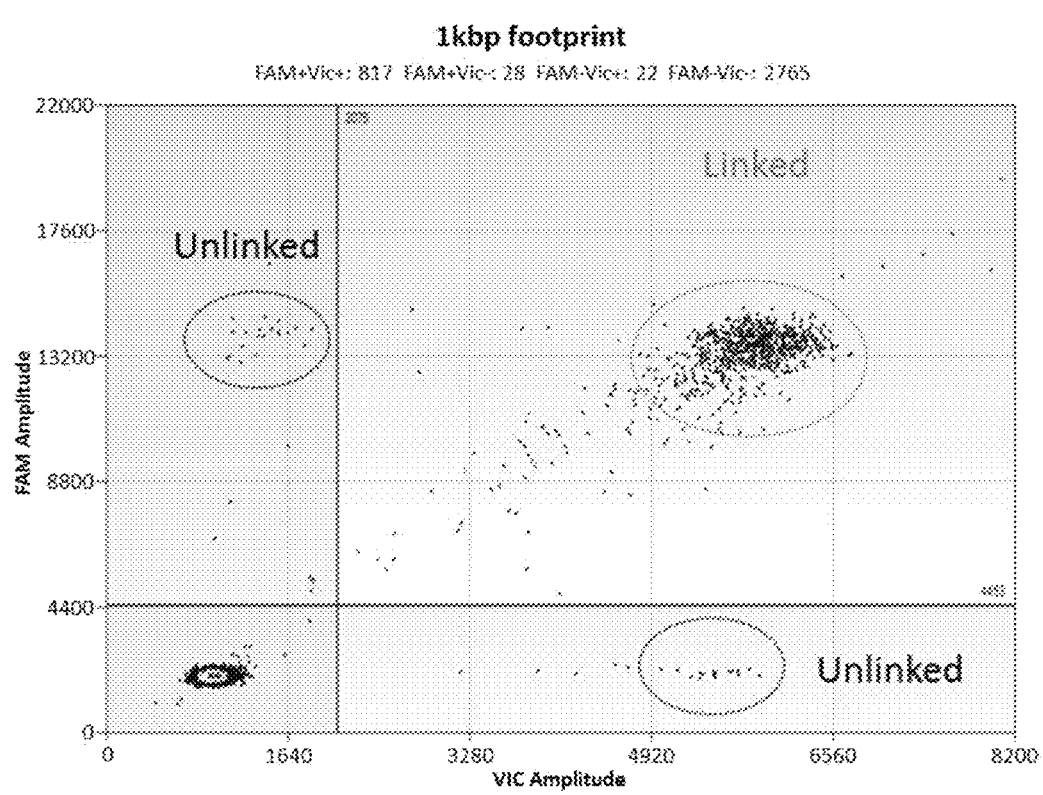

Increasing the genomic distance between two markers of interest may increase the percentage of those markers that will be physically separated. Decreasing the genomic distance between two markers of interest may increase the percentage of those markers that remain physically linked. For example, FAM-labeled milepost markers of various lengths, (1 kb, 10 kb, 100 kb) may be linked to a fluorescent anchor (e.g. VIC labeled RPP30), see FIG. 16. In these cases, the number of double positive measurements (FAM+/VIC+) representing physically linked molecules can be counted for each milepost marker (1 kb, 10 kb, 100 kb) and compared to the digested sample. In other cases, a duplex assay may be utilized with undigested DNA to determine markers on different chromosomes, for example, RNase P and Chromosome 6 as in FIGS. 17A-D. Counts of linked molecules in the 2D fluorescence intensity plots as a function of marker size may represent DNA fragment size distribution in a plasma DNA sample, see FIGS. 17A-D. In some cases, the significant discrepancy between the number of randomly co-localized double positives in the RNase P: Chr6 control duplex, FIG. 17A, compared to the number of double-positives in the 1 kb (FIG. 17B) and 10 kb (FIG. 17C) milepost duplexes, may reveal the extent of linkage between markers on the same DNA molecule. In some cases, as distance between markers increases, the number of intact DNA molecules in a sample preparation may decrease and linkage may not be detectable at great distances (e.g., 100 kb milepost in this sample, see FIG. 17D). The number of FAM/VIC+/+ double positive ("linked") molecules in another undigested DNA sample of milepost markers (190 bp footprint, FIG. 18A and 1 kp footprint, FIG. 18B) may indicate a tight physical linkage between the anchor and the milepost marker.

In some cases, the distance between two loci of interest may be 1, 2, 3, 4, 5, 6, 7, 8, 9, 10, 20, 30, 33, 40, 50, 60, 70, 80, 90, 100, 110, 120, 130, 140, 150, 160, 170, 180, 190, 200, 210, 300, 400, 500, 600, 700, 800, 900, 1000, or 10,000 kb. In some cases, the distance between two loci may be more than 1, 2, 3, 4, 5, 6, 7, 8, 9, 10, 20, 30, 33, 40, 50, 60, 70, 80, 90, 100, 110, 120, 130, 140, 150, 160, 170, 180, 190, 200, 210, 300, 400, 500, 600, 700, 800, 900, 1000, or 10,000 kb or more. In some cases, the distance between two loci may be less than 2, 3, 4, 5, 6, 7, 8, 9, 10, 20, 30, 33, 40, 50, 60, 70, 80, 90, 100, 110, 120, 130, 140, 150, 160, 170, 180, 190, 200, 210, 300, 400, 500, 600, 700, 800, 900, 1000, or 10,000 kb or less.

In some cases, a sample may comprise fragmented nucleic acids and may be partitioned into multiple compartments (e.g., droplets) for subsequent analysis. In these cases, a compartment may comprise a plurality of fragments. If two or more of the fragments comprise different markers of interest, then a plurality of markers may co-localize to a single compartment and may thus be detected within the same compartment. In order to determine whether the co-localized markers are present in the compartment because (a) they are present on separate fragments that are within the compartment or (b) they are present on a single nucleic acid molecule within the compartment, it may be useful, in some cases, to run a control sample. Such control sample may contain a subset of the original sample but may be treated with an agent to disrupt or cleave the nucleic acid between the plurality of markers of interest. Often, the agent is a restriction enzyme that is able to cleave the nucleic acid within a region between two markers of interest. For example, a nucleic acid sample with a G and T marker present on different nucleic acid strands may be plotted on a cluster diagram showing significant single positive droplets, reflecting that the two markers are partitioned into separate compartments. A nucleic acid sample with A and T markers of interest on the same nucleic acid strand may be plotted on a cluster plot depicting the presence of many double positive droplets (e.g. HEX/FAM), which generally reflects that the markers are present on the same strand. A control sample that is digested with a restriction enzyme may be depicted on the cluster plot showing a reduction in the percentage of double positive droplets compared to the plot of the nucleic acid sample with A and T markers. A reduction in the percentage of double positive droplets may reflect that the markers of interest are actually linked in the undigested sample and that this linkage is disrupted by the restriction enzyme. Conversely, the remaining double-positive droplets may reflect droplets that comprise two markers on separate fragments of nucleic acids. The remaining droplets may also reflect droplets that contain two markers that are linked on a single strand but that, for whatever reason, were not digested during the restriction enzyme digest. Some reasons may include that the reaction was not a complete reaction or that the restriction site between the two markers has a particular polymorphism making it resistant to the enzyme.

In some applications, it may be desirable to fragment the sample prior to performing the assay. In some cases, it may be desirable to fragment the sample prior to partitioning. In some cases, a restriction enzyme may be used to fragment the sample. In some cases, fragmentation controls may be used (e.g., either positive or negative controls). For example, a sample known to be extensively fragmented may be used as a fragmentation control. In other cases, restriction enzymes may be used to unlink individual full length copies. In these cases, double positives that remain following restriction digest may be fragments.

In some applications, it may be desirable to fragment the sample, particularly a DNA sample or RNA sample, prior to partitioning to reduce fluid viscosity. In some cases, fluids with high viscosity may not form partitions. In some cases, the amount of nucleic acids (particularly DNA) in a sample may increase the aqueous phase viscosity—particularly when the nucleic acids are present at a relatively high concentration. In some cases, the amount of virus particles in a sample may increase the aqueous phase viscosity. In some cases, viscosity may be reduced by fragmenting the sample prior to partitioning.

In some cases, two markers known to be separated by a great distance, e.g., greater than 1 kb, greater than 10 kb, greater than 20 kb, greater than 50 kb, greater than 75 kb, greater than 100 kb, etc., may be used as a positive fragmentation control. This is because fragmentation rate is ordinarily directly correlated with the distance between two markers. In some cases, two markers known to be separated by a relatively short distance, e.g., less than 10 kb, less than 5 kb, less than 1 kb, less than 100 bp, less than 50 bp, less than 25 bp, or less than 10 bp, may be used as a negative control for fragmentation. A relatively short separation may indicate that the two markers are less likely to be physically separated from each other by fragmentation.

The length of nucleic acids, polypeptide, or macromolecules or fragments of nucleic acids or macromolecules, can be about 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000, 9,000,000, 10,000,000, 20,000,000, 30,000,000, 40,000,000, 50,000,000, 60,000,000, 70,000,000, 80,000,000, 90,000,000, 100,000,000, 110,000,000, 120,000,000, 130,000,000, 140,000,000, 150,000,000, 160,000,000, 170,000,000, 180,000,000, 190,000,000, 200,000,000, 210,000,000, 220,000,000, 230,000,000, 240,000,000, or 250,000,000 or more nucleotides or base pairs or amino acids, etc. in length.

Figure 3:
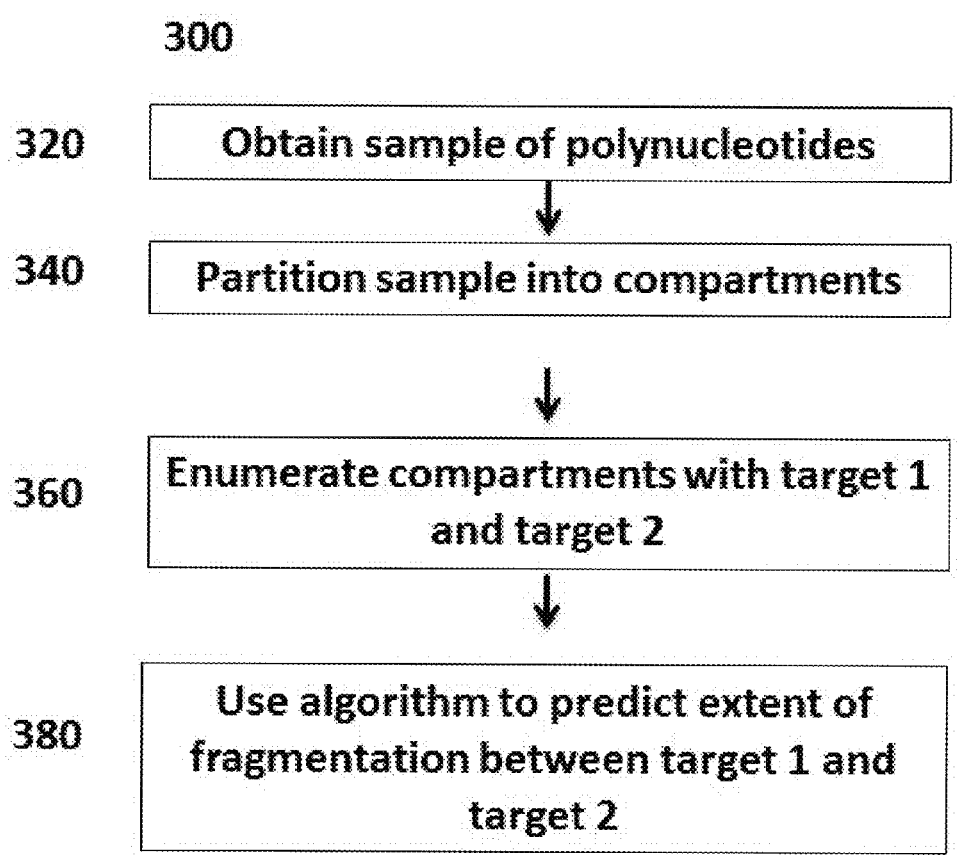
FIG. 3 provides an overview of an embodiment for predicting fragmentation in nucleic acids (also applicable to recombination).

Digital analysis can be performed to determine the extent of fragmentation between two markers in a sample. In some cases, extent of fragmentation may be measured in the sample used to measure recombination frequency. FIG. 3 illustrates one embodiment of a workflow to determine the extent of fragmentation (300). In some cases, the extent of fragmentation can be used in order to adjust any values arrived at for determining a recombination rate or frequency. Although the figure specifies fragmentation (380), the algorithm can also be used to predict recombination, with or without predicting fragmentation as well. The steps in FIG. 3 can be performed in any suitable order and combination and can be united with any other steps of the present disclosure. A sample of polynucleotides can be obtained (320). The sample can be compartmentalized into a plurality of compartments (e.g., droplets, wells) (340) such that each compartment contains on average less than about 0, 0.1, 0.2, 0.3, 0.4, 0.5, 0.6, 0.7, 0.8, 0.9, 1, 2, 4, 5, 6, 7, 8, 9, 10, 20, 30, 40, 50, 60, 70, 80, 90, 100, 125, 150, 175, 200, 300, 400, 500, 750, 1000, 5000, or 10000 target polynucleotides. In a preferred embodiment, each compartment may contain, on average, less than 10 target polynucleotides. In some cases, each compartment contains, on average, less than 10, 9, 8, 7, 6, 5, 4, 3, 2, or 1 copies of a target nucleic acid per compartment (e.g., droplet). In some cases, at least 1, 2, 3, 4, 5, 6, 7, 8, 9, 10, 20, 30, 40, 50, 60, 70, 80, 90, 100, 125, 150, 175, 200, 500, 1000, 5000, 10000, 50000, or more compartments (e.g., droplets) have zero copies of a target nucleic acid. The compartments can be assayed to enumerate compartments with a first target and a second target sequence (360) and an algorithm can be used to predict fragmentation between the first and second target sequence (380) as well as recombination rates between such sequences and that of a foreign genome. The algorithm may also be used to predict recombination events between the first and second target sequences.

In some cases, the closer two genes are together, the less likely that recombination occurs between them. In these cases, the longer the distance between A1 and B2, the higher the probability of fragmentation or recombination between A1 and B2. In some cases, the occurrence of hotspots of recombination may distort the measured recombination frequency for given distances between two loci. For example, in some cases, two loci which are 200 kb apart may have a low recombination frequency. In other cases, two loci also separated by 200 kb but which are hotspots of recombination may recombine at a much higher frequency than the prior case.

The sample can be partitioned (FIG. 3: 340). A digital analysis can be performed, such as digital PCR or droplet-based digital PCR, and compartments with signal for A1, B2, and A1 and B2 can be enumerated (360). An algorithm can be developed and used to determine the probability of fragmentation or recombination between A1 and B2 (380). The algorithm can make use of the number of bases or base pairs between A1 and B2 if known. This method can be used to determine the extent of fragmentation of a DNA or RNA, or any nucleic acid molecule type described herein in a given sample. In some cases, the method may comprise determining a fragmentation value by analyzing the number of partitions that comprise a single marker, e.g., A1, B1, A2, or B2. In some cases, compartments containing only a single marker (e.g., A1) may contain a nucleic acid strand that originally contained such marker (e.g. A1 and a second marker, e.g., A2, B2), but that is now fragmented. If the number of partitions that contain signal from both A1 and B2 is greater than the number of partitions one would expect if A1 and B2 are on different fragments, this observation can indicate that A1 and B2 are linked.

The methods provided herein can be used to determine if one or more molecular or genetic markers are linked. The methods provided herein can be used to determine if one or more molecular or genetic markers are unlinked. The methods provided herein can be used to determine the distance between one or more molecular or genetic markers in a genome. The above methods can also be used on a nucleic acid (e.g., DNA or RNA) of sample to ensure or determine that DNA or RNA is of high enough molecular weight that linkage information is preserved in the sample.

In any of the methods described herein making use of DNA or RNA, an assay can be performed to estimate the fragmentation of the DNA or RNA in the sample, and the methods can incorporate the information on fragmentation of the DNA or RNA. In another embodiment, results of an assay can be normalized based on the extent of fragmentation of DNA or RNA in a sample.

Alternatively, in some application of the methods provided herein, nucleic acid fragmentation or recombination can be measured by, e.g., gels, a Bioanalyzer, or size exclusion chromatography. In some cases, methods described herein may be combined to determine nucleic acid fragmentation or recombination. In some cases, combined methods may be used, for example measuring recombination using ddPCR and a gel. In some cases, ddPCR and a Bioanalyzer may be used. In some cases, ddPCR and size exclusion chromatography may be included.

C. Molecular and Genetic Markers

Variations found in molecular and genetic markers may provide a means for distinguishing genomes, sequence targets such as genomic segments containing particular gene or haplotypes in linkage disequilibrium, or viral isolates. Examples of such genetic variation markers include, but are not limited to, polymorphisms such as: restriction fragment length polymorphisms, single nucleotide DNA polymorphisms, single nucleotide cDNA polymorphisms, single nucleotide RNA polymorphisms, insertions, deletions, inversions, rearrangements, large-scale structural variations, indels, microsatellite repeats (simple sequence repeats), minisatellite repeats (variable number of tandem repeats), short tandem repeats, transposable elements, randomly amplified polymorphic DNA, and amplification fragment length polymorphism.

In some applications of the methods one type of molecular markers or genetic variation markers provide herein is analyzed. In other applications of the methods one or more type of molecular markers or genetic variation markers provide herein are analyzed. In some applications of the methods at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 markers are analyzed. In some applications of the methods at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 markers in linkage disequilibrium are analyzed. In some applications of the methods at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 markers in not in linkage disequilibrium are analyzed. In some applications of the methods at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 markers in both not in linkage disequilibrium and in linkage disequilibrium are analyzed.

In some applications of the methods, the markers analyzed by the methods can distinguish between two or more parental strains. In some applications of the methods, the markers analyzed by the methods can distinguish between two or more viral strains. In some applications of the methods, the markers analyzed by the methods can distinguish between two or more viral species. In some applications of the methods, the markers analyzed by the methods can distinguish between two or more viral subspecies. In some applications of the methods, the markers analyzed by the methods can distinguish between two or more viral genera. In some applications of the methods, the markers analyzed by the methods can distinguish between two or more recombination sites in one or more genomes. In some applications of the methods, the markers analyzed by the methods can be used to discover new recombination sites in one or more genomes. In some applications of the methods, the markers analyzed by the methods can be used to discover new hot spots (e.g. high recombination rate) recombination sites in one or more genomes. In some applications of the methods, the markers analyzed by the methods can be used to discover new cold spots (e.g. low recombination rate) recombination sites in one or more genomes.

In some applications of the methods, the markers can be outside a recombination site but known to be linked to the recombination site. For example the makers being analyzed can be, e.g., less than about 10, 9, 8, 7, 6, 5, 4, 5, 2, 1, 0.7, 0.5, 0.3, 0.2, 0.1, 0.05, or 0.01 megabases apart; or that are very near each other on the polynucleotide, e.g., less than about 10, 9, 8, 7, 6, 5, 4, 3, 2, or 1 kilobase apart. In some cases, the method is useful for analyzing markers that are very close to each other on the polynucleotide, e.g., within about 1, 10, 20, 30, 40, 50, 60, 70, 80, 90, 100, 200, 300, 400, 500, 600, 700, 800, 900, or 950 base pairs (bp's) apart. In some cases, the method is useful for analyzing markers that are separated by zero (0) base pairs. In some cases, the method can be applied to identical, nearly identical, and completely different molecular or genetic variation markers.

D. Devices

1. Droplet Compartment Generation

The present disclosure includes compositions and methods for the detection and analysis of genetic material such nucleic acids, and using droplet digital PCR. Droplet digital PCR uses microfluidics to generate droplet compartments containing the macromolecules of interest and the molecular components, enzymes and environment necessary to carry out an assay.

The droplets described herein include emulsion compositions (or mixtures of two or more immiscible fluids) described in U.S. Pat. No. 7,622,280, and droplets generated by devices described in International Application Publication No. WO/2010/036352, first inventor: Colston, each of which is hereby incorporated by reference in its entirety. The term emulsion, as used herein, generally refers to a mixture of immiscible liquids (such as oil and water). Oil-phase and/or water-in-oil emulsions allow for the compartmentalization of reaction mixtures within aqueous droplets. In some applications, the emulsions comprise aqueous droplets within a continuous oil phase. In other embodiments, the emulsions provided herein are oil-in-water emulsions, wherein the droplets are oil droplets within a continuous aqueous phase. The droplets compartments provided herein are designed to prevent mixing between compartments, with each compartment protecting its contents from evaporation and coalescing with the contents of other compartments.

In some applications of the methods, the aqueous phase can also comprise additives including, but not limited to, non-specific background/blocking nucleic acids (e.g., salmon sperm DNA), biopreservatives (e.g., sodium azide), PCR enhancers (e.g., Betaine, Trehalose, etc.), and inhibitors (e.g., RNAse inhibitors). In some applications of the methods a GC-rich additive comprising, e.g., Betaine and DMSO, is added to samples assayed in the methods provided herein.

The mixtures or emulsions described herein can be stable or unstable. In some applications the emulsions are relatively stable and have minimal coalescence. Coalescence occurs when small droplets combine to form progressively larger ones. In some embodiments, less than about 0.00001%, 0.00005%, 0.00010%, 0.00050%, 0.001%, 0.005%, 0.01%, 0.05%, 0.1%, 0.5%, 1%, 2%, 2.5%, 3%, 3.5%, 4%, 4.5%, 5%, 6%, 7%, 8%, 9%, or 10% of droplets generated from a droplet generator coalesce with other droplets. The emulsions can also have limited flocculation, a process by which the dispersed phase comes out of suspension in flakes.

Splitting a sample into small reaction volumes as described herein, can enable the use of reduced amounts of reagents, thereby lowering the material cost of the analysis. Reducing sample complexity by partitioning also improves the dynamic range of detection, since higher-abundance molecules are separated from low-abundance molecules in different compartments, thereby allowing lower-abundance molecules greater proportional access to reaction reagents, which in turn enhances the detection of lower-abundance molecules.

In some applications of the methods, droplet compartments can be generated having an average diameter of about 0.001, 0.01, 0.05, 0.1, 1, 5, 10, 20, 30, 40, 50, 60, 70, 80, 100, 120, 130, 140, 150, 160, 180, 200, 300, 400, or 500 microns. Microfluidic methods of producing emulsion droplets using microchannel cross-flow focusing or physical agitation are known to produce either monodisperse or polydisperse emulsions. In some applications of the methods, the droplet compartments are monodisperse droplets. In some applications of the methods, the droplet compartments are generated such that the size of the droplets compartments does not vary by more than plus or minus 5% of the average size of the droplets. In some applications of the methods, the droplet compartments are generated such that the size of the droplets does not vary by more than plus or minus 2% of the average size of the droplets. In some applications, a droplet generator can generate a population of droplets from a single sample, wherein none of the droplets vary in size by more than plus or minus 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% of the average size of the total population of droplets.

In some applications of the methods, the flow rates of the oil phase, the aqueous phase, or both may be utilized to control the number of droplets generated per time or per sample volume. In some cases, flow rates may be controlled by active pumping, by one or more pressure gradients, by vacuum, or combinations thereof. In some cases, flow rates may be controlled by fluid viscosity, channel drag, fluid temperature, channel temperature or combinations thereof. In some applications, the size and geometry of one or more channels in the droplet generator may control the number of droplets generated per time or per sample volume. In some applications, the angle of the intersection between the one or more aqueous fluid channels and the oil channel may control the number of droplets generated per time or per sample volume.

In some cases, about 1,000 droplets may be formed per second. In some cases, more than about 1,000 droplets may be formed per second. In some cases, less than about 1,000 droplets may be formed per second. In some cases, about 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, 10,000 droplets may form per second. In some cases, more than about 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, 10,000 droplets may form per second or more. In some cases, less than about 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, 10,000 droplets may form per second or less.

In some cases, the flow rate in the droplet generator may be about 0.00001, 0.00005, 0.0001, 0.0005, 0.001, 0.005, 0.01, 0.05, 0.1, 0.5, 1, 5, 10, 50, 100 mL/min. In some cases, the flow rate in the droplet generator may be more than about 0.00001, 0.00005, 0.0001, 0.0005, 0.001, 0.005, 0.01, 0.05, 0.1, 0.5, 1, 5, 10, 50, 100 mL/min or more. In some cases, the flow rate in the droplet generator may be less than about 0.00001, 0.00005, 0.0001, 0.0005, 0.001, 0.005, 0.01, 0.05, 0.1, 0.5, 1, 5, 10, 50, 100 mL/min or less. In some cases, the flow rate in the droplet generator may be about 0.01 to about 00.1 mL/min. In some cases, the flow rate in the droplet generator may be about 0.0001 to about 10 mL/min. In some cases, the flow rate in the droplet generator may be more than about 0.01 mL/min. In some cases, the flow rate in the droplet generator may be less than about 0.1 mL/min. In some cases, the flow rate in the droplet generator may be continuous. In some cases, the flow rate in the droplet generator may not be continuous.

In some applications of the methods, the droplet compartments can be formed by flowing an oil phase through an aqueous sample. In some applications of the methods, the aqueous phase comprises a buffered solution and reagents for performing a PCR reaction, including nucleotides, primers, probe(s) for fluorescent detection, template nucleic acids, DNA polymerase enzyme, and optionally, reverse transcriptase enzyme.

In some applications of the methods, the aqueous phase comprises a buffered solution and reagents for performing a PCR reaction without solid-state beads, such as magnetic-beads. In some embodiments, the buffered solution can comprise about 1, 5, 10, 15, 20, 30, 50, 100, or 200 mM Tris. In some applications, the concentration of potassium chloride can be about 10, 20, 30, 40, 50, 60, 80, 100, 200 mM. In one application, the buffered solution comprises 15 mM Tris and 50 mM KCl. In some embodiments, the nucleotides comprise deoxyribonucleotide triphosphate molecules, including dATP, dCTP, dGTP, dTTP, in concentrations of about 50, 100, 200, 300, 400, 500, 600, or 700 µM each. In some embodiments, dUTP is added within the aqueous phase to a concentration of about 50, 100, 200, 300, 400, 500, 600, or 700, 800, 900, or 1000 µM. In some applications, magnesium chloride ($MgCl_2$) is added to the aqueous phase at a concentration of about 1.0, 2.0, 3.0, 4.0, or 5.0 mM. In one embodiment, the concentration of $MgCl_2$ is 3.2 mM.

A non-specific blocking agent such as BSA or gelatin from bovine skin can be used, wherein the gelatin or BSA is present in a concentration range of approximately 0.1-0.9% w/v. Other possible blocking agents can include beta-lactoglobulin, casein, dry milk, or other common blocking agents. In some applications, preferred concentrations of BSA and gelatin are 0.1% w/v.

Primers for amplification within the aqueous phase can have a concentration of about 0.1, 0.2, 0.3, 0.4, 0.5, 0.6, 0.7, 0.8, 0.9, or 1.0 µM. In one embodiment, the concentration of primers is 0.5 µM. In some applications, the aqueous phase comprises one or more probes for fluorescent detection, at a concentration of about 0.1, 0.2, 0.3, 0.4, or 0.5 µM. In one application, the concentration of probes for fluorescent detection is 0.25 µM. Amenable ranges for target nucleic acid concentrations in PCR are between about 1 pg and about 500 ng.

In some applications, a non-ionic Ethylene Oxide/Propylene Oxide block copolymer is added to the aqueous phase in a concentration of about 0.1%, 0.2%, 0.3%, 0.4%, 0.5%, 0.6%, 0.7%, 0.8%, 0.9%, or 1.0%. Common biosurfactants include non-ionic surfactants such as Pluronic F-68, Tetronics, Zonyl FSN. In one application, Pluronic F-68 is present at a concentration of 0.5% w/v.

In some embodiments magnesium sulfate can be substituted for magnesium chloride, at similar concentrations. A wide range of common, commercial PCR buffers from varied vendors can be substituted for the buffered solution.

The oil phase can comprise a fluorinated base oil which can be additionally stabilized by combination with a fluorinated surfactant such as a perfluorinated polyether. In some embodiments, the base oil can be one or more of HFE 7500, FC-40, FC-43, FC-70, or another common fluorinated oil. In some embodiments, the anionic surfactant is Ammonium Krytox (Krytox-AM), the ammonium salt of Krytox FSH, or morpholino derivative of Krytox-FSH. Krytox-AS can be present at a concentration of about 0.1%, 0.2%, 0.3%, 0.4%, 0.5%, 0.6%, 0.7%, 0.8%, 0.9%, 1.0%, 2.0%, 3.0%, or 4.0% w/w. In some embodiments, the concentration of Krytox-AS is 1.8%. In other applications, the concentration of Krytox-AS is 1.62%. Morpholino derivative of Krytox-FSH can be present at a concentration of about 0.1%, 0.2%, 0.3%, 0.4%, 0.5%, 0.6%, 0.7%, 0.8%, 0.9%, 1.0%, 2.0%, 3.0%, or 4.0% w/w. In some applications, the concentration of morpholino derivative of Krytox-FSH is 1.8%. In some applications, the concentration of morpholino derivative of Krytox-FSH is 1.62%.

The oil phase can further comprise an additive for tuning the oil properties, such as vapor pressure or viscosity or surface tension. Nonlimiting examples include perfluorooctanol and 1H, 1H, 2H, 2H-Perfluorodecanol. In some applications, 1H, 1H, 2H, 2H-Perfluorodecanol is added to a concentration of about 0.05%, 0.06%, 0.07%, 0.08%, 0.09%, 1.00%, 1.25%, 1.50%, 1.75%, 2.00%, 2.25%, 2.50%, 2.75%, or 3.00% w/w. In some applications, 1H, 1H, 2H, 2H-Perfluorodecanol is added to a concentration of 0.18% w/w.

In some applications of the methods, the emulsion is formulated to produce highly monodisperse droplets having a liquid-like interfacial film that can be converted by heating into microcapsules having a solid-like interfacial film; such microcapsules can behave as bioreactors able to retain their contents through a reaction process such as PCR amplification. The conversion to microcapsule form can occur upon heating. For example, such conversion can occur at a temperature of greater than about 50, 60, 70, 80, 90, or 95 degrees Celsius. In some applications this heating occurs using a thermocycler. During the heating process, a fluid or mineral oil overlay can be used to prevent evaporation. Excess continuous phase oil may or may not be removed prior to heating. The biocompatible capsules can be resistant to coalescence and/or flocculation across a wide range of thermal and mechanical processing.

Following conversion, the capsules can be stored at about 3, 4, 5, 6, 7, 8, 9, 10, 15, 20, 25, 30, 35, or 40 degrees, with one embodiment comprising storage of capsules at less than about 25 degrees. In some applications, these capsules are useful in biomedical applications, such as stable, digitized encapsulation of macromolecules, particularly aqueous biological fluids containing a mix of nucleic acids or protein, or both together; drug and vaccine delivery; biomolecular libraries; clinical imaging applications, and others.

The microcapsules can contain one or more nucleic acid probes (e.g., molecular inversion probe, ligation probe, etc.) and can resist coalescence, particularly at high temperatures. Accordingly, PCR amplification reactions can occur at a very high density (e.g., number of reactions per unit volume). In some applications, greater than 100,000, 500,000, 1,000,000, 1,500,000, 2,000,000, 2,500,000, 5,000,000, or 10,000,000 separate reactions can occur per ml. In some applications, the reactions occur in a single well, e.g., a well of a microtiter plate, without inter-mixing between reaction volumes. The microcapsules can also contain other components necessary to enable a PCR reaction to occur, e.g., primers, probes, dNTPs, DNA or RNA polymerases, etc. These capsules exhibit resistance to coalescence and flocculation across a wide range of thermal and mechanical processing.

The compositions described herein include compositions comprising mixtures of two or more immiscible fluids such as oil and water that contain a type of nucleic acid probe (e.g., TaqMan probe, molecular inversion probe, ligation probe, etc.). In some cases, the composition comprises a restriction enzyme described herein, e.g., a droplet comprising a restriction enzyme (e.g., methylation-sensitive enzyme). In other applications, the compositions described herein comprise microcapsules that contain a type of nucleic acid (e.g., TaqMan probe, molecular inversion probe, ligation probe, etc.). Such microcapsules can resist coalescence, particularly at high temperatures, and therefore enable amplification reactions to occur at a very high density (e.g., number of reactions per unit volume).

In some applications, the droplets described herein are generated at a rate of greater than about 1, 2, 3, 4, 5, 10, 50, 100, 200, 300, 400, 500, 600, 700, 800, 900, or 1000 droplets/second. The droplet rate can be about 1-1000, 1-500, 1-250, 1-100 or 1-50 droplets/second.

2. Thermocycler: Digital PCR for Recombination Analysis

A thermocycler (also known as a therma cycler, PCR machine or DNA amplifier) is a device most commonly used to amplify segments of nucleic acid using the polymerase chain reaction (PCR). In general, the device has a thermal block with holes where sample tubes holding the sample and the PCR reaction mixtures can be inserted. The thermocycler device raises and lowers the temperature of the block in discrete, pre-programmed steps to help facilitate the amplification being conducted in the PCR reaction mixtures.

A digital PCR device (e.g., droplet digital PCR device) for use with the methods, compositions, and kits described herein can detect multiple signals (see e.g. U.S. Provisional Patent Application No. 61/454,373, filed Mar. 18, 2011, herein incorporated by reference in its entirety).

Droplet digital PCR can involve the generation of thousands of discrete, robust microdroplet reactors per second. ddPCR can involve standard thermal cycling with installed-base instruments, which can make digital data accessible immediately to researchers. Rapid interrogation of each droplet can yield counts of target molecules present in the initial sample.

An integrated, rapid, flow-through thermal cycler device can be used in the methods described herein. See, e.g., International Application No. PCT/US2009/005317, filed Sep. 23, 2009. In such an integrated device, a capillary is wound around a cylinder that maintains 2, 3, or 4 temperature zones. As droplets flow through the capillary, they are subjected to different temperature zones to achieve thermal cycling. The small volume of each droplet results in an extremely fast temperature transition as the droplet enters each temperature zone.

In general, a thermocycler is used to carry out an amplification reaction that ultimately aids in the detection of the molecular markers or genetic variation marker provide herein, (e.g. SNPs, indels, short tandem repeats, etc.), for example, by the use of PCR, digital PCR, droplet digital PCR (ddPCR) and the like. Specifically in the case ddPCR amplification, the droplet compartments generated (e.g., droplets) are then subjected to a thermocycling reaction to facilitate the PCR reactions within droplet compartments, that most often comprise a target nucleotide, or a probe to the target nucleotide which is capable of hybridizing to a target polynucleotide, the appropriate polymerase enzyme, the appropriate environment for the enzyme (e.g., buffers, salts, etc.) resulting in amplified products (e.g., amplified nucleic acids from samples such as ssDNA, dsDD, ssRNA, dsRNA, mRNA, cDNA or other nucleic acids).

Thermocycling reactions can be performed on samples contained in droplets. The droplets can remain intact during thermocycling. Droplets can remain intact during thermocycling at densities of greater than about 10,000 droplets/mL, 100,000 droplets/mL, 200,000 droplets/mL, 300,000 droplets/mL, 400,000 droplets/mL, 500,000 droplets/mL, 600,000 droplets/mL, 700,000 droplets/mL, 800,000 droplets/mL, 900,000 droplets/mL or 1,000,000 droplets/mL. In other cases, two or more droplets may coalesce during thermocycling. In other cases, greater than 100 or greater than 1,000 droplets may coalesce during thermocycling.

Any DNA polymerase that catalyzes a PCR reaction can be used including, but not limited to, E. coli DNA polymerase, Klenow fragment of E. coli DNA polymerase 1, T7 DNA polymerase, T4 DNA polymerase, Taq polymerase, Pfu DNA polymerase, Vent DNA polymerase, bacteriophage 29, REDTaq™. Genomic DNA polymerase, or sequenase. Preferably, a thermostable DNA polymerase is used. A hot start PCR (using a hot start DNA polymerase, such as an antibody linked DNA polymerase) can also be performed wherein the reaction is heated to 95° C. for two minutes prior to addition of the polymerase or the polymerase can be kept inactive until the first heating step in cycle 1. Hot start PCR can be used to minimize nonspecific amplification. Any number of PCR cycles can be used to amplify the DNA, including, but not limited to, 2, 5, 10, 15, 20, 25, 30, 35, 40, or 45 cycles.

Examples of a polymerase chain reaction (PCR) techniques that can be used with the methods, compositions, and system of the disclosure include, but are not limited to: quantitative PCR, quantitative fluorescent PCR (QF-PCR), multiplex fluorescent PCR (MF-PCR), real time PCR (RT-PCR), real-time reverse-transcriptase polymerase chain reaction (RRT-PCR), single cell PCR, restriction fragment length polymorphism PCR (PCR-RFLP), PCR-RFLP/RT-PCR-RFLP, hot start PCR, nested PCR, in situ polonony PCR, in situ rolling circle amplification (RCA), bridge PCR, picotiter PCR and emulsion PCR. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that can be used herein include those described in U.S. Pat. No. 5,242,794, U.S. Pat. No. 5,494,810, U.S. Pat. No. 4,988,617, and U.S. Pat. No. 6,582,938. In some application of the methods, amplification of target nucleic acids can occur on a bead. In other application of the methods, amplification does not occur on a bead.

The annealing temperature of the primers can be recalculated and increased after any cycle of amplification, including but not limited to about cycle 1, 2, 3, 4, 5, about cycle 6 to about cycle 10, about cycle 10 to about cycle 15, about cycle 15 to about cycle 20, about cycle 20 to about cycle 25, about cycle 25 to about cycle 30, about cycle 30 to about cycle 35, or about cycle 35 to about cycle 40. After the initial cycles of amplification, the 5' half of the primers can be incorporated into the products from each markers of interest; thus the TM can be recalculated based on both the sequences of the 5' half and the 3' half of each primer.

The annealing temperature of the primers can be recalculated and increased after any cycle of amplification, including but not limited to about cycle 1, 2, 3, 4, 5, about cycle 6 to about cycle 10, about cycle 10 to about cycle 15, about cycle 15 to about cycle 20, about cycle 20 to about cycle 25, about cycle 25 to about cycle 30, about cycle 30 to about 35, or about cycle 35 to about cycle 40. After the initial cycles of amplification, the 5' half of the primers can be incorporated into the products from each loci of interest, thus the TM can be recalculated based on both the sequences of the 5' half and the 3' half of each primer.

Depending on the target size of the amplification reaction the number of PCR cycles will vary. Thus, any number of PCR cycles can be used to amplify the target nucleic acid. The number of amplification cycles can be about 1 to about 45, about 10 to about 45, about 20 to about 45, about 30 to about 45, about 35 to about 45, about 10 to about 40, about 10 to about 30, about 10 to about 25, about 10 to about 20, about 10 to about 15, about 20 to about 35, about 25 to about 35, about 30 to about 35, or about 35 to about 40.

Solution and reagents for performing a PCR reaction can include buffers. The buffered solution can comprise about, more than about, or less than about 1, 5, 10, 15, 20, 30, 50, 100, or 200 mM Tris. In some cases, the concentration of potassium chloride can be about, more than about, or less than about 10, 20, 30, 40, 50, 60, 80, 100, 200 mM. The buffered solution can comprise about 15 mM Tris and 50 mM KCl. The nucleotides can comprise deoxyribonucleotide triphosphate molecules, including dATP, dCTP, dGTP, dTTP, in concentrations of about, more than about, or less than about 50, 100, 200, 300, 400, 500, 600, or 700 μM each. In some cases, a non-canonical nucleotide, e.g., dUTP is added to amplification reaction to a concentration of about, more than about, or less than about 50, 100, 200, 300, 400, 500, 600, or 700, 800, 900, or 1000 μM. In some cases, magnesium chloride ($MgC_{12}$) is added to an amplification reaction at a concentration of about, more than about, or less than about 1.0, 2.0, 3.0, 4.0, or 5.0 mM. The concentration of $MgC_{12}$ can be about 3.2 mM.

A non-specific blocking agent such as BSA or gelatin from bovine skin can be used, wherein the gelatin or BSA is present in a concentration range of approximately 0.1 to about 0.9% w/v. Other possible blocking agents can include betalactoglobulin, casein, dry milk, or other common blocking agents. In some cases, preferred concentrations of BSA and gelatin are about 0.1% w/v.

In some applications, an amplification reaction can also comprise one or more additives including, but not limited to, non-specific background/blocking nucleic acids (e.g., salmon sperm DNA), biopreservatives (e.g. sodium azide), PCR enhancers (e.g. Betaine, Trehalose, etc.), and inhibitors (e.g. RNAse inhibitors). The one or more additives can include, e.g., 2-pyrrolidone, acetamide, N-methylpyrolidone (NMP), B-hydroxyethylpyrrolidone (HEP), propionamide, NN-dimethylacetamide (DMA), N-methylformamide (MMP), NN-dimethylformamide (DMF), formamide, N-methylacetamide (MMA), dimethyl sulfoxide (DMSO), polyethylene glycol, betaine, tetramethylammonium chloride (TMAC), 7-deaza-2'-deoxyguanosine, bovine serum albumin (BSA), T4 gene 32 protein, glycerol, or nonionic detergent (Triton X-100, Tween 20, Nonidet P-40 (NP-40), Tween 40, SDS (e.g., about 0.1% SDS)), salmon sperm DNA, sodium azide, betaine (N,N,N-trimethylglycine; [carboxymethyl]trimethylammonium), formamide, trehalose, dithiothreitol (DTT), betamercaptoethanol (BME), a plant polysaccharide, or an RNase inhibitor.

In some applications, an amplification reaction comprises one or more buffers. The one or more buffers can comprise, e.g., TAPS, bicine, Tris, Tricine, TAPSO, HEPES, TES, MOPS, PIPES, cacodylate, SSC, ADA, ACES, cholamine chloride, acetamidoglycine, glycinamide, maleate, phosphate, CABS, piperidine, glycine, citrate, glycylglycine, malate, formate, succinate, acetate, propionate, pyridine, piperazine, histidine, bis-tris, ethanolamine, carbonate, MOPSO, imidazole, BIS-TRIS propane, BES, MOBS, triethanolamine (TEA), HEPPSO, POPSO, hydrazine, Trizma (tris), EPPS, HEPPS, bicine, HEPBS, AMPSO, taurine (AES), borate, CHES, 2-amino-2-methyl-1-propanol (AMP), ammonium hydroxide, methylamine, or MES.

In some cases, a non-ionic Ethylene Oxide/Propylene Oxide block copolymer is added to an amplification reaction in a concentration of about 0.1%, 0.2%, 0.3%, 0.4%, 0.5%, 0.6%, 0.7%, 0.8%, 0.9%, or 1.0%. Common biosurfactants include non-ionic surfactants such as Pluronic F-68, Tetronics, Zonyl FSN. Pluronic F-68 can be present at a concentration of about 0.5% w/v.

In some applications, magnesium sulfate can be substituted for magnesium chloride, at similar concentrations. A wide range of common, commercial PCR buffers from varied vendors can be substituted for the buffered solution.

3. Digital Detector

Generally, the amplification reaction used with the methods, compositions, and systems of the disclosure will generate one or more signals that will be detected by a detector device (e.g., an optical reader or the like).

In some applications of the methods, the signals generated will be a fluorescent signal. Detection of a fluorescent signal from an amplification reaction can be achieved using a variety of detector devices. In general, such detector devices will be equipped with a module to generate excitation light that can be absorbed by a fluorescer, as well as a module to detect light emitted by the fluorescer.

In some applications of the methods, one or more samples contained within the compartments may be detected by the detector device. For example, samples can be allocated in plastic tubes that are placed in a detector that measures bulk fluorescence from plastic tubes from one or more samples. In applications of the methods, one or more samples (such as droplet compartments) can be partitioned into one or more wells of a plate, such as a 96-well or 384-well plate, and fluorescence of individual wells may be detected using a fluorescence plate reader.

In some application of the methods, the detector further comprises sample handling capabilities, with means for implementing the individual droplets to enter the detector, undergo detection, and then exiting the detector. For example, a flow cytometry device can be adapted for use in detecting fluorescence from droplet samples. In some cases, a microfluidic device equipped with pumps to control droplet movement is used to detect fluorescence from droplets in single file. In some cases, droplets are arrayed on a two-dimensional surface and a detector moves relative to the surface, detecting fluorescence at each position containing a single droplet.

In some applications of the methods, following acquisition of signal detection data, a computer processor driven by computer-executable logic can be used to store and process the data. A processor comprising computer-executable logic can be employed to perform such functions as subtraction of background fluorescence, assignment of target and/or reference sequences, and quantification of the data. For example, the number of droplets containing fluorescence corresponding to the presence of a suspected viral recombinant in the sample can be counted and compared to the number of droplets containing fluorescence corresponding to the presence of chromosome not suspected to be a viral recombinant.

A processor directed by computer-executable logic can be used for displaying, storing, retrieving, or calculating data from the molecular signature profiling of a viral recombinant. A processor directed by computer-executable logic can be used for displaying, storing, retrieving, or calculating raw data from nucleic acid and/or protein expression describing a virus particle. A processor directed by computer-executable logic can be used for displaying, storing, retrieving, or calculating raw data to determine viral load, growth rate, recombination rate, and the like.

D. Assay Readouts

1. Detection Primers, Probes, Labels, and Dyes

Amplification reaction used with the methods, compositions, and systems of the disclosure can generate one or more signals. In some aspects of the methods, labels are used in or after the amplification reaction to generate the signal. In some aspects of the methods, dyes are used in or after the amplification reaction to generate the signal.

Primers

In some applications of the method, the primers are designed to detect a particular maker. For example, primers can be designed to bind to and distinguish between two or more polymorphisms. Examples of such targeted primers, are primers designed to recognize restriction fragment length polymorphisms, single nucleotide DNA polymorphisms, single nucleotide cDNA polymorphisms, single nucleotide RNA polymorphisms, single nucleotide RNA polymorphisms, insertions, deletions, indels, microsatellite repeats (simple sequence repeats), minisatellite repeats (variable number of tandem repeats), short tandem repeats, transposable elements, randomly amplified polymorphic DNA, and amplification fragment length polymorphism. In some cases, the primers may be designed to produce a specific amplicon of a particular size. When detected with a probe (e.g., fluorescent label), the amplicon may fluoresce at a different amplitude depending on the length of the amplicon. Such process may be useful for the assays provided herein, particularly where two factors (e.g., loci, alleles, etc.) are differentiated based on the amplitude of a signal rather than solely on the color of signal. For example, the primers may be designed to produce relatively short amplicons when amplifying locus 1 and longer amplicons when amplifying a second locus on the same strand. In another case, the primers may be designed to produce relatively short amplicons when amplifying a first locus and longer amplicons when amplifying an allele or genetic variant of the first locus.

Primers can be designed according to known parameters for avoiding secondary structures and self-hybridization. Different primer pairs can anneal and melt at about the same temperatures, for example, within about 1, 2, 3, 4, 5, 6, 7, 8, 9 or 10° C. of another primer pair. In some cases, greater than about 1, 2, 3, 4, 5, 6, 7, 8, 9, 10, 15, 20, 25, 30, 35, 40, 45, 50, 100, 200, 500, 1000, 5000, 10,000 or more primers are initially used. Such primers may be able to hybridize to genetic targets and markers described herein. In some applications, about 2 to about 10,000, about 2 to about 5,000, about 2 to about 2,500, about 2 to about 1,000, about 2 to about 500, about 2 to about 100, about 2 to about 50, about 2 to about 20, about 2 to about 10, or about 2 to about 6 primers are used.

Primers can be prepared by a variety of methods including, but not limited to, cloning of appropriate sequences and direct chemical synthesis using methods well known in the art (Narang et al., Methods Enzymol. 68:90 (1979); Brown et al., Methods Enzymol. 68:109 (1979)). Primers can also be obtained from commercial sources such as Integrated DNA Technologies, Operon Technologies, Amersham Pharmacia Biotech, Sigma, and Life Technologies. The primers can have an identical melting temperature. The melting temperature of a primer can be about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 81, 82, 83, 84, or 85° C. In some applications, the melting temperature of the primer is about 30 to about 85° C., about 30 to about 80° C., about 30 to about 75° C., about 30 to about 70° C., about 30 to about 65° C., about 30 to about 60° C., about 30 to about 55° C., about 30 to about 50° C., about 40 to about 85° C., about 40 to about 80° C., about 40 to about 75° C., about 40 to about 70° C., about 40 to about 65° C., about 40 to about 60° C., about 40 to about 55° C., about 40 to about 50° C., about 50 to about 85° C., about 50 to about 80° C., about 50 to about 75° C., about 50 to about 70° C., about 50 to about 65° C., about 50 to about 60° C., about 50 to about 55° C., about 52 to about 60° C., about 52 to about 58° C., about 52 to about 56° C., or about 52 to about 54° C.

The lengths of the primers can be extended or shortened at the 5' end or the 3' end to produce primers with desired melting temperatures. One of the primers of a primer pair can be longer than the other primer. The 3' annealing lengths of the primers, within a primer pair, can differ. Also, the annealing position of each primer pair can be designed such that the sequence and length of the primer pairs yield the desired melting temperature. An equation for determining the melting temperature of primers smaller than 25 base pairs is the Wallace Rule (Td=2(A+T)+4(G+C)). Computer programs can also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The TM (melting or annealing temperature) of each primer can be calculated using software programs such as Net Primer.

In some cases, two alleles with substantially similar sequences may exist within a sample. In some cases, two alleles may differ in size by 1, 2, 3, 4, 5, 6, 7, 8, 9, 10, 11, 12, 13, 14, 15, 16, 17, 18, 19, 20 kb. In some cases, two alleles may differ in size by less than 2, 3, 4, 5, 6, 7, 8, 9, 10, 11, 12, 13, 14, 15, 16, 17, 18, 19, 20 kb or less. In some cases, fluorescence reporters may be designed to target only one of the two sequences that are substantially similar. In some cases, the fluorescent reporter may not cross-react with the non-target allele. In some cases, the fluorescent reporter may cross-react with the non-target allele. In some cases, high rates of cross-reactivity may result in droplets with different levels of fluorescence intensity or amplitude above background levels.

Probes

In some aspects of the methods probes are used in or after the amplification reaction to generate one or more signals. Depending on the application of the methods a certain type of probe may be desirable. In some applications of the methods the probe is a random sequence or universal probe. The universal probe can be designed to ensure that it does not bind the target polynucleotide in an assay or to other non-target polynucleotides likely to be in a sample (e.g., genomic DNA outside the region occupied by the target polynucleotide).

In some applications of the method the probe is a targeted sequence. For example, probes can be designed to bind to and distinguish between two or more polymorphisms. Examples of target polymorphisms probes are probes designed to recognize restriction fragment length polymorphisms, single nucleotide DNA polymorphisms, single nucleotide cDNA polymorphisms, single nucleotide RNA polymorphisms, single nucleotide RNA polymorphisms, insertions, deletions, indels, microsatellite repeats (simple sequence repeats), minisatellite repeats (variable number of tandem repeats), short tandem repeats, transposable elements, randomly amplified polymorphic DNA, and amplification fragment length polymorphism. In some cases, two probes with two different colors are used to distinguish between two or more polymorphisms. In some cases, a probe of a single color is used to distinguish between two polymorphisms because it is designed to emit a signal with a different amplitude depending on which polymorphism it binds. In some cases, it will bind more weakly to one of the polymorphisms, thereby producing a signal with a reduced amplitude.

Labels and Dyes

In some applications of the methods labels are used in or after the amplification reaction to generate one or more signals. The label can be at the 5' end of a probe, 3' end of the probe, at both the 5' and 3' end of a probe, or internal to the probe. A unique label can be used to detect each different locus in an experiment. Non-limiting examples of labels that can be used with the methods, composition and systems provided herein include but are not limited to: label (fluorophore, dye) used on a probe (e.g., a Taqman probe) to detect a target nucleic acid sequence or reference nucleic acid sequence in the methods described herein can be, e.g., 6-carboxyfluorescein (FAM), tetrachlorofluorescin (TET), 4,7,2'-trichloro-7'-phenyl-6-carboxyfluorescein (VIC), HEX, Cy3, Cy 3.5, Cy 5, Cy 5.5, Cy 7, tetramethylrhodamine, ROX, and JOE. The label can be an Alexa Fluor dye, e.g., Alexa Fluor 350, 405, 430, 488, 532, 546, 555, 568, 594, 633, 647, 660, 680, 700, and 750. The label can be Cascade Blue, Marina Blue, Oregon Green 500, Oregon Green 514, Oregon Green 488, Oregon Green 488-X, Pacific Blue, Rhodamine Green, Rhodol Green, Rhodamine Green-X, Rhodamine Red-X, and Texas Red-X.

In some aspects of the methods Taqman probes are used in or after the amplification reaction to generate one or more signals. A probe, (e.g., a Taqman probe), can comprise a quencher, e.g., a 3' quencher. The 3' quencher can be, e.g., TAMARA, DABCYL, BHQ-1, BHQ-2, or BHQ-3. In some cases, a quencher used in the methods provided herein is a black hole quencher (BHQ). In some cases, the quencher is a minor groove binder (MGB). In some cases, the quencher is a fluorescent quencher. The detectable probe can comprise a fluorescer and a quencher molecule. In other cases, the quencher is a non-fluorescent quencher (NFQ).

A probe can be about, or at least about, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases long. A probe can be about 8 to about 40, about 10 to about 40, about 10 to about 35, about 10 to about 30, about 10 to about 25, about 10 to about 20, about 15 to about 40, about 15 to about 35, about 15 to about 30, about 15 to about 25, about 15 to about 20, about 18 to about 40, about 18 to about 35, about 18 to about 30, about 18 to about 25, or about 18 to 22 bases long.

Figure 6:
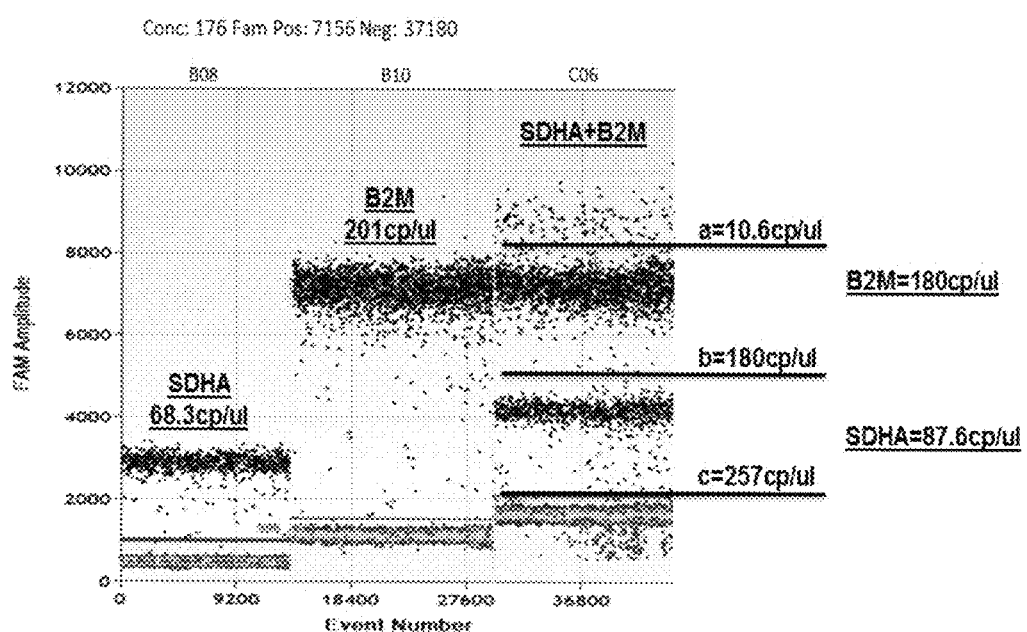
FIG. 6 illustrates a gene expression assay of cDNA, reverse transcribed from total brain RNA before partitioning wherein a multiplexing method using amplitude for marker identification detects SDHA (succinate dehydrogenase) and B2M (beta2-microglobulin) either separately or together in the same ddPCR reaction.
Figure 7:
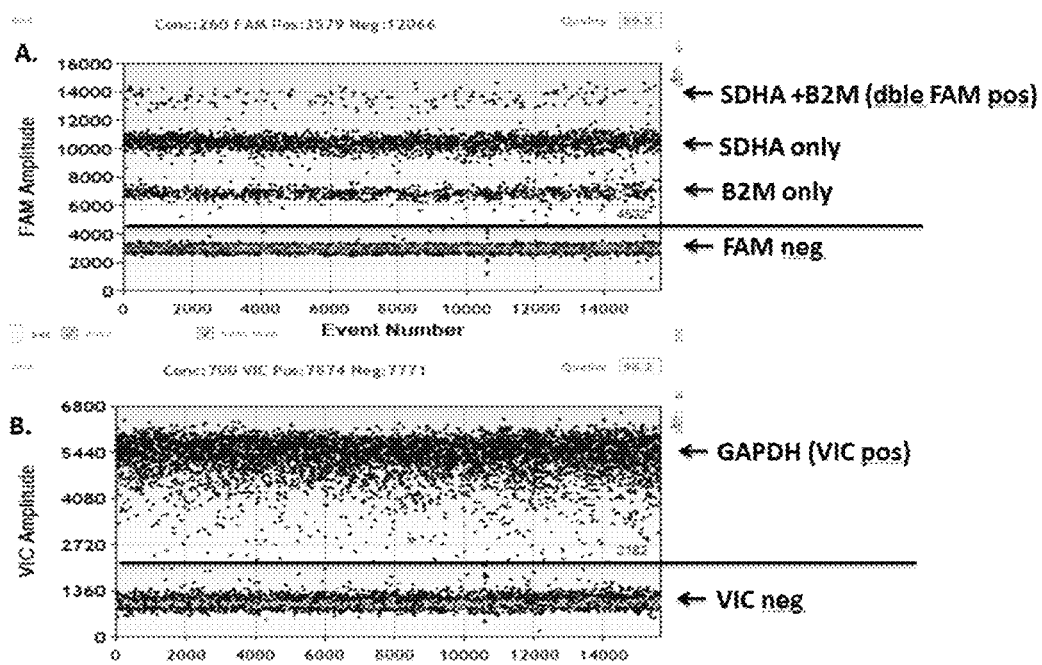
FIGS. 7A and 7B illustrate a multiplexing method of determining viral recombination rate using both amplitude and color for marker identification, wherein a triplex assay comprises GAPDH is detected in VIC and both B2M and SDHA are detected in FAM at different FAM amplitudes.
Figure 12:
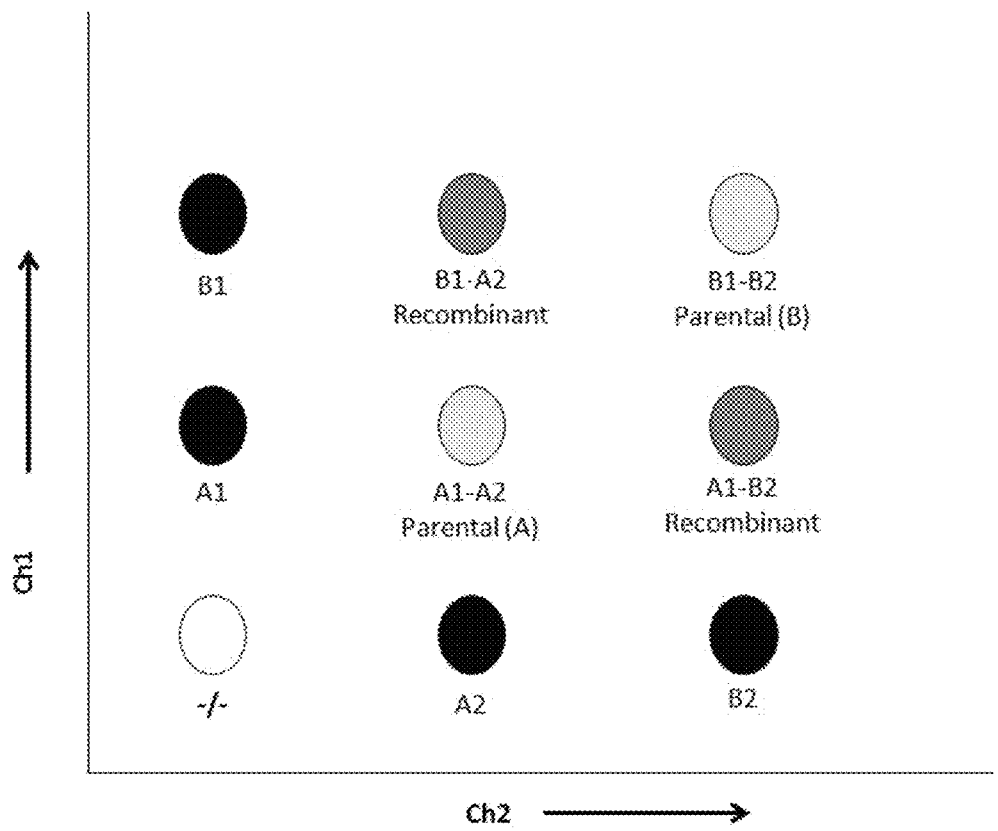
FIG. 12 illustrates an alternative multiplexing method of determining viral recombination rate using a two marker identification scheme, wherein color distinguishes alleles and amplitude distinguishes parental loci.

When detecting a signal from a given probe, primer, label or dye used with the methods of the disclosure the signal can be distinguished by its amplitude intensity (e.g., FIG. 6), by its color, or both amplitude intensity and color (e.g., FIGS. 7, 9 and 12).

2. Multiplexing

A set (e.g., one or more) different detection probes can be used in the method; for example, multiplexing using two or more detection probes can be used to increase the sensitivity of the detection methods and/or increase the number of target nucleic acids detected. In some applications various means of amplitude modulation can be employed to multiplexing in the assays disclosed herein. For example, amplitude modulation can include but is not limited to amplicon size, primer, probe, primer/probe, a mix of fluorophores, such as, for example ~50:50 mix of FAM & HEX (or VIC) probes, etc or any combination thereof. For instance, the concentration of primer will affect efficiency and extent of amplification, translating into fluorescence amplitude differences. The latter is the characteristic amplitude for a particular species to be detected.

Amplitude modulation may be employed in multiplexing assays, wherein two different signal intensities may distinguish two different alleles or two different loci. The length of the amplicon may affect the amplitude or intensity of the signal (e.g., fluorescent marker). In some cases, a set of oligonucleotide sequences may be designed to amplify regions of different lengths, for example, two different loci. In these cases, a single fluorescent marker, FAM may be utilized to probe a viral sample. In these cases, different amplitudes or intensities of FAM may result, and thus identify the two different loci.

A probe set can be one or more probes comprised of about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 different detection labels. A probe set can be one or more probes comprising of about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 different probe types and about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 different detection labels.

The methods provide herein also provide for the recombination assays to be multiplexed. A given probe can have about 1, 2, 3, 4, 5, 6, 7, 8, 9, 10 different detection labels attached. For example, two or more colors can be used in the methods provided herein can be a combination of: FAM: BHQ and NFQ-MGB assays; VIC:NFQ-MGB, TAMRA. HEX:BHQ. 5' and 3' labeling can be used, and an internal labeled dye can be used. In some cases, the number of colors used in the methods provided herein is greater than two, e.g., greater than 3, 4, 5, 6, 7, 8, 9, 10, 11, 12, 13, 14, 15, 16, 17, 18, 19, or 20 colors.

FIG. 6 shows one application of a multiplex experiment for a gene expression assay of cDNA using ddPCR and amplitude intensity of one or more fluorophores. Total brain RNA (Ambion) is obtained and subjected to a reverse transcription reaction in order to generate cDNA. The cDNA is then partitioned (e.g., using a droplet generator) into individual compartments (e.g., droplets). The graph shows measurements of the numbers of droplets that are positive and negative for each fluorophore: succinate dehydrogenase (SDHA), beta-2-microglobulin (B2M) and combination of SDHA and B2M in a given sample. Each droplet in a sample is plotted on a graph of amplitude intensity (e.g., FAM amplitude) on the y-axis versus droplet number (e.g., event number) on the x-axis. All positive droplets above a given threshold intensity (indicated by the bolded line) are scored as positive and assigned a value of FAM amplitude. All negative droplets (those below the threshold) are scored as negative, and each is assigned a value of zero. The readout of the different fluorophore SDHA, B2M and combination of SDHA and B2M are distinguished by the level of intensity of their amplitude. The fraction of positive droplets is then fitted to a Poisson distribution to determine the absolute number of the target DNA molecule in the input reaction mixture in units of copies/µl (e.g., cp/µl). The total number of copies/µl of B2M and SDHA markers can be calculated from such analysis.

Figure 9A:
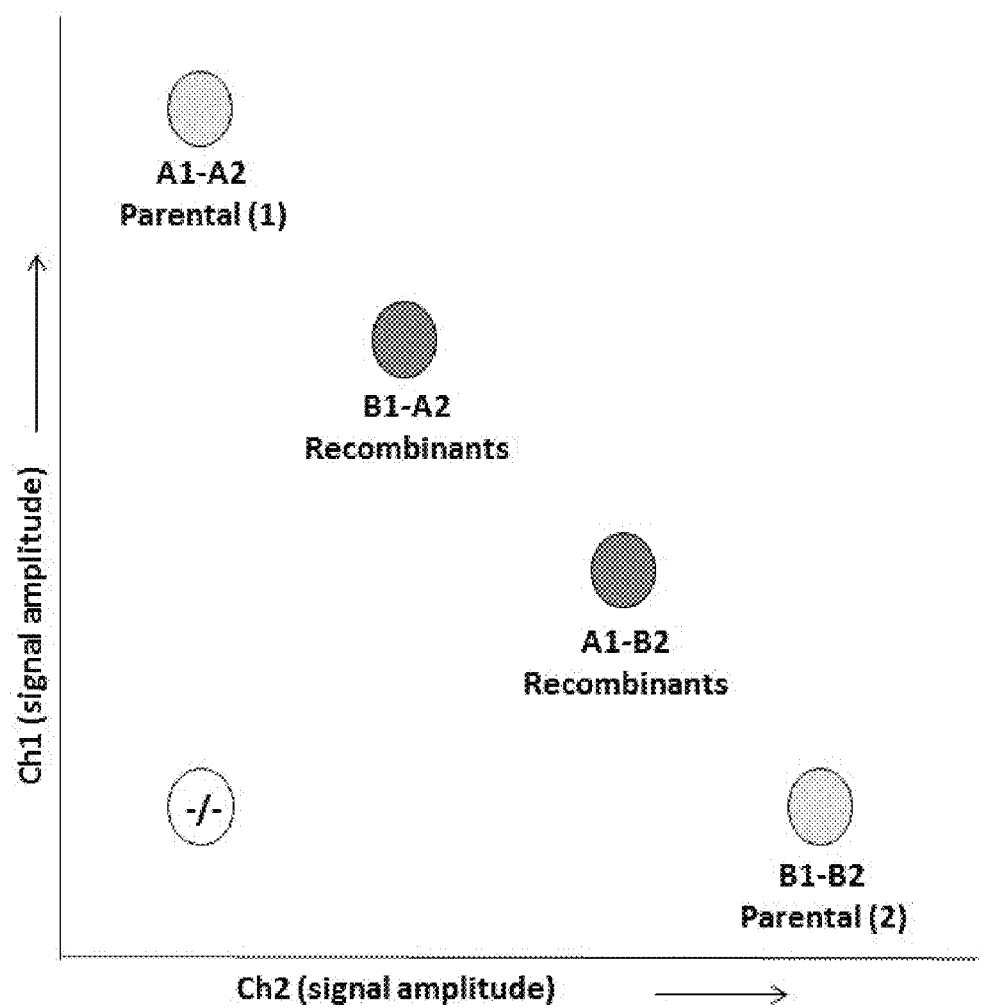
FIGS. 9A, 9B, and 9C illustrate a multiplexing method of determining viral recombination rate using a two marker identification scheme, wherein amplitude distinguishes loci and color distinguishes parental genomes (or alleles). 9A represents very high dilution schemes (0.01 genome copies/droplet) with very large numbers of droplets (e.g. >1M) with no fragmentation, 9B represents high dilution schemes with some fragmentation, and 9C represents low dilution schemes. Not all possible species that could be present in a designated cluster are shown.
Figure 9B:
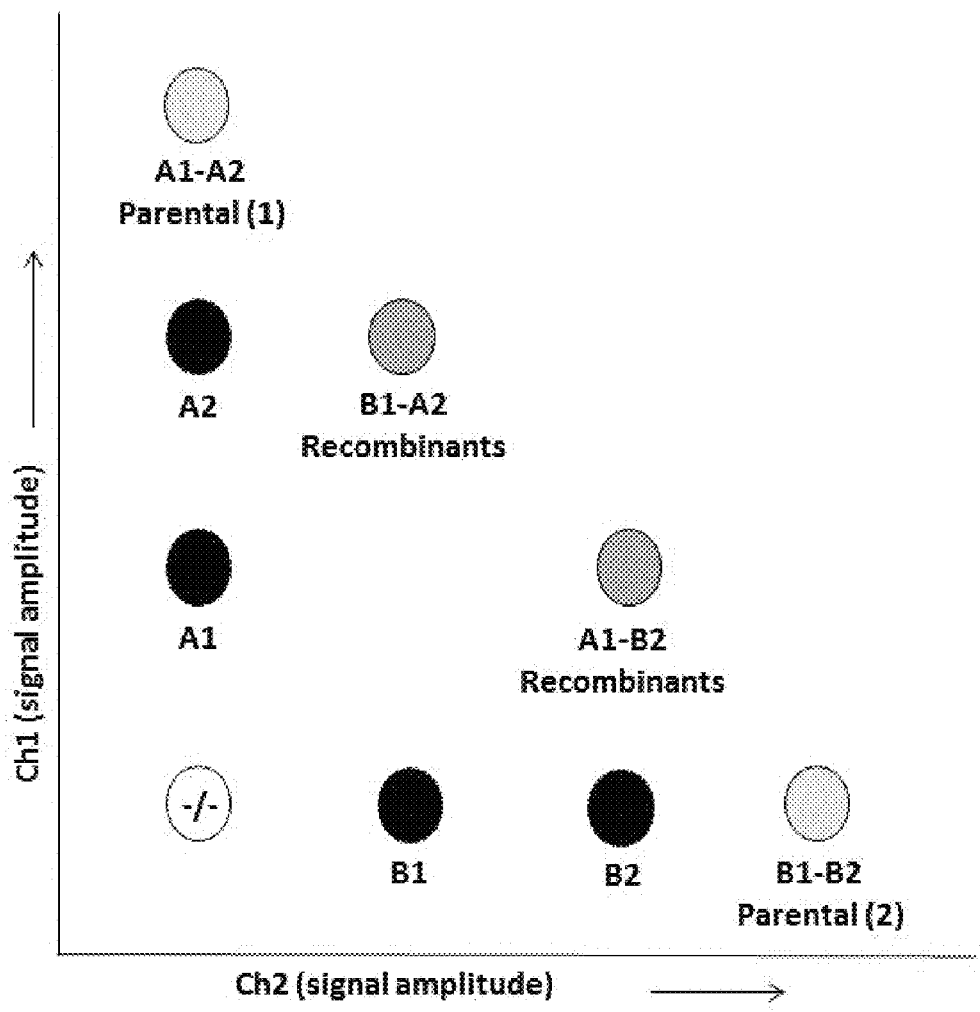
Figure 9C:
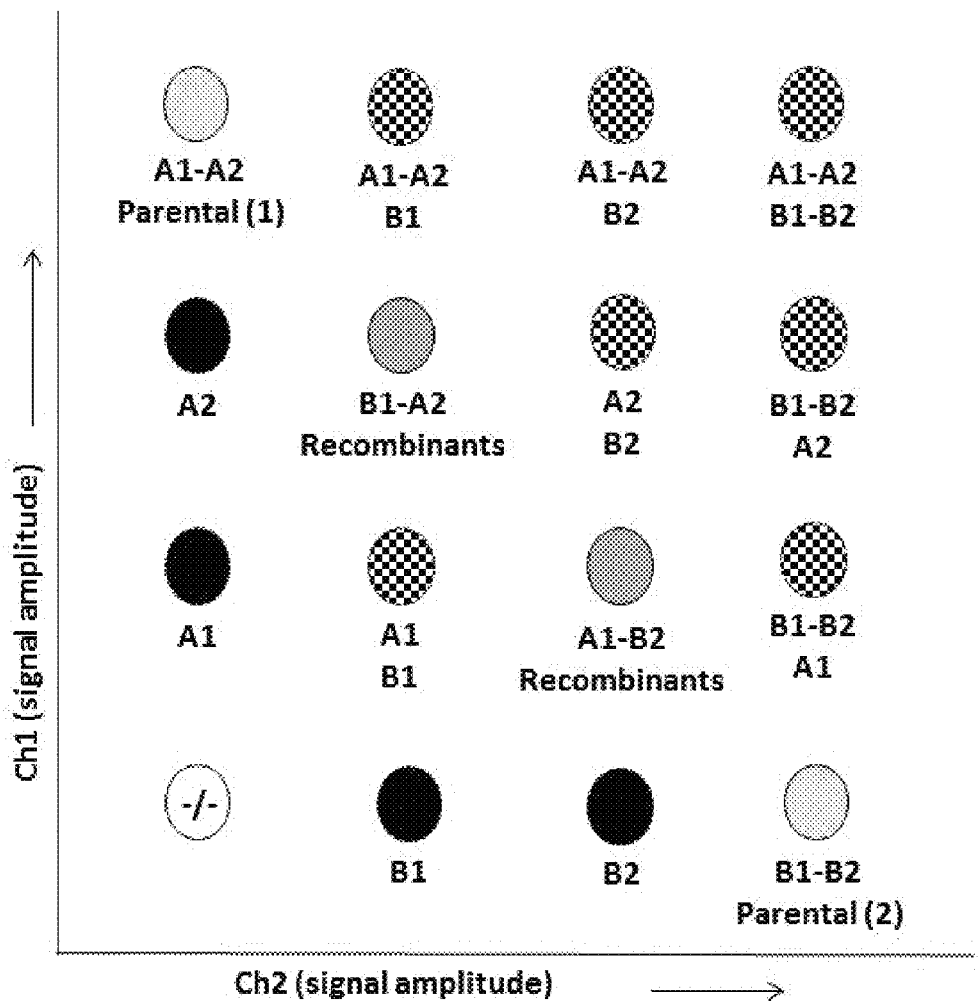

FIG. 9A-C shows one application of a multiplex experiment for a recombination assay using ddPCR between two parental strains such as those depicted in FIG. 8. FIG. 8 illustrates Strain A wherein A1 is labeled with low amplitude FAM and A2 is labeled with high amplitude FAM; and Strain B, wherein B1 is labeled with low amplitude HEX (or VIC) and B2 is labeled with high amplitude HEX (or VIC). Using this marker scheme, parental strains are identified using the fluorescence color (e.g., FAM or HEX) and individual markers (e.g. loci) on the same parental strain are identified using amplitude intensity (e.g., high or low).

Amplified markers are viewed in a 2-D plot (FIGS. 9A, 9B, 9C) in which Ch1 fluorescence level is plotted versus Ch2 fluorescence level for each droplet. One or more droplets having the same Ch1 fluorescence level and Ch2 fluorescence level may form a cluster. A cluster may represent one or more droplets having the same Ch1 fluorescence level and Ch2 fluorescence level. A cluster may represent one or more droplets having the same molecules. A cluster may represent one or more droplets having different molecules. Different combinations of two fluorescent colors and two amplitude intensities may generate additional clusters. More than two fluorescent colors, more than two amplitude intensities, more than two parental strains or combinations thereof may increase the number of clusters than appear on a cluster plot. Cluster plots may be 3D plots.

Figure 10:
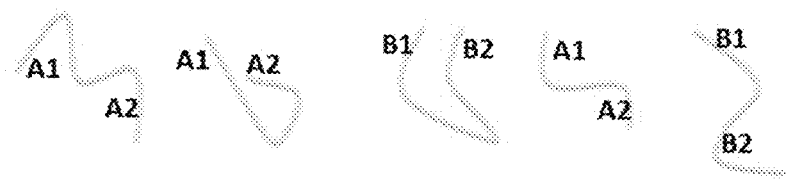
FIGS. 10A, 10B, and 10C illustrate markers (A1, A2 and B1, B2) after a recombination event. 10A illustrates both markers of one parental genome located in a single full-length molecule prior to recombination. 10B illustrates a mixture of both parental and recombinant full length molecules generated from a recombination event. 10C illustrates cases wherein fragments are present.
Figure 10:
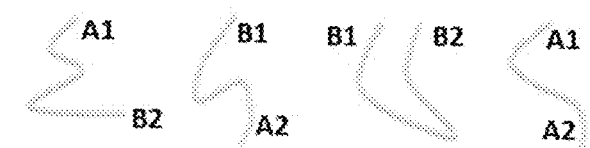
Figure 10:
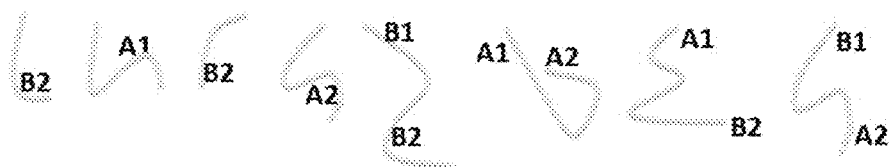

At very high dilutions (e.g., high numbers of droplets and low numbers of copies per droplet), see FIG. 9A, droplets are clustered into 5 different groups: 1 group is assayed as negative (−/−) or having no markers detected, 2 different groups for the parentals (A1−A2 and B1−B2, see also FIG. 10A) and 2 different groups for the recombinants (A1−B2 and B1−A2, see also FIG. 10B). At high dilutions and low levels of fragmentation, see FIG. 9B, additional clusters arise containing fragments A1 only, A2 only, B1 only, and B2 only, see also FIG. 10C. The concentration of clusters A1, A2, B1, and B2 can be used to calculate the extent of fragmentation. Extent of fragmentation may be used to correct the total number of genomes in a sample by eliminating the number of by chance co-localizations. At low dilutions (e.g., high numbers of copies for each droplet), additional clusters may arise, see FIG. 9C. At these dilution conditions, it may be possible that droplets containing parental or recombinant molecules may also contain fragments. For example, an A1−A2 droplet may contain A1 and A2 fragments. The same is true for the B1−B2, A1−B2, and B1−A2 partitions. Four groups are detected as having three different markers: A1−A2, B1 (frag) or A1−A2, B2 (frag) or B1−B2, A1 (frag) or B1−B2, A2 (frag). Note that it is also possible that A1−A2, B1 is actually B1−A2, A1 (frag) or even A1 (frag), A2 (frag), B1 (frag); that A1−A2, B2 (frag) is actually A1−B2, A2 (frag) or A1 (frag), B2 (frag); A2 (frag). One group is detected having four different markers A1+B1, A2+B2, which could reflect four different fragments, or two strands of nucleic acids such as A1−A2 and B1−B2, or other combinations. The nine groups at high dilution or sixteen groups at low dilutions can be distinguished by their color, which is generated from their different Ch1 and Ch2 fluorescence intensities and/or by comparing their amplitude intensities.

In some case, depending on the upstream preparation method used in the assay, a given 2D cluster, may contain other combinations of target molecules than usual majority species. For example, during preparations that involve high fragmentation of the molecule (e.g. A1−B2 could also be A1, B2 in unlinked configuration). This can be determined using the fragmentation algorithm provided herein and in related applications U.S. application Ser. No. 13/385,277.

FIG. 11 shows one application of a multiplex experiment of a recombination frequency assay using ddPCR between two parental strains where the 2 markers (e.g., loci) on a single parental strain are distinguished by color and the parental strains themselves are distinguished by amplitude. FIG. 11 shows the assignment of molecular markers (with A1 labeled with low intensity fluorescence FAM and A2 labeled with low intensity fluorescence HEX (or VIC) in Strain A; and Strain B, with B1 labeled with high amplitude fluorescence FAM and B2 labeled with high amplitude fluorescence HEX (or VIC) in Strain B. The corresponding schematic of the 2-D cluster plot graph, see FIG. 12, shows measurements of parentals and recombinants. Amplified markers are viewed in a 2-D plot in which Ch1 amplitude fluorescence is plotted versus Ch2 amplitude fluorescence for each droplet. The droplets are clustered into nine major groups of interest: negatives, no markers present; A1−A2 (Parental A); B1−B2 (Parental B); A1−B2 (Recombinant); B1−A2 (Recombinant); A1 (frag); B1 (frag); A2 (frag); B2 (frag).

FIG. 7 shows one application of a multiplex experiment for a recombination assay using ddPCR with two fluorophores and amplitude intensity modulation to score three (3) markers in a single well. The graph shows measurements of the numbers of droplets that are positive and negative for each fluorophore: A triplex with two FAM and a VIC: SDHA-FAM, B2M-FAM, GAPDH-VIC. Each droplet in a sample is plotted on a graph of amplitude intensity (e.g., FAM or VIC amplitude) on the y-axis versus droplet number (e.g., event number) on the x-axis. All FAM positive droplets above a given threshold intensity (indicated by the bolded line) are scored as positive and assigned a value of FAM amplitude (FIG. 7A). All VIC (or HEX) positive droplets above a given threshold intensity (indicated by the bolded line) are scored as positive and assigned a value of VIC amplitude (FIG. 7B). All negative droplets (those below the threshold). The groups can be distinguished by their color and amplitude intensities based on their fluorophore combination. In some cases, determining threshold intensity may be an iterative process. In some cases, a threshold intensity may be chosen and the total number of droplets above said threshold may be quantified. This step may be followed by increasing the threshold intensity and repeating droplet quantification within the subpopulation. This process may be repeated until the number of droplets quantified does not change substantially between one intensity threshold and the next increase.

In some methods of the application, the extent of recombination may be calculated. In some cases, the extent of recombination may be calculated using combinatorics of random partitioning. In some cases, the extent of recombination may be calculated between two parental strains. In some cases, the extent of recombination may be calculated between three parental strains. In some cases, the extent of recombination may be calculated between more than two parental strains.

In some cases, it may be possible to estimate the extent of recombination using the numbers of partitions (e.g. droplets) within a given cluster. In some cases, it may be possible to estimate the extent of recombination using nine clusters. In some cases, it may be possible to estimate the extent of recombination using less than nine clusters. In some cases, it may be possible to estimate the extent of recombination using more than nine clusters. In some cases, it may be possible to estimate the extent of recombination using 16 clusters. In some cases, it may be possible to estimate the extent of recombination using less than 16 clusters. In some cases, it may be possible to estimate the extent of recombination using more than 16 clusters. In some cases, it may be possible to estimate the extent of recombination using 2, 3, 4, 5, 6, 7, 8, 9, 10, 11, 12, 13, 14, 15, 16, 17, 18, 19, 20, 21, 22, 23, 24, or 25 clusters. In some cases, it may be possible to estimate the extent of recombination using less than 2, 3, 4, 5, 6, 7, 8, 9, 10, 11, 12, 13, 14, 15, 16, 17, 18, 19, 20, 21, 22, 23, 24, 25 clusters or less. In some cases, it may be possible to estimate the extent of recombination using more than 2, 3, 4, 5, 6, 7, 8, 9, 10, 11, 12, 13, 14, 15, 16, 17, 18, 19, 20, 21, 22, 23, 24, 25 clusters or more. In some cases, more clusters to estimate the extent of recombination may provide smaller variance compared with estimates using less clusters.

3. Co-Localization

Sample partitioning and the ability to analyze multiple targets in a compartment allows one to detect when targets are spatially clustered together in the sample. This can be done by assessing whether the number of compartments with a particular combination of markers is in statistical excess compared to what would be expected if the targets were randomly distributed in the compartments. The extent of overabundance of such compartments can be used to estimate the concentration of the combination of markers.

For example, one can measure two targets: A and B using a PCR method (e.g., ddPCR). For example, there would be four types of droplets compartments: droplets negative for both targets, droplets positive for A, droplets positive for B and droplets positive for both. Under random distribution the number of double positive droplets should be close to (total number of droplets)*(fraction of droplets with at least B)*(fraction of droplets with at least A). If the number of double positive droplets significantly exceeds the expectation, an inference can be made that the two targets are in proximity to each other in the sample. This result can mean that target A and B are physically linked by virtue of, e.g., being on the same polynucleotide, being on the same viral particle, that they are part of the same protein/nucleic acid complex, that they are part of the same exosome, or that they are part of the same cell.

The presence of a particular target in a partition may be assessed by using a fluorophore specific to that target as part of a probe-based TaqMan assay scheme. For example, when measuring two targets A and B, one can use FAM for A and VIC for B. In some applications, different targets can be assessed with the same fluorophore or intercalating dye using endpoint fluorescence to distinguish partitions containing A from those containing B from those containing A and B. For example, see FIG. 7 illustrating a multiplexing assay with various probe types.

In some applications of the methods, a set of probes, labels, and/or dyes or a combination thereof are used in or after the amplification reaction to generate one or more signals in a compartment that distinguish a parental genome from a recombinant genome. In some applications of the methods, probes, labels and/or dyes or a combination thereof are used in or after the amplification reaction to generate one or more signals in a compartment that determine recombinant rate. In some applications of the methods, probes, labels and/or dyes or a combination thereof are used in or after the amplification reaction to generate one or more signals in a compartment that determine growth rate. Any probes known in the art can be used in the methods provided herein, including but not limited to TaqMan probes, intercalating DNA dyes, Molecular beacons, fluorescent markers, p-Dots, and the like. The methods described herein often involve an amplification step. However, in some cases, the methods do not comprise an amplification step. For example, when a probe is a Molecular Beacon probe, an amplification step may not be necessary.

4. Digital Analysis of ddPCR

A digital PCR device (e.g., droplet digital PCR device) for use with the methods, compositions, and kits described herein can detect multiple signals (see e.g. U.S. Provisional Patent Application No. 61/454,373, filed Mar. 18, 2011, herein incorporated by reference in its entirety).

Droplet digital PCR can involve the generation of thousands of discrete, robust microdroplet reactors per second. ddPCR can involve standard thermal cycling with installed-base instruments, which can make digital data accessible immediately to researchers. Rapid interrogation of each droplet can yield counts of target molecules present in the initial sample A digital readout assay, e.g., digital PCR, can be used to count markers (e.g., target nucleic acid sequences or markers) by partitioning the targets in a sample and identifying compartments containing the target. A digital readout is an all or nothing analysis in that it specifies whether a given compartment contains the target of interest, but does not necessarily indicate how many copies of the target are in the compartment. For example, a single polynucleotide containing two targets can be in a compartment, but under normal analysis conditions, the compartment will only be considered to contain one target. If the targets on the same polynucleotide are separated by a large number of base pairs, some of the target nucleic acid sequences may be separated by fragmentation during purification of a sample some linked target nucleic acid sequences may not remain physically linked after sample preparation. Digital PCR is described generally, e.g., at Vogelstein and Kinzler (1999) *PNAS* 96:9236-9241. Applications of this technology include, but are not limited to, e.g., viral recombination analysis, viral recombination rate determination, viral load analysis, detection of a viral signature in a biological sample, high-resolution genome molecular marker measurements, genome-wide association studies, cytogenetic analysis, alterations in cancerous tissue by a viral infection, and linkage analysis, and other applications as described herein.

In general, dPCR can involve spatially isolating (or partitioning in a compartment) individual polynucleotides or polypeptides from a sample and carrying out a polymerase chain reaction on each compartment. The compartment can be, e.g., a well (e.g., wells of a microwell plate), capillary, dispersed phase of an emulsion, a chamber (e.g., a chamber in an array of miniaturized chambers), a droplet, or a nucleic acid binding surface. The sample can be distributed so that each compartment has about 0, 1, or 2 target polynucleotides or polypeptides. Each compartment can have, on average, less than 5, 4, 3, 2, or 1 copies of a target nucleic acid or polypeptides per compartment (e.g., droplet). In some cases, at least 0, 1, 2, 3, 4, 5, 6, 7, 8, 9, 10, 20, 30, 40, 50, 60, 70, 80, 90, 100, 125, 150, 175, or 200 compartments (e.g., droplets) have zero copies of a target nucleic acid or polypeptides. After PCR amplification, the number of compartments with or without a PCR product can be enumerated. The total number of compartments can be about, or more than about, 500, 1000, 2000, 3000, 4000, 5000, 6000, 7000, 8000, 9000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000, 150,000, 200,000, 500,000, 750,000, or 1,000,000. The total number of compartments can be about 500 to about 1,000, 000, about 500 to about 500,000, about 500 to about 250,000, about 500 to about 100,000, about 1000 to about 1,000,000, about 1000 to about 500,000, about 1000 to about 250,000, about 1000 to about 100,000, about 10,000 to about 1,000,000, about 10,000 to about 100,000, or about 10,000 to about 50,000.

In some applications, the digital PCR is droplet digital PCR. In some applications of a droplet digital PCR experiment, less than about 0.00001, 0.00005, 0.00010, 0.00050, 0.001, 0.005, 0.01, 0.05, 0.1, 0.5, 1, 2, 2.5, 3, 3.5, 4, 4.5, 5, 6, 7, 8, 9, or 10 markers of target polynucleotide or polypeptide can detected. In some cases, less than about 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 150, 200, 250, 300, 350, 400, 450, or 500 markers of a target polynucleotide or polypeptide are detected. In some cases, the droplets described herein are generated at a rate of greater than 1, 2, 3, 4, 5, 10, 50, 100, 200, 300, 400, 500, 600, 700, 800, 900, or 1000 droplets/second.

Methods using ddPCR™ can empower one person to screen many samples, e.g., hundreds of samples, for viral recombination and recombination rate analysis in a single work shift. In one embodiment, a ddPCR™ workflow is provided that involves using one or more restriction enzymes to separate tandem copies of a target nucleic acid sequence prior to assembling a duplex TaqMan® assay that includes reagents to detect both the target nucleic acid sequence (e.g., a first gene) and a single-copy reference nucleic acid sequence (e.g., a second gene).

The present disclosure allows for methods using ddPCR to conduct the recombination assays provide herein and determine information regarding a virus status such as, absolute quantification viral recombination rates, viral load, marker-assisted genotyping of viral particles, molecular signature of a viral particle, virulence, and growth rate. In other aspects the methods using ddPCR recombination assays can be used for generating and propagating new in vitro or in vivo viral strains of medical interest, such as gene or cellular therapy or for scientific investigation tools such as gene-expression systems.

When ddPCR™ is used with the methods, the reaction mixture can then be partitioned into about, less than about, or more than about, 500, 1000, 2000, 3000, 4000, 5000, 6000, 7000, 8000, 9000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000, 150,000, 200,000, 500,000, 750,000, 1,000,000, 2,000,000, 3,000,000, 4,000,000, 5,000,000, 6,000,000, 7,000,000, 8,000,000, 9,000,000, or 10,000,000 nanoliter droplets that can be thermo-cycled to end-point before being analyzed. In some cases, the droplets are greater than one nanoliter; in other cases, the droplets are less than one nanoliter (e.g., picoliter). The number of droplets per reaction can be about 1000 to about 1,000,000, about 1000 to about 750,000, about 1000 to about 500,000, about 1000 to about 250,000, about 1000 to about 100,000, about 1000 to about 50,000, about 1000 to about 30,000, about 1000 to about 10,000, about 10,000 to about 1,000,000, about 10,000 to about 750,000, about 10,000 to about 500,000, about 10,000 to about 250,000, about 10,000 to about 100,000, about 10,000 to about 50,000, or about 10,000 to about 30,000. The number of droplets per reaction can be about 20,000 to about 1,000,000, about 20,000 to about 750,000, about 20,000 to about 500,000, about 20,000 to about 250,000, about 20,000 to about 200,000, about 20,000 to about 50,000, about 50,000 to about 100,000, about 50,000 to about 200,000; or about 50,000 to about 300,000.

An analysis can occur in a digital detector such as, for example a color reader. The fraction of positive-counted droplets can enable the absolute concentrations for the target or reference nucleic acid sequences (e.g., genes, genetic variations in a gene or nucleic acid segment or target sequence, or polypeptide) to be measured. This information can be used to determine a relative number of genetic variants. For example, at least 20,000 PCR replicates per well can provide the statistical power to resolve higher-order differences in amounts. This low-cost method can reliably generate measurements with 95% confidence intervals that span integer without overlap of adjacent states. This technology is capable of determining the linkage of genetic variants, and it can be used to determine whether the genetic variants are on the same or different strand or chromosomes or to determine how far apart they are in a genome.

The volumes may have any suitable size. In some applications, the volumes may have a diameter or characteristic cross-sectional dimension of about 1 to 10 micrometers, 1 to 100 micrometers or 1 to 1000 micrometers. In some applications, the volumes may have a diameter or characteristic cross-sectional dimension of about 10 to 100 micrometers, 10 to 1000 or 10 to 10,000 micrometers.

The nucleic acid that is partitioned may have any suitable characteristics. The nucleic acid may include genetic material of the subject (e.g., the subject's genomic DNA and/or RNA), messenger RNA of the subject, and/or cDNA derived from RNA of the subject, among others provided herein. The nucleic acid may have any suitable average length. Generally, the average length is substantially greater than the distance on a chromosome between the polymorphic loci (e.g., genetic variation) to be analyzed. With this average length, molecular marker in the polynucleotide being investigated are linked frequently in the isolated nucleic acid and thus tend to distribute together to the same volumes when the aqueous phase is partitioned. In some applications, each primer set may be capable of amplifying at least a pair of distinct molecular marker from a genome segment, target sequence, haplotype or locus. In some applications, each primer set may be a capable of amplifying at least a pair of distinct molecular marker from a polypeptide or peptide target sequence or known area harboring a genetic variation of a polypeptide.

Each volume may be partitioned to contain any suitable average concentration of nucleic acid. Generally, the process of partitioning, in combination with a suitable starting concentration of the nucleic acid in the aqueous phase, produces volumes that have an average of less than about several genome equivalents of the nucleic acid per volume. Although the method may be performed with an average of more than one genome equivalent per volume (e.g., about two genome equivalents per volume), the analysis generally becomes more efficient and reliable, with less background, by limiting the concentration to an average of less than about one genome equivalent per volume. Accordingly, each volume may contain on average less than about one copy or molecule of a target region that includes each polymorphic locus and/or an average of less than about one copy of any allele sequence of each polymorphic locus (e.g., genetic variation).

5. Proximity Ligation Assay

Figure 13:
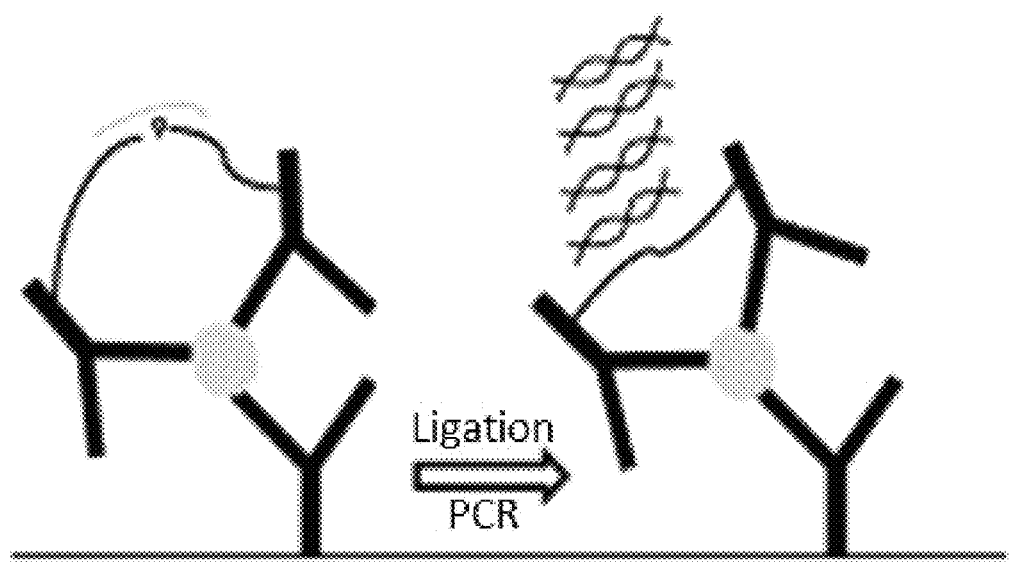
FIG. 13 is a diagram depicting a proximity ligation assay (PLA) which can be used with the methods, systems and various embodiments provided herein.
Figure 14:
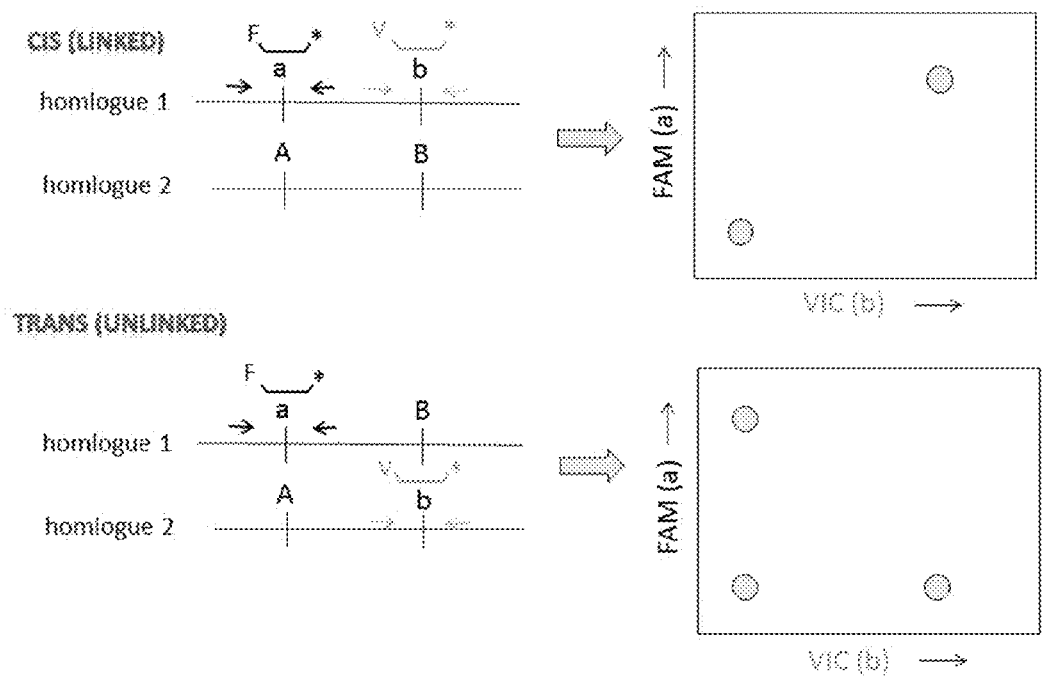
FIG. 14 illustrates complex populations of droplet-clusters arising with cis (linked) and trans (unlinked or recombinant) viral alleles.

The present methods, compositions and kits can be used in conjunction with protein and macromolecule detection assays such as, for example, a proximity ligation assay (PLA) see FIG. 13. The proximity ligation assay can detect the presence of proteins, protein interactions or protein modifications. In some cases, a PLA assay is conducted using two or more PLA antibodies capable of recognizing two different target antigens. In some cases, the PLA antibodies are conjugated to oligonucleotides. The oligonucleotide of one PLA antibody may be ligated to the oligonucleotide of another PLA antibody when their targets are in close proximity. An amplification reaction may then be conducted to detect the ligated product. In some cases a third oligonucleotide capable of "bridging" the two molecules is used to detect the ligated product. In some cases, the oligonucleotides may be designed to interact in other ways; for example, they may hybridize such that one of the oligonucleotides can act to prime an amplification reaction using the other oligonucleotide as the template (see, e.g., discussion herein regarding the PEA assay). In still other examples, a third "bridge" oligonucleotides is introduced, which is capable of recognizing both oligonucleotides. In some cases, the PLA assay may not comprise a third bridge oligonucleotide.

The PLA assay may be particularly useful in recombinant viral particle assays. For example, a recombinant viral particle may have proteins with domains that are derived from two or more different viral genus, strain or species. In some cases, the recombinant particle may have two different proteins, wherein each protein is derived from a different viral genus, species, or strain. The PLA assay may determine whether the two different domains are present within the same viral particle.

In some cases, a PEA (Proximity Extension Assay) may be conducted. In these cases at least two probes (e.g., antibodies conjugated to oligonucleotides) bind to individual targets (e.g., loci) wherein the individual targets are sufficiently close in distance or wherein the probes are sufficiently long or both, such that an overlap of the two antibody-linked oligonucleotides may occur. In such cases, one of the oligonucleotides may be able to act as a primer, hybridizing to the other oligonucleotide and using it as a template for a primer extension reaction or other amplification reaction. In some cases, the PEA assay may not comprise sufficient overlap of the two antibody-linked oligonucleotides. In these cases, a third oligonucleotide may be provided that has a region of homology with each proximity probe and which may act as a molecule bridge between the two probed targets. In some cases, the PEA assay may comprise a third bridge oligonucleotide. In some cases, the PEA assay may comprise multiple bridge oligonucleotides. In some cases, the PEA assay may not comprise a third bridge oligonucleotide.

In some cases, the PLA antibodies may each be attached to a PLA oligonucleotide with a different sequence. A ligation reaction can be performed in order to ligate together the two or more different PLA oligonucleotides when they are in close proximity (see FIG. 13). The ligated PLA oligonucleotides can then be detected using a probe that recognizes both sequences of the PLA oligonucleotides. In some cases, the probe is a molecular inversion probe that is capable of circularizing after ligation. The circularized molecular inversion probe may be detected by any method known in the art. In some cases, the molecular inversion probe is amplified by, e.g., PCR, real-time PCR, or rolling-circle PCR. In some cases, the probe is two or more linear ligation probes, each recognizing a different PLA oligonucleotide. After hybridization, the linear probes may be amplified by any method known in the art.

In some cases, two or more sets of antibodies may be used. In some cases, the viral particle is contacted with a set of primary antibodies, wherein a subset of the antibodies are derived from one species (e.g., mouse, rabbit) and recognize one target polypeptide sequence and a subset of antibodies are derived from a different species and recognize a second target polypeptide sequence. Species-specific secondary antibodies may then bind to the primary antibodies, wherein each of the species-specific secondary antibodies is attached to a unique oligonucleotide sequence. Oligonucleotides with different sequences and that are in close proximity can then be detected using a method described herein or otherwise known in the art.

The disclosure provides for the detection of a viruses presence of proteins, protein interactions or protein modifications using the steps, methods, kits, systems and compositions provided herein with conjunction with the proximity ligation assay. The disclosure also provides for the detection of a viruses nucleotide and proteins using the steps, methods, kits, systems and compositions provided herein with conjunction with the proximity ligation assay.

Accuracy and Sensitivity

The methods and compositions provided herein can quantify polynucleotides (e.g., viral RNA or DNA polynucleotides) in a sample with a high degree of accuracy. Current methods involving gel electrophoresis and sequencing are either imprecise or time-consuming. These methods are prone to in vitro recombination artifacts occurring during unpartitioned reverse transcription (of RNA viruses) and PCR amplification result in artifactually high numbers of recombinants are measured (Negroni et al., 1995; Diaz & DeStefano, 1996; Frohman & Martin. The methods and systems provided herein are generally used for ddPCR applications. However, in some cases, in order to minimize recombination during an assay, a sample (e.g., virus sample or bacterial sample, or other microbe) may be partitioned into aqueous droplets within a water-in-oil emulsion such that no more than one microbe, no more than two microbes, no more than three microbes, no more than four microbes, or no more than five microbes are within a single droplet. The droplets (or other type of partition, e.g., well) may be subjected to an amplification reaction with reduced levels of artifactual recombination. The droplets or partitions may then be pooled and analyzed by any other methods such as by sequencing (e.g., NextGen sequencing).

In some cases, the methods and compositions provided herein can quantify the amount of polynucleotides (e.g., viral RNA or DNA polynucleotides, recombined polynucleotides, etc.) in a sample with an accuracy of greater than 1%, 10%, 20%, 30%, 40%, 50%, 55%, 60%, 65%, 70%, 75%, 80%, 85%, 90%, 95%, 96%, 97%, 98%, 99%, 99.2%, 99.5%, 99.7%, or 99.9%. In some cases, the methods and compositions provided herein can quantify the amount of polynucleotides (e.g., viral RNA or DNA polynucleotides in a sample, recombined nucleic acids in a sample, etc.) with a sensitivity of greater than 1%, 10%, 20%, 30%, 40%, 50%, 55%, 60%, 65%, 70%, 75%, 80%, 85%, 90%, 95%, 96%, 97%, 98%, 99%, 99.2%, 99.5%, 99.7%, or 99.9%. The methods and compositions provided herein may quantify the amount of polypeptides (e.g., viral polypeptide) in a sample with an accuracy of greater than 1%, 10%, 20%, 30%, 40%, 50%, 55%, 60%, 65%, 70%, 75%, 80%, 85%, 90%, 95%, 96%, 97%, 98%, 99%, 99.2%, 99.5%, 99.7%, or 99.9%. The methods and compositions provided herein can quantify the amount of polypeptides (e.g., viral polypeptide) in a sample with a sensitivity of greater than 1%, 10%, 20%, 30%, 40%, 50%, 55%, 60%, 65%, 70%, 75%, 80%, 85%, 90%, 95%, 96%, 97%, 98%, 99%, 99.2%, 99.5%, 99.7%, or 99.9%. The methods and compositions provided herein can quantify the amount of macromolecules (e.g., viral macromolecules) in a sample with superior confidence intervals. The methods and compositions provided herein can quantify the amount of polynucleotides and polypeptides (e.g., viral particles) in a sample with a confidence interval of greater than 1, 10%, 20%, 30%, 40%, 50%, 55%, 60%, 65%, 70%, 75%, 80%, 85%, 90%, 95%, 96%, 97%, 98%, 99%, 99.2%, 99.5%, 99.7%, or 99.9%.

In some applications, the methods and compositions provided herein can quantify polynucleotides originating from virus within a biological sample (e.g., a viral infected cell) with the sensitivity that is at least 1%, 10%, 20%, 30%, 40%, 50%, 55%, 60%, 65%, 70%, 75%, 80%, 85%, 90%, 95%, 96%, 97%, 98%, 99%, 99.2%, 99.5%, 99.7%, or 99.9% of the sensitivity of the same assay for determining the viral polynucleotide recombination rate in a sample such as, blood or tissue, wherein the origin of the viral polynucleotide is from one or more different viral strains, genera, species or subtypes.

The present disclosure provides means for rapid, efficient and sensitive detection of cellular processes such as recombination or growth rate. In some applications, less than about 0.00001, 0.00005, 0.00010, 0.00050, 0.001, 0.005, 0.01, 0.05, 0.1, 0.5, 1, 2, 2.5, 3, 3.5, 4, 4.5, 5, 6, 7, 8, 9, or 10 copies of target polynucleotide or genetic variations are detected to determine recombination or growth rate. In some applications, less than 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 150, 200, 250, 300, 350, 400, 450, or 500 copies of a target polynucleotide genetic variations are detected to determine virulence. In some applications, less than about 0.00001, 0.00005, 0.00010, 0.00050, 0.001, 0.005, 0.01, 0.05, 0.1, 0.5, 1, 2, 2.5, 3, 3.5, 4, 4.5, 5, 6, 7, 8, 9, or 10 copies of target polynucleotide/compartment, copies of target polypeptide/compartment, copies of genetic variations/compartment, or genome copies/compartment are detected to determine recombination rate, growth rate, or some other parameter. In some applications, less than 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 150, 200, 250, 300, 350, 400, 450, or 500 copies of a target polynucleotide/compartment, a target polypeptide/compartment, copies of genetic variations/compartment or genome copies/compartment are detected to determine virulence.

In some applications, less than 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 150, 200, 250, 300, 350, 400, 450, or 500 copies of a target polynucleotide genetic variations or polypeptides are detected to determine a viral signature. In some applications, less than 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 150, 200, 250, 300, 350, 400, 450, or 500 copies of a target polynucleotide genetic variations or polypeptides are detected to determine a viral signature.

In some applications, less than 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 150, 200, 250, 300, 350, 400, 450, or 500 copies of a target polynucleotide genetic variations or polypeptides are detected to determine viral load in a sample. In some applications, less than 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 150, 200, 250, 300, 350, 400, 450, or 500 copies of a target polynucleotide genetic variations or polypeptides are detected to determine a virus's taxonomy or genotype. In some applications, less than 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 150, 200, 250, 300, 350, 400, 450, or 500 copies of a target polynucleotide genetic variations or polypeptides are detected to determine virus's extent of genetic drift.

In some cases, the methods and compositions provided herein comprise detecting recombined nucleic acids in a sample wherein less than 20%, 15%, 10%, 9%, 8%, 7%, 6%, 5%, 4%, 3%, 2%, 1%, 0.1%, 0.05%, 0.01%, 0.005%, 0.001%, 0.0005%, 0.0001%, 0.00005%, 0.00001% of the total nucleic acids in the sample are recombined nucleic acids. In some cases, the methods and compositions provided herein comprise detecting recombined polypeptides in a sample wherein less than 20%, 15%, 10%, 9%, 8%, 7%, 6%, 5%, 4%, 3%, 2%, 1%, 0.1%, 0.05%, 0.01%, 0.005%, 0.001%, 0.0005%, 0.0001%, 0.00005%, 0.00001% of the total polypeptides in the sample are the recombined polypeptides. In some cases, the methods and compositions provided herein comprise detecting recombined nucleic acids in a sample wherein less than 20%, 15%, 10%, 9%, 8%, 7%, 6%, 5%, 4%, 3%, 2%, 1%, 0.1%, 0.05%, 0.01%, 0.005%, 0.001%, 0.0005%, 0.0001%, 0.00005%, 0.00001% of the total nucleic acids that contain a particular locus or loci in the sample are recombined nucleic acids. In some cases, the methods and compositions provided herein comprise detecting recombined polypeptides in a sample wherein less than 20%, 15%, 10%, 9%, 8%, 7%, 6%, 5%, 4%, 3%, 2%, 1%, 0.1%, 0.05%, 0.01%, 0.005%, 0.001%, 0.0005%, 0.0001%, 0.00005%, 0.00001% of the total polypeptides that contain a particular amino acid sequence or sequences in the sample are the recombined polypeptides.

In some cases, a recombined nucleic acid contains a first locus and genetic variation of a second locus. The methods and compositions provided herein are capable of detecting such recombined nucleic acids in a sample wherein less than 20%, 15%, 10%, 9%, 8%, 7%, 6%, 5%, 4%, 3%, 2%, 1%, 0.1%, 0.05%, 0.01%, 0.005%, 0.001%, 0.0005%, 0.0001%, 0.00005%, or 0.00001% of the nucleic acids comprising the first locus are the recombined nucleic acids. In some cases, a recombined polypeptide contains a first locus and genetic variation of the second locus. The methods and compositions provided herein are capable of detecting such recombined polypeptides in a sample wherein less than 20%, 15%, 10%, 9%, 8%, 7%, 6%, 5%, 4%, 3%, 2%, 1%, 0.1%, 0.05%, 0.01%, 0.005%, 0.001%, 0.0005%, 0.0001%, 0.00005%, or 0.00001% of the polypeptides comprising the first locus are the recombined nucleic acids.

III. Systems for Recombination Assay

The present disclosure provides a system for recombination analysis comprising: (a) a droplet generator configured to form droplets of an aqueous phase including nucleic acids or proteins, or viral particles, etc.; (b) a detector configured to collect genetic variation-specific amplification data for each of the markers from individual droplets; and (c) a processor configured to correlate genetic variation-specific amplification data for the first locus with genetic variation—specific amplification data for the second locus from the same volumes and to describe or select a particular signature (e.g., identify the parental genome, the recombinant genome or both) of the nucleic acid for the first and second loci based on correlation of the genetic variation-specific amplification data.

Figure 4:
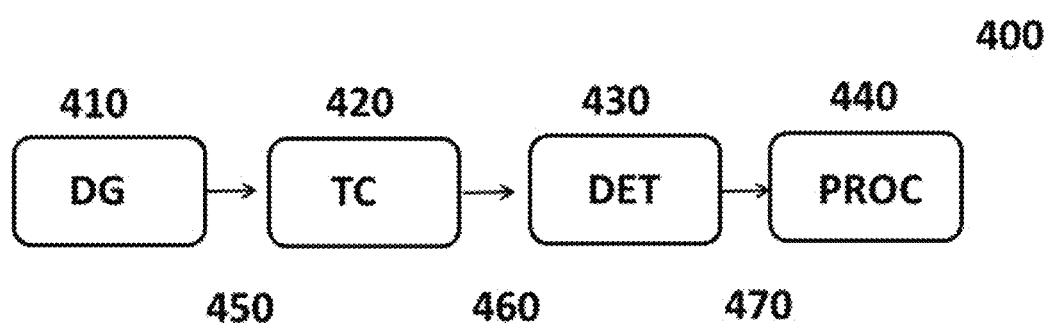
FIG. 4 provides an overview of selected aspects of the systems, devices, and methods provided herein.

FIG. 4 shows a schematic view of selected aspects of the systems provided herein 400 for performing methods. The system may include a droplet generator (DG) 410, a thermocycler (TC) 420, a detector (DET) 430, and a processor (PROC) 440. Arrows 450-470 extend between system components to indicate movement of droplets (450 and 460) and data (470), respectively.

A droplet generator 410 can form droplets such as aqueous droplets in a water-in-oil emulsion such that the droplets contain nucleic acids, or proteins, or viral particles, etc. The droplets may be formed serially or in parallel. In some cases, the droplets comprise additional elements as well such as reagents, primers and/or probes, reagents necessary for an amplification reaction (e.g., PCR, RT-PCR, reverse-transcription PCR, etc.).

A thermocycler 420 can expose the droplets to multiple cycles of heating and cooling to drive amplification, such as PCR amplification, of allele sequences. The thermocycler may be a batch thermocycler, which amplifies all of the droplets in parallel, or may be a flow-based thermocycler, which amplifies droplets serially, among others.

A detector 430 collects amplification data, such as allele-specific or genetic variation—specific amplification data from the droplets. The detector may, for example, be a fluorescence detector, and may detect droplets serially or in parallel.

A processor 440, which also may be termed a controller, can be in communication with detector 430 and can be programmed to process amplification data from the detector. The processor, which may be a digital processor, may be programmed to process raw data from the detector, such as to subtract background and/or normalize droplet data based on droplet size. The processor also or alternatively may be programmed to apply a threshold to convert the data to binary form, to perform a correlation of amplification data, to calculate and/or compare one or more measures of co-amplification, to select a recombinant based on the correlation and/or measures, recombination rate or any combination thereof.

Figure 5:
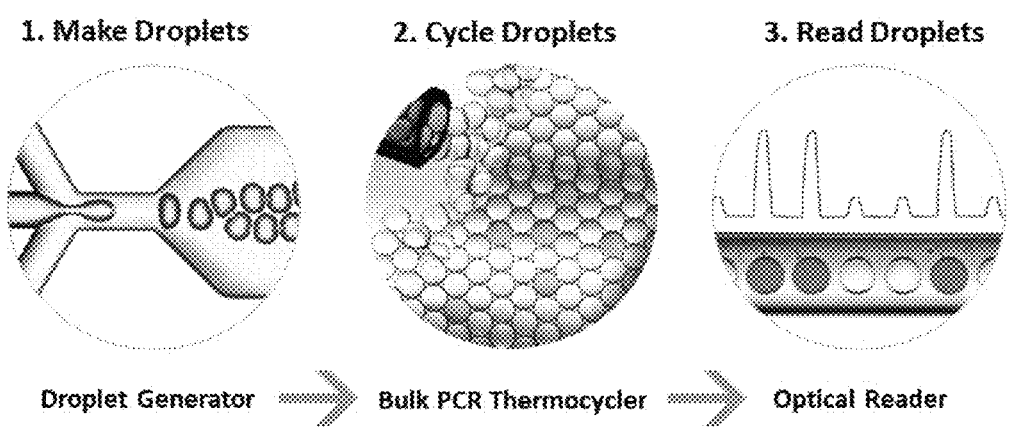
FIG. 5 provides an overview of selected aspects of the systems, devices, and methods provided herein.

FIG. 5 shows a schematic view of selected aspects of the devices and systems to carry out an exemplary method using ddPCR for detecting viral recombinants and determining viral recombination rates or other viral measurements and a status as provided herein. As shown, the process can start by partitioning a sample into multiple partitions (e.g., droplets) using a droplet generator, followed by thermal cycling the sample in a thermal cycler. The fluorescence of the droplets can then be detected using a reader (e.g., an optical reader).

Further aspects of droplet generators, thermocyclers, detectors, and controllers are described in U.S. Patent Application Publication No. 2010/0173394 A1, published Jul. 8, 2010, which is incorporated herein by reference. In some cases, the Raindrop digital PCR system may be used with the methods of this application.

Often, data obtained from the devices as described herein are analyzed using an algorithm applied by a device such as a computer. In some applications a system can be comprised of the droplet generator, thermocycler, droplet reader, and computer are each a separate device. In other applications a system can be comprised of one device comprise two or more of such devices described herein, in any combination in communication with each other. For example a system can be comprised of, but not limited to, a droplet generator in communication with a thermocycler. In another example a system can be comprise a droplet generator, thermocycler, and droplet reader in communication with each other.

Computer and Software

Provided herein are computer processor and computer readable medium comprising instructions which, when executed by a computer, cause the computer to perform methods described herein.

Following acquisition of fluorescence detection data, a processor can be used in some applications to store or process the data. Non-limiting examples of computer-executable logic for or processing data can be used to perform such functions as subtraction of background fluorescence, assignment of target and/or reference sequences, determination of viral recombination rates, identification of a viral recombinant, and quantification of the nucleic or protein data. For example, the number of droplets containing fluorescence corresponding to the presence of a marker in the sample can be counted and compared to the number of droplets containing fluorescence corresponding to the presence of genetic element common to parental viral particles.

A computer can be used for displaying, storing, retrieving, or calculating diagnostic results from the molecular profiling (e.g. viral signature comprised of markers); displaying, storing, retrieving, or calculating raw data from genomic, nucleic acid expression analysis, protein analysis; or displaying, storing, retrieving, or calculating any sample or patient information useful in the methods of the present disclosure.

Provided herein are also systems for conducting the methods provided here in comprising a processor and computer readable medium for instructing the processor for performing methods with one or more devices described herein.

IV. Applications of Methods

The methods, compositions, and systems of the disclosure can be used in a variety of both clinical and research-related applications.

Additional applications of the present disclosure provide a method for determining the taxonomy of a viral particle such as for example a molecular description of its genome and protein capsid. In this embodiment, the methods provided herein are used in combination with an assay such as a proximity ligation assay (PLA assay) or the proximity extension assay (PEA assay) to determine a viral particle's capsid and/or envelope composition, or the composition of other viral polypeptides.

Additional applications of the present disclosure provide a method to quantify a viral particle's degree of virulence. Virus virulence factors determine whether infection occurs and how severe the resulting viral disease symptoms are. Viruses often require receptor proteins on host cells to which they specifically bind. Typically, these host cell proteins are endocytosed and the bound virus then enters the host cell.

Additional applications of the present disclosure provide a method for quantification of viral replication rates. Viruses make new viruses by infecting host cells. The new viruses are assembled in the host cell from component parts into mature or nearly mature virion particles. During typical virus replication and maturation, a single infected cell can make many hundreds or even thousands of new virions.

Additional applications of the present disclosure provide a method for determination and quantification of a viral particle's capability of infection in various types of a host cell. The range of host cells that a virus can infect is called its "host range". This can be narrow or, as when a virus is capable of infecting many species, broad, capable of infecting many different types of host cells (e.g. animal, plant, microbe, or protozoa, etc.). For example, the production of antigenic shifts in Influenza A virus can result from pigs being infected with the virus from several different hosts (such as human and bird). This co-infection provides an opportunity for mixing of the viral genes between existing strains, thereby producing a new viral strain.

Additional applications of the present disclosure may provide a method for assessing the extent of reshuffling of segments in synthetic biology applications. Reshuffling segments of a genome is a process utilized in synthetic biology to create new parts and improved functions by repeated cycles of mutagenesis and amplification to select for desired traits. Similar to measuring the number of recombinant molecules in a viral sample, reshuffled segments of a synthetic biology sample may also be quantified. In some cases, the methods described herein may be used as a quality control measure of a synthetic process to confirm the amount of segments that have been reshuffled in a sample. Similarly, the methods described herein may be used to evaluate or measure recombination in plasmids, F' factors, and other synthetic templates.

Additional applications of the present disclosure include measuring somatic recombination, such as an immune repertoire. The methods may comprise measuring the rate of recombination of the Variable (V), Diverse (D), and Joining (J) regions in T cell receptor domains or B cell receptors or antibodies. V(D)J rearrangements as well as VJ rearrangements may be evaluated. The rate of recombination within immune cells may be particularly informative for diagnosing, treating, prognosing, or detecting autoimmune diseases or disorders or infectious diseases. The methods provided herein are also applicable to measuring variations or recombination in HLA sequences.

The methods provided herein, particularly as they relate to the PEA and PLA assays, may enable assessing how different factors modulate the composition of a multi-component complex or macromolecular complex (e.g., ribosomes, spliceosomes, proteosomes, photosynthetic reaction centers, mitochondria, etc.). The factors may be a mutation (e.g., a mutation that alters the stability of that allele's protein product and therefore resulted in little contribution of that encoded subunit into a multimeric complex), a drug, or other factor. The advantage of using PLA or PEA in the described methods is that they may be used to interrogate mutations or drugs with functional consequences such as disrupting a protein-protein interaction.

Interrogations using the PLA and PEA assays described herein may be useful in drug screening assays. In such cases, a test agent may be applied to a known macromolecular complex. The complex may then be interrogated by the PLA or PEA methods provided herein in order to determine whether the test agent caused a disruption or change in the structure of the macromolecular complex. Similarly, a test agent may be applied to free components capable of assembling into a macromolecular complex (e.g., free capsid proteins). The PLA and PEA methods provided herein may be used to determine whether a test agent caused assembly of the components (e.g., assembly into a viral particle, in the case of capsids).

Interrogations using the PLA and PEA assays described herein may also be used in a clinical setting, e.g., in order to determine the effect of a drug on the structure of a macromolecular complex within a patient. For example, a subject with Duchenne Muscular Dystrophe may be treated with a particular drug such as an anti-sense exon-skipping drug capable of altering the fraction of "improved" (not quite wt) dystrophin protein: mutant dystrophin protein in muscle tissue. In order to determine if the drug is working, a muscle sample may be taken from the patient and relative quantity of improved mutant dystrophin may be determined. Alternatively, the assay may be used to determine the effectiveness of a drug designed to silence a dominant allele's product that was poisoning the structure of function of a macromolecular complex. The methods may also be used to evaluate the genetic composition of a product of fertilization. For example, the methods may be used to determine if each variant allele present in two genomes (encoding products of different macromolecular complexes) contribute equally or unequally to the composition of a macromolecular complex.

The present disclosure is particularly useful for detecting recombination within influenza viruses. The influenza A capsid contains the antigenic glycoproteins hemagglutinin (HA) and neuraminidase (NA). HA plays a role in viral attachment and NA is involved in viral release. The capsid is made up of several hundred molecules of each polypeptide. Often, a host's immune system recognizes HA and NA, thus eliciting an immune response. Many different subtypes of the influenza A HA and NA proteins exist; and the human immune system is frequently challenged with new antigens. For example, point mutations in the HA and NA genes can lead to changes in antigenicity that allow a virus to infect people who were either infected or vaccinated with a previously circulating virus. The influenza genome also encodes additional structural proteins necessary to form the capsid, the nucleoprotein (NP), and the proteins NS1 (non-structural protein 1) and NS2/nuclear export protein (NEP). Still other proteins encoded by the viral genome include membrane proteins M1 and M2 (which are needed for nuclear export and several other functions).

The current invention provides for methods, compositions and kits for evaluation and quantification of latent viral strains for vaccine production. For example, vaccine strains of viruses can be used to create recombinant viruses that carry extra genes coding for a specific immunogen. During viral vaccination, the replicating virus will express the specific immunogen. Specific antibody production will be stimulated, and the host will be protected from the immunogen as well as from the vaccine virus. Alternatively, two viral strains can be deliberately co-infected to create various novel recombinants. For example, a panel of various recombinant viral particles is screened with various test agents in order to identify a vaccine of interest that stop or reduces the growth rate of the targeted viral particles in a host cell. In such viral studies (a viral polynucleotide (e.g., DNA, RNA, mitochondrial DNA, etc.) is monitored over time in order to determine the growth rate of the virus, virulence, or the rate of infection. In some cases, as described herein, the methods and compositions provided herein may be used to ascertain a recombination frequency. In some cases, the recombination frequency may be affected by the growth rate of the viruses (or other microbes, e.g., bacteria, parasites) in the sample. For example, an increase in the growth rate of recombined viruses may result in an increase in the observed recombination frequency. Such an increase can have a myriad of clinical applications, particularly in cases where the recombined viruses have increased virulence (e.g., more than 1-fold, 2-fold, 3-fold, 5-fold, or 10-fold) the virulence of the parental strain. An increase in such virulent recombinants may provide epidemiological information regarding the spread of virulent viruses and also may be of clinical use and inform treatment (e.g., drug selection, personalized care) of patients. In cases where several co-infecting strains of microbes (e.g., viruses) have infected a host or subject, the recombination frequency may be compounded by the differential growth rate of one or more of the viral species present. For example, if one of the co-infecting species is particularly subject to higher growth rates or recombination, the recombination frequency may reflect that.

This disclosure is particularly useful for measuring recombination frequency between species, such as between a virus and its host, e.g., human host. In such cases, recombination of viral and host (e.g., human) markers may be calculated.

In yet another example, a panel of vaccines can be screened against a specific cell-type (e.g., particular host cell types, plant, animal or microbe, etc.), or a particular cell type such as a cancerous mammalian cell, and then the rate of growth of the cancerous cell can be monitored by detecting cellular polynucleotides over time using the present methods and compositions. In yet another example, a panel of vaccines can be screened against a specific cell-type and then cellular viability can be monitored over time by detecting cellular polynucleotides using the present methods and compositions of the disclosure. In such a manner, vaccines that cause cellular toxicity can be identified. In yet other applications, effects on cell growth are measured while altering vaccine dosages, chemical concentrations and environmental conditions (e.g., host cell types, temperature and atmosphere) over time.

Additional applications of the present disclosure provide a method for generating a molecular signature of a viral particle. The virus signature is a molecular fingerprint in that it can be used to detect and identify specific viruses in a cell, tissue or biological fluid. The molecular signature of a viral particle can be generated from nucleic acid comprising the genome of the viral particle. The molecular signature of a viral particle can be generated from the polypeptides or macromolecules comprising the capsid of the viral particle. The molecular signature of a viral particle can be generated from the polynucleotides or macromolecules comprising the capsid of the viral particle and the nucleic acids comprising the genome of the viral.

Additional applications of the present disclosure provide a method for generating new viral recombinant strains. Naturally occurring recombination occurs between virus genomes in a cell infected by more than one virus strain. This occurs either by homologous crossing over of the nucleic acid strands or by reassortment of genomic segments. New viral recombinants strains can be useful in the generation of novel viral vaccines or gene therapy vectors.

Additional applications of the present disclosure provide a method for detecting, identifying, and quantification of a viral load in a cell, tissue, or biological fluid. Viral load, also known as viral burden or viral titer, is a measure of the severity of a viral infection, and can be calculated by estimating the amount of virus in an involved body fluid. For example, it can be given in RNA or DNA copies per milliliter of blood. Tracking viral load can be used to monitor therapy during chronic viral infections, and in immune-compromised patients such as those recovering from bone marrow or solid organ transplantation.

Additional applications of the present disclosure provide a method for describing the genome re-arrangement or a viral genome in a mammalian cell, tissue, or biological fluid. Virus can undergo re-arrangements in their genome such that they display frameshifting of genome unit. The phenomenon is known to occur widely throughout eukaryotic RNA viruses. As in the example provided by the HIV genome, retroviral genomes exhibit overlapping gene arrangements. The mouse mammary tumor virus (MMTV) genome has been shown to exhibit an overlapping gag, pro, and pol gene arrangement.

Additional applications of the present disclosure may provide a method for determining the prevalence of recombinant forms of HIV in a given population. In some cases, HIV may undergo re-arrangements in its genome, creating virus diversity within a human population. Widespread use of antiretroviral drugs may lead to particular drug-resistant strains of HIV. Thus, it is important to understand the range of circulating genetic variants within a given population. The methods described herein may provide a method to quantify the prevalence of recombinant forms.

The methods and compositions can also be used in or for evaluating the efficacy of a viral therapy vector for gene or cellular therapy. Examples of viral therapy vector for gene or cellular therapy used for the treatment of disease, include such disease as macular degeneration, muscular dystrophy, or other tissue wasting diseases.

The current invention provides for methods, compositions and kits for detection and quantification of viral-based cellular expression systems. Such as for example viral-based cellular expression systems used in surgery for detecting a particular cell type or diseased cell (e.g. tumor cell, or infected cell), or healthy cell (e.g. non-infected cell), viral-based cellular expression systems for laboratory and research used in an experimental organism or animal model.

The current invention provides for methods, compositions and kits for evaluating the efficacy of an anti-viral treatment comprising: in a virus infected cell, tissue or biological fluid. In some applications, clinical samples can be obtained from a patient at different time points, for example before and after the patient is treated with an anti-viral treatment or other drug, and then the concentration of viral polynucleotides can be compared in these samples in order to determine whether the patient is responding to the anti-viral treatment. In some applications, one sample is taken prior to treatment and one sample is taken following treatment of the patient with the anti-viral treatment or other drug. In other applications, one sample is taken prior to treatment and then multiple samples are taken following treatment of the patient with the anti-viral treatment or other drug. The clinical samples can be obtained from normal patients, patients at risk for having a disease or disorder (e.g., infectious disease), patients with a specific disease, patients with an infectious disease, patients with an infectious disease and undergoing drug treatment. The methods and compositions of the disclosure can be used to monitor the course of an infection in a subject who has not been treated with a specific anti-viral treatment, or to monitor the effectiveness of a drug, e.g., an anti-viral treatment, against such infection.

The methods and compositions of the disclosure can also be used to identify viral susceptibility of a given host cell and/or resistance to a specific drug (e.g., anti-viral treatment). Viral particles (e.g., clinical isolates) can be cultured with a host cell and then treated with a specific drug (e.g., anti-viral treatment). Following treatment, the growth rate of the viruses can be monitored in order to determine whether the virus is susceptible or resistant to the specific drug. In some applications, one sample is taken prior to treatment and one sample is taken following treatment of the sample with the anti-viral treatment or other drug. In other applications, one sample is taken prior to treatment and then multiple samples are taken following treatment of the sample with the anti-viral treatment or other drug.

Additional applications of the present disclosure provide a method for evaluation of a viral particle's ability to undergo adaptation. That is, the methods provided for a viral particle to be evaluated for quantifying the likelihood that a virus will be able to successfully emerge in a new species to predict the risk of disease emergence in a new host population.

Additional applications of the present disclosure provide a method for evaluation of in vivo or in vitro systems to quantify virus fitness, transmission fitness and/or epidemiologic fitness of a viral particle.

The subject methods and compositions can also be used to identify the efficacy of viral decontamination efforts, or sterilization efforts. For example, samples, or swabs from a surface before and after decontamination or sterilization are obtained. Such samples or swabs can then be analyzed using the subject methods and compositions to evaluate the presence of viral contamination and the extent to which such contamination is eliminated. The subject methods and compositions can also be used to detect whether viral contamination has occurred, for example an accidental release from an industrial or academic laboratory, or a release resulting from an act of biological terrorism or bio-warfare.

In order to carry out the various applications of the methods provide herein, various conventional techniques can be used in combination to tailor the methods to the particular application. Such conventional techniques can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press); Stryer, L. (1995) Biochemistry (4th Ed.) Freeman, New York; Gait, "Oligonucleotide Synthesis: A Practical Approach" 1984, IRL Press, London, Nelson and Cox (2000), Lehninger, (2004) Principles of Biochemistry $4^{th}$ Ed., W. H. Freeman Pub., New York, N.Y. and Berg et al. (2006) Biochemistry, 6th Ed., W. H. Freeman Pub., New York, N.Y., all of which are herein incorporated in their entirety by reference for all purposes.

IV. Kits

Provided herein are kits for carrying out the methods and application described by the present disclosure. Kits described herein can be provided, marketed and/or promoted to health care providers, including physicians, clinical laboratory scientists, nurses, pharmacists, formulary officials, and the like. Kits can also, be marketed directly to the consumer.

Kits may often comprise insert materials, compositions, reagents, device components, and instructions on how to perform the methods or test on a particular biological sample type. The kit can be packaged in any suitable manner, typically with all elements in a single container along with a sheet of printed instructions for carrying out the method or test. Depending on the method desired a kits can comprise one or more of the following components: reagents, buffers, enzymes (e.g. endonucleases, exonucleases, ligases, polymerases, RNA polymerases, DNA polymerases, reverse transcriptases, topoisomerases, kinases, phosphatases), antibodies, primers, probes, dyes, experimental standards (e.g. described viral particles, cells, nucleic acids, and the like), devices, and computer software (e.g. computer-executable logic that instructs a processor) to drive and instruct the devices, and instructions for the user or technical staff such as, researchers or clinicians for implementing the methods provided herein.

The kits can further comprise reagents to enable the detection of cell markers by downstream methods such as RT-PCR, droplet digital PCR, droplet-based digital PCR, DNA and RNA sequencing, mass spectrometry, immunohistochemistry (IHC), laser cell microdissection (LCM), high content cell screening, flow cytometry, which are suitable for enhancing the information from the methods and devices for further clinical detection, prognosis, drug response determination, and diagnosis of a patient suffering from a disease.

In other applications, a kit can further comprise a software package for data analysis of viral particle profiling, which can include reference viral profiles for comparison. In some applications the kits software package including connection to a central server to conduct for data analysis and where a report with recommendation on disease state, treatment suggestions, or recommendation for treatments or procedures for viral management in a patient can be retrieved by the clinician.

The report provided with the kit can be a paper or electronic report. It can be generated by computer software provided with the kit, or by a computer sever which the user uploads to a website wherein the computer server generates the report.

In some applications, the kits and reports generated by the kit can further comprise information, such as scientific literature references, package insert materials, clinical trial results, or summaries of these and the like, which indicate or establish the activities and/or advantages of the composition, and/or which describe dosing, administration, side effects, drug interactions, or other information useful to a health care provider. Such information can be based on the results of various studies, for example, studies using experimental animals involving in vivo models and studies based on human clinical trials.

The term "about," as used herein and throughout the disclosure, generally refers to a range that may be 15% greater than or 15% less than the stated numerical value within the context of the particular usage. For example, "about 10" would include a range from 8.5 to 11.5.

While preferred applications of the present invention have been shown and described herein, it will be obvious to those skilled in the art that such applications are provided by way of example only. Numerous variations, changes, and substitutions will now occur to those skilled in the art without departing from the invention. It should be understood that various alternatives to the applications of the invention described herein may be employed in practicing the invention. It is intended that the following claims define the scope of the invention and that methods and structures within the scope of these claims and their equivalents be covered thereby.

EXAMPLES

Example 1—Droplet Cluster Identification and Classification

A sample may be obtained by performing a throat swab or nasal swab on a subject suspected of being infected with a particularly virulent recombined strain of influenza virus. Nucleic acids from the sample are extracted, combined with specific probes and/or amplification reagents, and partitioned into aqueous droplets within a water-in-oil emulsion. The virulent strain may be characterized by an A allele at the A/a locus and a B allele at the B/b locus. Probes comprising primers attached to fluorophores are designed to detect the A locus by emitting a signal with a particular color and to detect the B locus by emitting a signal with a different color. Although fluorescence probes are designed to one viral allele, they also fluoresce (at reduced intensity) when they cross-react with the other allele. For example, a FAM-labeled probe is designed to detect the A allele and droplets exhibit four levels of fluorescence: the highest level is for droplets containing only the A allele; a lower level is for droplets containing a mixture of A and a; a substantially lower level is for droplets containing only a; and the lowest level is for droplets containing neither A nor a. Droplets that arise from a single molecular species (e.g. the linked A-B species) are more common than droplets arising from combinations of molecules that happen by chance to appear in the same droplet (e.g. unlinked molecules containing A and B). Mathematical analysis of the droplet population sizes is used to estimate the number of linked molecules of each species and to determine phase as well as recombination frequency. The method further comprises determining the proportion of the viruses in the sample that are recombined viruses indicative of the more virulent strain. Based on these results, a drug therapy regimen is designed depending on which virus is the predominating virus.

Example 2—Determining Recombination Rate in RNA Sample

RNA is taken from a cellular blood sample from an HIV infected patient. The sample is partitioned into aqueous droplets in a water-in-oil emulsion. Allele-specific fluorescence probes (FAM; and HEX) are used to detect viral alleles at two different loci on the HIV virus. Following RT-ddPCR, the droplets are positive for one fluorophore, positive for both fluorophores, or positive for neither fluorophore, depending on the viral alleles they contained at the beginning of the reaction. Trans-configured viral alleles partition independently into droplets. Cis-configured viral alleles tend to co-segregate into the same droplets, because they are physically linked, see FIG. 14. Restriction digest at a site between the cis-configured viral alleles abolishes co-partitioning of the two viral alleles (not shown). This quantitative difference or ratio between trans-configured and cis-configured viral alleles determines the recombinant rate of the HIV sample.

Example 3—Determining Recombination Rate in DNA Sample

DNA is taken from a cellular blood sample from an HIV infected patient. The sample is partitioned into aqueous droplets in an oil-aqueous emulsion. Allele-specific fluorescence probes (FAM; and HEX) are used to detect viral alleles at two different loci on the HIV virus. Following ddPCR, the droplets are positive for one fluorophore, positive for both fluorophores, or positive for neither fluorophore, depending on the viral alleles they contained at the beginning of the reaction. Trans-configured viral alleles partition independently into droplets. Cis-configured viral alleles tend to co-segregate into the same droplets, because they are physically linked, see FIG. 14. Restriction digest at a site between the cis-configured viral alleles abolishes co-partitioning of the two viral alleles. This quantitative difference or ratio between trans-configured and cis-configured viral alleles determines the recombinant rate of the HIV sample.

Example 4—Determining Recombination Rate in Purified Virus Sample

A purified viral sample is taken from an HIV infected patient. The sample is partitioned into aqueous droplets in a water-in-oil emulsion such that at most one viral particle is contained within a droplet. The viral particles undergo a lysis reaction within the droplets and, optional, are subjected to a reverse-transcription reaction within the droplets. Allele-specific fluorescence probes (FAM; and HEX) are used to detect viral alleles at two different loci on the HIV virus. Following RT-ddPCR, the droplets are positive for one fluorophore, positive for both fluorophores, or positive for neither fluorophore, depending on the viral alleles they contained at the beginning of the reaction. Trans-configured viral alleles partition independently into droplets. Cis-configured viral alleles tend to co-segregate into the same droplets, because they are physically linked, see FIG. 14. Restriction digest at a site between the cis-configured viral alleles abolishes co-partitioning of the two viral alleles (not shown). This quantitative difference or ratio between trans-configured and cis-configured viral alleles determines the recombinant rate of the HIV sample.

Example 5—Mathematical Relationships when Two Sequences are not Physically Linked Two markers A and B are not physically on the same chromosome. In this case, partitions have both A and B present by chance co-localization and the independence of molecular partitioning is expressed as:

$$N_A N_B = N_E N_{AB} \qquad \text{Eq. 1}$$

wherein N denotes the number of droplets, wherein $N_A$ and $N_B$ are the counts of single-positive droplets, $N_E$ is the count of negative (empty) droplets, and $N_{AB}$ is the count of double-positive droplets. Some droplets contain multiple copies of the same target. In these cases, the number of droplets observed as double-positives due to chance, $N_{ch}$, is expressed as:

$$N_{ch} = N_A N_B / N_E \qquad \text{Eq. 2}$$

Example 6—Mathematical Relationships when Two Sequences are Linked

Two DNA sequences are physically linked. When A–B molecules are present, extra double-positive droplets are present. Double positive droplets include: A–B, A+A–B, B+A–B, A–B and A+B+A–B. The total number of droplets that do not contain linked molecules is expressed as:

$$N_{not\_\underline{AB}} = N_E + N_A + N_B + N_A N_B / N_E \qquad \text{Eq. 3}$$

The concentration (average copies/droplet) of the molecules contributing to the linked droplets A–B is expressed as:

$$\lambda_{AB} = \ln(N_{tot}) - \ln(N_E + N_A + N_B + N_A N_B / N_E) \qquad \text{Eq. 4}$$

wherein $N_{tot}$ is the total number of observed droplets.

The percentage of linked molecules is expressed as $$\% \underline{AB} = 2\lambda_{\underline{AB}}/(\lambda_A + \lambda_B) \quad \text{Eq. 5}$$

Example 7—Viral Recombination Calculations

Figure 15B:
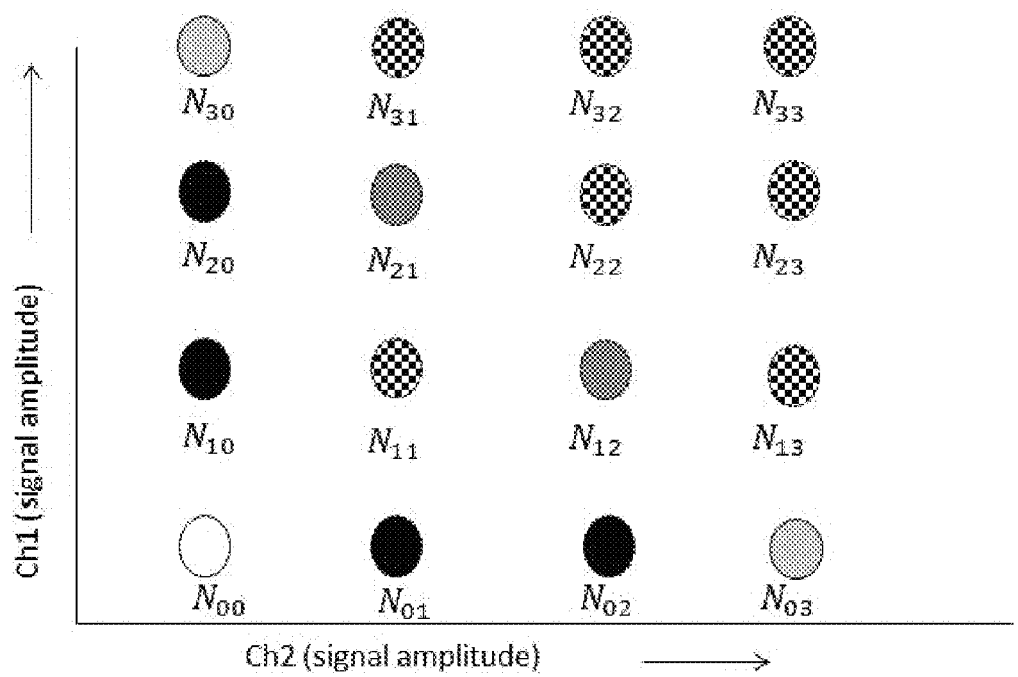

Combinatorics of random partitioning is applied to calculate the concentration of full-length parental molecules, full-length recombinant molecules, or both. In this example, there are a total of eight molecular species that are detected by the assay including 2 parental full length viral alleles, 2 recombinant full length viral alleles and 4 individual marker fragments, assuming some fragmentation occurs, see FIG. 15A. Amplitude-based multiplexing results in 16 possible droplet clusters, see FIG. 15B. Each cluster comprises a number of droplets. The count per cluster is denoted as $N_{xy}$. By combining these numbers, the concentrations of all eight species is calculated. FIG. 15C displays all possible molecular species that are partitioned in any droplet or part of any of the 16 clusters. In each box, a droplet contains any combination of the species shown, but in order for a droplet to land in a given box, for example N_11, a droplet contains at least A1 and B1. If A1, B1, or both are missing, the droplet does not land in N_11. Resulting droplets with all possible molecular species combinations within a single droplet (denoted with parenthesis) that occur in each box are shown in FIG. 15D.

It is possible to calculate viral recombination using all 16 clusters. In this example, only the 9 clusters in the lower left part of the table are used (FIG. 15D, gray colored groups) to calculate viral recombination. In cluster N_21, the possible droplet types are (B1A2), (B1A2, B1), (B1A2, A2) and (B1, A2). To calculate the concentration of recombinant species B1A2, the droplets that do not contain this species need to be excluded. To begin, the poisson formula is applied:

$$\lambda = \ln(N_{tot}) - \ln(N_{negatives}) \quad \text{Eq. 6}$$

The expected number of droplets of kind (B1, A2) is expressed as:

$$N_{B1,A2}^{expected} = N_{01} * \frac{N_{20}}{N_{00}} \quad \text{Eq. 7}$$

Thus the real number of droplets that have B1A2 are expressed as:

$$N_{B1A2}^{linked} = N_{21} - N_{B1A2}^{expected} \quad \text{Eq. 8}$$

Then, the expected copies per droplet of B1A2 species, $\lambda_{B1A2}$, is given by:

$$\lambda_{B1A2} = \ln(N_{tot}) - \ln\left(N_{00} + N_{20} + N_{01} + \frac{N_{01} * N_{20}}{N_{00}}\right) \quad \text{Eq. 9}$$

$$N_{tot} = N_{00} + N_{20} + N_{01} + N_{21} \quad \text{Eq. 10}$$

Similarly for the other recombinant:

$$\lambda_{A1B2} = \ln(N_{tot}) - \ln\left(N_{00} + N_{02} + N_{10} + \frac{N_{02} * N_{10}}{N_{00}}\right) \quad \text{Eq. 11}$$

$$N_{tot} = N_{00} + N_{02} + N_{10} + N_{12} \quad \text{Eq. 12}$$

The expected copies per droplet for the parent species A1A2 and B1B2 is given by $$\lambda_{A1A2} = \ln(N_{tot}) - \ln\left(N_{00} + N_{10} + N_{20} + \frac{N_{10} * N_{20}}{N_{00}}\right) \quad \text{Eq. 13}$$

$$N_{tot} = N_{00} + N_{10} + N_{20} + N_{30} \quad \text{Eq. 14}$$

$$\lambda_{B1B2} = \ln(N_{tot}) - \ln\left(N_{00} + N_{01} + N_{02} + \frac{N_{01} * N_{02}}{N_{00}}\right) \quad \text{Eq. 15}$$

$$N_{tot} = N_{00} + N_{01} + N_{02} + N_{03} \quad \text{Eq. 16}$$

What is claimed is:

1. A method of quantifying previously recombined nucleic acids containing a first sequence and a second sequence, the method comprising:
    a. obtaining a sample comprising viral genomic nucleic acids, wherein the viral genomic nucleic acids comprise (i) first parental nucleic acids representing a first viral genome that includes the first sequence and not the second sequence, (ii) second parental nucleic acids representing a second viral genome that includes the second sequence and not the first sequence, and (iii) a plurality of previously recombined nucleic acids including, on a same strand, the first sequence and the second sequence;
    b. partitioning the sample into more than about 1,000 compartments such that each compartment of only a subset of the more than about 1,000 compartments contains the first sequence, each compartment of only a subset of the more than about 1,000 compartments contains the second sequence, and each compartment of only a subset of the more than about 1,000 compartments contains both the first sequence and the second sequence;
    c. performing amplification of the first sequence and amplification of the second sequence within the more than about 1,000 compartments;
    d. detecting at least one amplification signal from the more than about 1,000 compartments indicating whether the first sequence is present in a given compartment and whether the second sequence is present in the given compartment;
    e. enumerating compartments of the more than about 1,000 compartments that comprise the first sequence but not the second sequence to obtain a first value, the second sequence but not the first sequence to obtain a second value, both the first sequence and the second sequence to obtain a third value, and neither the first sequence nor the second sequence to obtain a fourth value, wherein the step of enumerating is performed using the at least one amplification signal detected from the more than about 1,000 compartments;
    f. calculating an expected number of compartments of the more than about 1,000 compartments comprising both the first sequence and the second sequence by chance co-localization, using the first, second, and fourth values; and
    g. adjusting the third value of step (e) using the expected number of step (f) in order to obtain a numerical value for the recombined nucleic acids.

2. The method of claim 1, wherein the first parental nucleic acids comprise a genetic variant of the second sequence, and wherein the at least one amplification signal also indicates whether the genetic variant of the second sequence is present in a given compartment.

3. The method of claim 2, wherein the second sequence and the genetic variant of the second sequence differ from one another by a genetic variation, and wherein the genetic variation is selected from the group consisting of single nucleotide polymorphisms, insertions, inversions, rearrangements, transversions, deletions, indels, microsatellite repeats, minisatellite repeats, short tandem repeats, transposable elements, large scale structural variants, and combinations thereof.

4. The method of claim 2, wherein each of the more than about 1,000 compartments comprises a probe including a polynucleotide attached to a fluorophore, wherein the polynucleotide of the probe is capable of hybridizing to the second sequence, and wherein the polynucleotide of the probe is capable of hybridizing to the genetic variant of the second sequence.

5. The method of claim 2, wherein the step of enumerating compartments includes a step of enumerating compartments that comprise both the first sequence and the genetic variant of the second sequence.

6. The method of claim 2, wherein the second parental nucleic acids include a genetic variant of the first sequence, and wherein the at least one amplification signal also indicates whether the genetic variant of the first sequence is present in a given compartment.

7. The method of claim 6, wherein the step of enumerating compartments includes a step of enumerating compartments of the more than about 1,000 compartments that comprise both the second sequence and the genetic variant of the first sequence, and a step of enumerating compartments of the more than about 1,000 compartments that comprise both the first sequence and the genetic variant of the second sequence.

8. The method of claim 2, wherein amplification of the second sequence and amplification of the variant of the second sequence are detected via probes that emit light of a same color as one another.

9. The method of claim 1, wherein the viral genomic nucleic acids comprise RNA.

10. The method of claim 1, wherein the first viral genome is selected from the group consisting of Adenovirus, Coxsackievirus, Epstein-Barr virus, Hepatitis A virus, Hepatitis B virus, Hepatitis C virus, Herpes simplex virus, type 2, Cytomegalovirus, Human herpesvirus, type 8, Human immunodeficiency virus, Influenza virus, Measles virus, Mumps virus, Human papillomavirus, Parainfluenza virus, Poliovirus, Rabies virus, Respiratory syncytial virus, Varicella-zoster virus, and a variant strain thereof.

11. The method of claim 1, wherein the first viral genome is from an influenza strain, and wherein the second viral genome is from an influenza strain.

12. The method of claim 11, wherein the influenza strain of the first viral genome is H1N1, H5N1, H3N2, H7N9, or H1N2, or a recombinant strain thereof, and wherein the influenza strain of the second viral genome is H1N1, H5N1, H3N2, H7N9, or H1N2, or a recombinant strain thereof.

13. The method of claim 1, wherein the first and second viral genomes are Human immunodeficiency virus genomes.

14. The method of claim 1, wherein the sample is combined with a label prior to step (c).

15. The method of claim 14, wherein amplification of the first sequence and amplification of the second sequence are detected via labels that emit light of different color from one another.

16. The method of claim 1, wherein a distance between the first and second sequences in the previously recombined nucleic acids is less than about 20 kilobases.

17. The method of claim 1, wherein the sample is partitioned into more than about 10,000,000 compartments.

18. The method of claim 1, wherein the more than about 1,000 compartments include a first probe that binds to the first sequence and a second probe that binds to the second sequence.

19. The method of claim 1, wherein the first and second parental nucleic acids represent at least 80% of viral genomic nucleic acids in the sample that contain the first sequence and/or the second sequence.

20. The method of claim 1, wherein the first parental nucleic acids and the second parental nucleic acids are provided by different strains of a same species of virus.

21. The method of claim 1, wherein the first parental nucleic acids and the second parental nucleic acids are provided by different virus species.

22. The method of claim 1, wherein amplification of the first sequence and amplification of the second sequence are detected via probes that emit light of a same color as one another.

23. The method of claim 1, wherein the step of calculating includes a step of calculating the expected number of compartments using the following:

$$\text{Expected number} = \frac{(\text{first value}) \times (\text{second value})}{\text{fourth value}}.$$

24. The method of claim 1, wherein the step of adjusting includes a step of subtracting the expected number of compartments from the third value.

* * * * *